US009090627B2

(12) United States Patent
Du Bois et al.

(10) Patent No.: US 9,090,627 B2
(45) Date of Patent: Jul. 28, 2015

(54) BATRACHOTOXIN ANALOGUES, COMPOSITIONS, USES, AND PREPARATION THEREOF

(71) Applicants: Justin Du Bois, Menlo Park, CA (US); Abigail Sloan Devlin, San Francisco, CA (US); Matthew M. Logan, Brooklyn, MI (US); Frederic Menard, Menlo Park, CA (US); Tatsuya Toma, Palo Alto, CA (US)

(72) Inventors: Justin Du Bois, Menlo Park, CA (US); Abigail Sloan Devlin, San Francisco, CA (US); Matthew M. Logan, Brooklyn, MI (US); Frederic Menard, Menlo Park, CA (US); Tatsuya Toma, Palo Alto, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 14/106,115

(22) Filed: Dec. 13, 2013

(65) Prior Publication Data
US 2014/0171410 A1     Jun. 19, 2014

Related U.S. Application Data

(60) Provisional application No. 61/737,229, filed on Dec. 14, 2012.

(51) Int. Cl.
*C07D 267/12*    (2006.01)
*C07D 413/02*    (2006.01)
*C07D 498/08*    (2006.01)

(52) U.S. Cl.
CPC .................... *C07D 498/08* (2013.01)

(58) Field of Classification Search
CPC ........................ C07D 413/02; C07D 267/12
USPC ....................... 540/546; 514/211.09
See application file for complete search history.

(56) References Cited

FOREIGN PATENT DOCUMENTS

WO     2010/027641 A2     3/2010

OTHER PUBLICATIONS

Marki and Witkop, Experientia, 1963, 19, 329.
Daly et al., J. Am Chem. Soc., 1965, 87, 124.
Tokuyama and Daly, Tetrahedron, 1983, 39, 41.
Tokuyama et al., J. Am Chem. Soc., 1969, 91, 3931.
Albuquerque et al., Science, 1971, 172, 995.
Wang and Wang, Cell. Sign., 2003, 15, 151.
Quandt and Narahashi, Proc. Nat. Acad. Sci. USA, 1982, 79, 6732.
Garraffo and Spande, Heterocycles, 2009, 79, 195.
Tokuyama et al., J. Am Chem. Soc., 1968, 90, 1917.
Karle and Karle, Acta Crystallogr., 1969, B25, 428.
Gillardi, Acta Crystallogr., 1970, B26, 440.
Kurosu et al., J. Am Chem. Soc., 1998, 120, 6627.
Imhof et al., Helv. Chim. Acta, 1973, 56, 139.
Imhof et al., Helv. Chim. Acta, 1972, 55, 1151.
Schumaker and Keana, J. Chem. Soc. Chem. Comm., 1972, 622.
Keana and Schumaker, J. Org. Chem., 1976, 41, 3840.
Magnus et al., J. Chem Soc. Chem. Comm., 1985, 1185.
Hudson et al., Tet. Lett., 1993, 34, 7295.
Trudeau and Deslongchamps, J. Org. Chem., 2004, 69, 832.
Lacrouts et al., Synlett., 2005, 18, 2767.
Schow et al., Bioorg. Med. Chem. Lett., 1997, 7, 181.
Khodorov et al., Cell. Molec. Neurobio., 1992, 12, 59.
Warnick et al., J. Pharmacol. Exper. Ther., 1975, 193, 232.
Akai et al., Angew. Chem. Int. Ed., 2008, 47, 7673.
Shakespeare and Johnson, J. Am. Chem. Soc., 1990, 112, 8578.
Atanes et al., Tet. Lett., 1998, 39, 3039.
Collis et al., Austr. J. Chem. 1997, 50, 505.
Fujita et al., J. Am. Chem. Soc., 2004, 126, 7548.
Gampe and Carreira, Angew. Chem. Int. Ed., 2011, 50, 2962.
Devlin and Du Bois, Chemical Science, 2013, 4, 1059.

*Primary Examiner* — Bruck Kifle
(74) *Attorney, Agent, or Firm* — David A. Roise; VLP Law Group LLP

(57) ABSTRACT

Compounds relating to batrachotoxin are provided, in particular analogs that modulate the activity of sodium channels. Also provided are pharmaceutical compositions comprising compounds of the invention and a pharmaceutically acceptable carrier, including vehicles that modulate transdermal permeation of the compound. The subject compounds are useful in treatments, including treatments to reduce neuronal activity or to bring about muscular relaxation. The compounds also find use in the treatment of subjects suffering from a voltage-gated sodium channel-enhanced ailment or from pain. Further methods are provided for the preparation of the batrachotoxin-related compounds.

41 Claims, 9 Drawing Sheets

BATRACHOTOXIN ANALOGUES, COMPOSITIONS, USES, AND PREPARATION THEREOF

CROSS-REFERENCE TO RELATED APPLICATIONS

This application claims the benefit of U.S. Provisional Application No. 61/737,229, filed Dec. 14, 2012, which is incorporated by reference herein in its entirety.

STATEMENT REGARDING FEDERALLY SPONSORED RESEARCH

This invention was made with Government support under contract NS045684 awarded by the National Institutes of Health. The Government has certain rights in this invention.

BACKGROUND OF THE INVENTION

Batrachotoxin (BTX, 1), homobatrachotoxin, and batrachotoxinin A comprise a small family of complex steroidal alkaloids originally isolated in sparing amounts from the skin of Colombian poison dart frogs of the genus *Phyllobates*. See Marki and Witkop, *Experientia*, 1963, 19, 329; Daly et al., *J. Am Chem. Soc.*, 1965, 87, 124. β-Hydroxybatrachotoxin and 4β-hydroxyhomobatrachotoxin were also isolated as minor components, see: Tokuyama and Daly, *Tetrahedron*, 1983, 39, 41. Batrachotoxin acts as a selective agonist of voltage-gated sodium channels ($Na_V$s) and is among the most potent non-peptidic toxins known ($LD_{50}$ in mice=2 μg/kg). Tokuyama et al., *J. Am Chem. Soc.*, 1969, 91, 3931; Albuquerque et al., *Science*, 1971, 172, 995. The binding of BTX to $Na_V$s results in a remarkably complex array of responses, including hyperpolarization of threshold activation, elimination of inactivation gating, and reduction of single channel conductance. Wang and Wang, *Cell. Sign.*, 2003, 15, 151; Quandt and Narahashi, *Proc. Nat. Acad. Sci. USA*, 1982, 79, 6732. While there exist other small molecule modulators of $Na_V$s, arguably none show activity that is as multifaceted as BTX. Severely limited quantities of BTX, however, frustrate any efforts to evaluate structure-function relationships and to utilize BTX or select analogues to interrogate mechanisms of ion selectivity and channel gating. The sacrifice of over 10,000 Colombian poison dart frogs, which are now endangered, resulted in the isolation of 180 mg of BTX and 100 mg of homoBTX (Garraffo and Spande, *Heterocycles*, 2009, 79, 195), and frogs raised in captivity do not produce the toxin (Daly et al., *Science*, 1980, 208, 1383).

Batrachotoxin (BTX) 1; R = Me
Homobatrachotoxin (homoBTX); R = Et

Batrachotoxin A

Batrachotoxin offers numerous intriguing challenges to the chemist interested in de novo synthesis. Tokuyama et al., *J. Am Chem. Soc.*, 1968, 90, 1917; Karle and Karle, *Acta Crystallogr.*, 1969, B25, 428; Gillardi, *Acta Crystallogr.*, 1970, B26, 440. The E-ring homomorpholine is unique among secondary metabolite structures, and the 9α-hydroxy 3β-hemiketal, C16-C17 unsaturation, and 20 cc pyrrole ester do not appear in other steroidal natural products. To date, only a single de novo route to (±)-batrachotoxinin A has been reported (Kurosu et al., *J. Am Chem. Soc.*, 1998, 120, 6627), although Imhof and co-workers completed a partial synthesis of an analog of (−)-batrachotoxinin A in which the stereochemistry of the C20 alcohol was inverted (S instead of R) (Imhof et al., *Helv. Chim. Acta*, 1973, 56, 139; Imhof et al., *Helv. Chim. Acta*, 1972, 55, 1151). The impressiveness of the BTX synthesis notwithstanding, the length and linear nature of the synthesis does not provide a viable means to BTX analogues. Other reports describe preparations of A/B/C ring system variants, but the variants that have been tested show modest to little effect as $Na_V$ modulators. Schumaker and Keana, *J. Chem. Soc. Chem. Comm.*, 1972, 622; Keana and Schumaker, *J. Org. Chem.*, 1976, 41, 3840; Magnus et al., *J. Chem Soc. Chem. Comm.*, 1985, 1185; Hudson et al., *Tet. Lett.*, 1993, 34, 7295; Trudeau and Deslongchamps, *J. Org. Chem.*, 2004, 69, 832; Lacrouts et al., *Synlett.*, 2005, 18, 2767; Schow et al., *Bioorg. Med. Chem. Lett.*, 1997, 7, 181. The preparation of the C/D/E skeleton has not been reported, in spite of the fact that mouse lethality and electrophysiology data indicate that variations to the C, D, or E rings dramatically alter BTX activity. Khodorov et al., *Cell. Molec. Neurobio.*, 1992, 12, 59; Warnick et al., *J. Pharmacol. Exper. Ther.*, 1975, 193, 232. Without intending to be bound by theory, homology modelling and protein mutagenesis data suggest that BTX binds to the inner pore region of $Na_V$ through primary contacts with the C/D/E ring unit. Tikhonov and Zhorov, *FEBS Lett.*, 2005, 579, 4207; Du et al., *J. Biol. Chem.*, 2011, 286, 13151; Wang and Wang, *Biophys. J.*, 1999, 76, 3141; Wang and Wang, *Proc. Nat. Acad. Sci. USA*, 1998, 95, 2653; Wang et al., *Pflugers Arch.*, 2007, 454, 277; Du et al., *Biochem. J.*, 2009, 419, 377; Wang et al., *Mol. Pharmacol.*, 2001, 59, 1100; Wang et al., *Channels*, 2007, 1, 179.

Compounds with structures unrelated to that of BTX have been reported to compete with the binding of BTX to $Na_V$ and to display isoform-specific $Na_V$ blocking effects. PCT International Publication No. WO2010/027641.

The strong therapeutic potential of batrachotoxin in the treatment of pain and other diseases of the nervous system make it an attractive candidate for structural modification and analysis. There is thus a need for improved compound analogues of batrachotoxin, pharmaceutical compositions, methods of use, and methods of preparation.

Effective delivery of an active compound to a desired target is also of major importance in all types of pharmacotherapy. Transdermal delivery of drugs represents an attractive alternative to oral or parenteral delivery, and, over the last few decades, has made an important contribution to medical practice. See Prausnitz and Langer, *Nature Biotechnology,* 2008, 26, 1261. Trans-dermal delivery has many advantages in comparison to other delivery routes. See, e.g., Prausnitz and Langer, *Nature Biotechnology,* 2008, 26, 1261; Jepps et al., *Advanced Drug Delivery Reviews,* 2013, 65, 152. Oral analgesics, for example, are commonly prescribed for the treatment of acute and chronic pain, but often produce adverse systemic effects such as potentially fatal respiratory depression, nausea, and addiction. Argoff, *Mayo Clinic Proceedings,* 2013, 88, 195. Clinically effective drug concentrations can be introduced at a peripherally located site of injury or inflammation by topical administration without resulting in high systemic concentrations that may increase the likelihood of adverse effects. Argoff, *Mayo Clinic Proceedings,* 2013, 88, 195; McCleane, *Medical Clinics of North America,* 2007, 91, 125. Nevertheless, the main challenge in topical applications and transdermal drug delivery is the penetration through the skin barrier. Determining the permeability of a given compound through the human skin is quite difficult, however, owing to the highly complex nature of the skin structures and the various proposed mechanisms that constitute the delivery pathway. Jepps et al., *Advanced Drug Delivery Reviews,* 2013, 65, 152.

SUMMARY OF THE INVENTION

The present invention addresses these and other problems by providing compounds, pharmaceutical compositions, methods of use of compounds, and methods of preparation of compounds relating to batrachotoxin.

In particular, according to one aspect of the invention, compounds are provided as represented by structural formula (I):

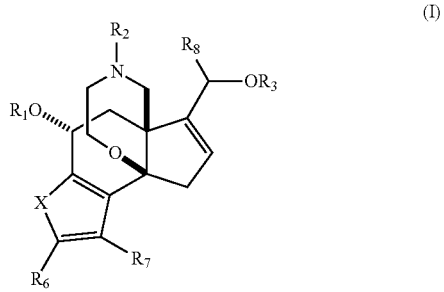

(I)

or a pharmaceutically acceptable salt, stereoisomer, or prodrug thereof, wherein:

- $R_1$ is hydrogen, alkyl, alkenyl, alkynyl, aryl, aralkyl, heteroaryl, heteroaralkyl, cycloalkyl, cycloalkenyl, cycloalkylalkyl, heterocyclyl, heterocyclylalkyl, —C(O)R, or a protecting group, and is optionally substituted with 1 to 3 A groups;
- $R_2$ is hydrogen, alkyl, alkenyl, alkynyl, aryl, aralkyl, heteroaryl, heteroaralkyl, cycloalkyl, cycloalkenyl, cycloalkylalkyl, heterocyclyl, heterocyclylalkyl, —C(O)R, or a protecting group, and is optionally substituted with 1 to 3 A groups;
- $R_3$ is hydrogen, alkyl, alkenyl, alkynyl, aryl, aralkyl, heteroaryl, heteroaralkyl, cycloalkyl, cycloalkenyl, cycloalkylalkyl, heterocyclyl, heterocyclylalkyl, —C(O)R, or a protecting group, and is optionally substituted with 1 to 3 A groups;
- X is O, S, or

- $R_4$, $R_5$, $R_6$, and $R_7$ are independently hydrogen, alkyl, alkenyl, alkynyl, alkoxy, alkylamino, aryl, aryloxy, arylamino, aralkyl, aralkoxy, aralkamino, heteroaryl, heteroaryloxy, heteroarylamino, heteroaralkyl, heteroaralkoxy, heteroaralkamino, cycloalkyl, cycloalkenyl, cycloalkylalkyl, cycloalkoxy, cycloalkamino, heterocyclyl, heterocyclyloxy, heterocyclylamino, heterocyclylalkyl, heterocyclylalkoxy, heterocyclylalkamino, silyl, sulfonyl, hydroxyl, thio, amino, alkanoylamino, aroylamino, aralkanoylamino, alkylcarboxy, carbonate, carbamate, guanidinyl, urea, halo, trihalomethyl, cyano, nitro, phosphoryl, sulfonyl, sulfonamindo, or azido, and are optionally substituted with 1 to 3 A groups;
- $R_8$ is hydrogen, alkyl, alkenyl, alkynyl, alkoxy, aryl, aralkyl, heteroaryl, heteroaralkyl, cycloalkyl, cycloalkenyl, cycloalkylalkyl, heterocyclyl, or heterocyclylalkyl, and is optionally substituted with 1 to 3 A groups;
- each R is independently hydrogen, alkyl, alkenyl, alkynyl, alkoxy, alkylamino, aryl, aryloxy, arylamino, aralkyl, aralkoxy, aralkamino, heteroaryl, heteroaryloxy, heteroarylamino, heteroaralkyl, heteroaralkoxy, heteroaralkamino, cycloalkyl, cycloalkenyl, cycloalkylalkyl, cycloalkoxy, cycloalkamino, heterocyclyl, heterocyclyloxy, heterocyclylamino, heterocyclylalkyl, heterocyclylalkoxy, or heterocyclylalkamino, and is optionally substituted with 1 to 3 A groups; and
- each A is independently alkyl, alkenyl, alkynyl, alkoxy, alkanoyl, alkylamino, aryl, aryloxy, arylamino, aralkyl, aralkoxy, aralkanoyl, aralkamino, heteroaryl, heteroaryloxy, heteroarylamino, heteroaralkyl, heteroaralkoxy, heteroaralkanoyl, heteroaralkamino, cycloalkyl, cycloalkenyl, cycloalkylalkyl, cycloalkoxy, cycloalkanoyl, cycloalkamino, heterocyclyl, heterocyclyloxy, heterocyclylamino, heterocyclylalkyl, heterocyclylalkoxy, heterocyclylalkanoyl, heterocyclylalkamino, hydroxyl, thio, amino, alkanoylamino, aroylamino, aralkanoylamino, alkylcarboxy, carbonate, carbamate, guanidinyl, urea, halo, trihalomethyl, cyano, nitro, phosphoryl, sulfonyl, sulfonamido, or azido.

In some embodiments of the invention, the $R_1$ group is hydrogen, alkyl, —C(O)R, or a protecting group, and is optionally substituted with 1 to 3 A groups.

According to more specific embodiments, the $R_1$ group is hydrogen, alkyl, or a protecting group.

In even more specific embodiments, the $R_1$ group is methoxymethyl.

In some embodiments of the invention, the $R_2$ group is hydrogen, alkyl, —C(O)R, or a protecting group, and is optionally substituted with 1 to 3 A groups.

In other embodiments, $R_2$ is alkyl, and is optionally substituted with 1 to 3 A groups.

In still other embodiments, $R_2$ is methyl.

According to some embodiments, the $R_3$ group is alkyl, aryl, heteroaryl, or —C(O)R, and is optionally substituted with 1 to 3 A groups.

In specific embodiments, $R_3$ is —C(O)R, and R is alkyl, aryl, heteroaryl, arylamino, or heteroarylamino, and is optionally substituted with 1 to 3 A groups.

In still other specific embodiments, $R_3$ is —C(O)R, and R is a substituted pyrrole.

In even more specific embodiments, $R_3$ is —C(O)R, and R is

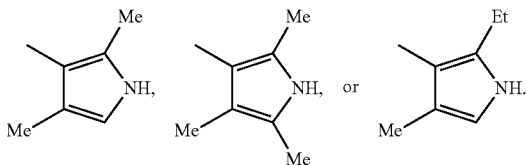

According to other embodiments, the $R_4$, $R_5$, $R_6$, and $R_7$ groups are independently hydrogen, alkyl, alkoxyl, cycloalkyl, heterocyclyl, silyl, sulfonyl, carbonate, hydroxyl, thio, amino, halo, cyano, or nitro, and are optionally substituted with 1 to 3 A groups.

In specific embodiments, the $R_4$, $R_5$, $R_6$, and $R_7$ groups are independently hydrogen, alkyl, alkoxy, silyl, or halo.

In more specific embodiments $R_4$, $R_5$, $R_6$, and $R_7$ are hydrogen.

In some embodiments, the $R_8$ group is hydrogen or alkyl, and in some embodiments methyl.

In certain embodiments, R is independently alkyl, aryl, heteroaryl, arylamino, or heteroarylamino.

According to some embodiments, the X group is O or

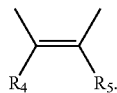

In preferred embodiments of the invention, compounds are provided as represented by structural formula (I), wherein
$R_1$ is hydrogen, —C(O)R, or a protecting group, and is optionally substituted with 1 to 3 A groups;
$R_2$ is hydrogen, alkyl, —C(O)R, or a protecting group, and is optionally substituted with 1 to 3 A groups;
$R_3$ is —C(O)R, and R is alkyl, aryl, heteroaryl, arylamino, or heteroarylamino, and is optionally substituted with 1 to 3 A groups;
$R_4$, $R_5$, $R_6$, and $R_7$ are independently hydrogen, alkyl, alkoxyl, cycloalkyl, heterocyclyl, silyl, sulfonyl, carbonate, hydroxyl, thio, amino, halo, cyano, or nitro, and are optionally substituted with 1 to 3 A groups;
$R_8$ is hydrogen or alkyl;
R is independently alkyl, aryl, heteroaryl, arylamino, or heteroarylamino; and
X is O or

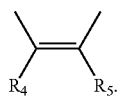

According to another aspect, the invention provides pharmaceutical compositions comprising the subject compound and a pharmaceutically acceptable carrier.

According to yet another aspect, the invention provides packaged pharmaceuticals comprising the subject pharmaceutical composition and instructions for using the composition to treat pain in a mammalian subject.

According to still yet another aspect, the invention provides methods of treatment in a subject, comprising administering to the subject a compound of the invention in an amount effective to treat the subject.

In one embodiment, the treatment reduces neuronal activity in the subject or brings about muscular relaxation in the subject.

In another embodiment, the subject suffers from a voltage-gated sodium channel-enhanced ailment.

In specific embodiments, the voltage-gated sodium channel-enhanced ailment is selected from the group consisting of: acute pain, anal fissures, arthritis, back pain, chronic pain, dental pain, fibromyalgia, joint pain, migraine headaches, neck pain, neuropathic pain, obstetric pain, post-herpetic neuralgia, post-operative pain, shingles, tension headaches or trigeminal neuralgia, cancer, cardiac arrythmia, epilepsy, focal dystonia, hyperhidrosis, muscle spasms, and urinary bladder relaxation.

In another embodiment, the subject suffers from pain.

In specific embodiments, the pain is acute pain, anal fissure pain, arthritis pain, back pain, cancer pain, chronic pain, dental pain, fibromyalgia pain, joint pain, migraine headache pain, neck pain, visceral pain, neuropathic pain, obstetric pain, post-herpetic neuralgia pain, post-operative pain, sympathetically maintained pain, shingles pain, tension headache pain, trigeminal neuralgia pain, myositis pain, musculoskeletal pain, lower back pain, pain from sprains and strains, pain associated with functional bowel disorders such as non-ulcer dyspepsia, non-cardiac chest pain and irritable bowel syndrome, pain associated with myocardial ischemia, toothache pain, or pain from dysmenorrhea. In some embodiments, the pain is sunburn pain.

In still another embodiment, the treatment reduces or eliminates wrinkles.

In another aspect, the invention provides pharmaceutical compositions comprising the subject compound and a vehicle that modulates transdermal permeation of the compound. The vehicle is, in some embodiments, an organic solvent, such as an alcohol or dimethyl sulfoxide, or an emulsion. In specific embodiments, the alcohol is ethanol and the emulsion is a cream. In even more specific embodiments, the cream is a eutectic mixture of local anesthetics.

DETAILED DESCRIPTION OF THE INVENTION

Figure 1:
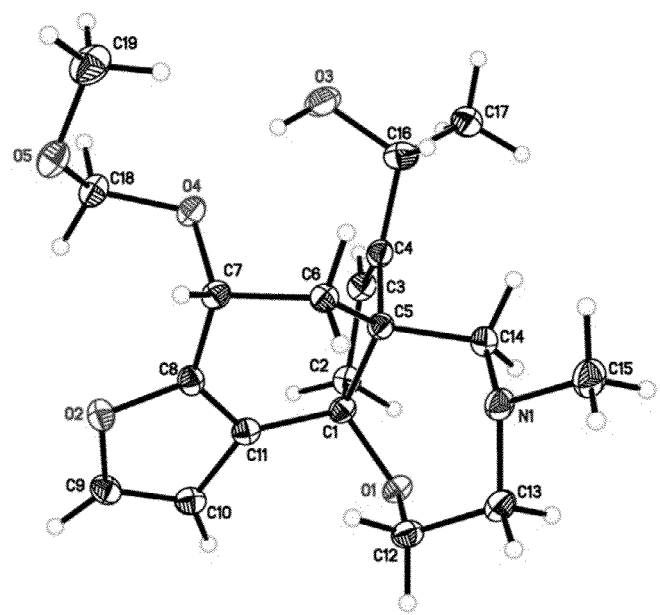
FIG. 1. X-ray crystallographic structure of compound 27, where the R group is hydrogen.

In order to provide compounds therapeutically useful in the modulation of $Na_V$ activity and in determining how toxin binding alters $Na_V$ function, molecular probes that conserve the C/D/E ring system of BTX and the pendant pyrrole ester have been prepared. The synthetic efforts disclosed herein provide a synthesis of a furan-derived C/D/E ring intermediate, which is appropriately configured to enable access to both BTX and A/B ring BTX derivatives. The versatility of this furan structure is demonstrated for the synthesis of the pentacyclic core of the natural product and related analogues. Alternative structures that include a 6-membered fused aromatic ring in place of the furan ring are likewise provided. The BTX analogues have been shown to modulate the activity of Nav channels and are thus useful in pharmaceutical compositions and methods of treatment of conditions involving Nav channels, such as pain.

Bioelectricity and the Action Potential

The action potential is the fundamental unit of communication of excitable cells (Johnston et al., *Foundations of Cellular Neurophysiology*; The MIT Press: Cambridge, Mass., 1995). Defined as a transient reversal of membrane potential, an action potential is propagated along the length of an axon by the concomitant action of voltage-gated sodium and potassium ion channels ($Na_V$ and $K_V$, respectively). Central to their function is the development and maintenance of membrane potential (Wright, *Adv. Physiol. Educ.* 2004, 28, 139-42).

Transmembrane voltages exist for all mammalian cells and range in value from −40 to −90 mV. Membrane potential derives from the equilibration of electric potential and chemical potential across a cell membrane. The $Na^+/K^+$-ATPase, which is responsible for about 70% of energy consumption of the entire nervous system, transports three $Na^+$ ions out of the cell while pumping two $K^+$ ions into the cell per cycle, creating $Na^+$ and $K^+$ concentration gradients across the cell membrane. While cell membranes are impermeant to polar species, the membranes of excitable cells contain leak channels that are more permeant to potassium ions than to sodium ions. Therefore, potassium ions flow down their concentration gradient from inside the cell to the outside, making the outside of the cell positive relative to the inside of the cell. The resulting electric potential becomes stronger and the driving force for passage of potassium ions across the membrane becomes weaker since the developing electric potential opposes the diffusion force.

In the absence of any other leak channels, the potential at which these two forces are in equilibrium is the potassium equilibrium potential and is defined by the Nernst equation:

$$E = \frac{RT}{zF} \ln \frac{[\text{ion outside cell}]}{[\text{ion inside cell}]}$$

where E is the equilibrium potential for potassium, R is the ideal gas constant, T is temperature, z is the charge on potassium ion, and F is Faraday's constant. In a typical mammalian cell at 37° C., [$K^+$ outside cell] is 5 mM, and [$K^+$ inside cell] is 140 mM, giving a potassium equilibrium potential of −89 mV.

The sodium equilibrium potential can be similarly calculated. The sodium equilibrium potential is less important than the potassium equilibrium potential in the discussion of membrane potential because most leak channels are far less conductive to sodium ions than to potassium ions. However, the sodium equilibrium potential becomes more important over the course of an action potential, as is discussed below. Calculated in the same manner, the sodium equilibrium potential ($Na^+$ outside cell=145 mM, $Na^+$ inside cell=10 mM) is determined to be +71 mV.

Membrane potential can be more precisely determined by taking a weighted average of the potassium and sodium equilibrium potentials, with the magnitude of weighting determined by ion permeability. This method of determining membrane potential is captured in the Goldman equation:

$$V_m = E_{Na} \frac{G_{Na}}{G_{Na} + G_K} + E_K \frac{G_K}{G_{Na} + G_K}$$

where $V_m$ is membrane potential, $E_X$ is the equilibrium potential for ion X, and $G_X$ is the conductance of ion X. Using the above determined equilibrium potentials for $Na^+$ and $K^+$, and assuming $G_K = 20\ G_{Na}$ (i.e. the membrane is 20 times more permeable to potassium than to sodium at resting potential), membrane potential is found to be −81 mV, which closely correlates to experimentally determined values in mammalian neurons.

While these leak channels play a critical role in the development and maintenance of membrane potential, it is the concomitant action of voltage-gated sodium and potassium ion channels that propagate action potentials (Hille, *Ion Channels of Excitable Membranes*, 3rd ed.; Sinauer Associates: Sunderland, Mass., 2001). These ion channels gate (i.e., open and close) in response to changes in membrane potential. Most of these channels remain closed at resting potential, however, if a sufficiently large depolarization occurs, a positive feedback response results. While both sodium and potassium channels open in response to depolarization, sodium channels open faster. Therefore, inward sodium current dominates the first phase of an action potential, swamping any currents associated with leak channels and causing further depolarization of the membrane. In this "rising phase" of an action potential, membrane potential rapidly approaches the sodium equilibrium potential as sodium ion channels represent most of the membrane's ionic conductance. Furthermore, this "all or nothing" characteristic of an action potential means that once a certain threshold potential is achieved, an action potential is "fired". The characteristics of this action potential depend not on the characteristics of the initial stimulus, but on the organization and concentration of ion channels in the neuron. In the "falling phase" of an action potential, sodium channels become inactivated and the outward current of potassium channels dominates, moving the membrane potential back towards the potassium equilibrium potential and repolarizing the membrane. This depolarization-repolarization cycle is propagated along the membranes of excitable cells, and along with the action of neurotransmitters at synapses, forms the basis of all neuronal signaling.

Structural Features of Tetrameric Ion Channels

Voltage-gated ion channels are unique molecular machines that alter their conformation in response to changes in membrane potential. Because of their ubiquity in the nervous systems of all life forms, their structure and mechanics are of great interest. A large body of structural information exists for the potassium channel as X-ray crystal structures of both eukaryotic and prokaryotic proteins have been solved. A review of the general features of the potassium channel is instructive to our understanding of the features of the sodium channel. Potassium channels exist as tetrameric structures in which four protein subunits, each containing six transmembrane α-helices (S1-S6), arrange in a C-4 symmetric manner around a central, ion-conducting pore. In some cases these four proteins are identical, in others they are related but not identical. Of particular interest is the channel pore, which must discriminate between potassium ions and the smaller sodium and lithium ions. Nearly all known potassium channels contain a threonine-valine-glycine-tyrosine-glycine (T-V-G-Y-G) signature sequence in each domain, which lines the channel pore and comprises the selectivity filter (Heginbotham et al., *Science* 1992, 258, 1152-1155). Mutation of any of these residues severely compromises ion selectivity (Heginbotham et al., *Biophys. J.* 1994, 66, 1061-1067).

Selectivity for potassium over the smaller sodium ion derives from thermoneutral dehydration of potassium ions as they enter the selectivity filter (Doyle et al., *Science* 1998, 280, 69-77). The dimensions of the selectivity filter allow for precise binding and stabilization of naked potassium ions through interactions with backbone carbonyls in the signature sequence. The hydrated sodium ion is too large to fit into the selectivity filter, and the dehydrated ion is not effectively stabilized, so that dehydration is thermodynamically disfavored. The permeability of lithium ions through $K_V$ in its conductive state is immeasurably low, and selectivity for potassium over sodium is >10,000:1.

In spite of strong binding interactions within the selectivity filter for dehydrated potassium ions, conduction rates as high as $10^8$ ions/second, approaching the diffusion limit, are achieved. This high conductivity can be explained by the fact that the selectivity filter contains four $K^+$ binding sites in relatively close proximity—the total length of the selectivity filter is about 7.5 Å. When a single $K^+$ ion is bound in the selectivity filter there is a strong attractive interaction between protein and ion, however when two ions are bound, this attractive interaction is balanced by an electrostatic repulsion between the two cations. At physiologically relevant $K^+$ concentrations (150 mM), two $K^+$ ions are contained in the selectivity filter at any given time, eliminating any thermodynamic preference for a single ion to remain lodged in the channel pore (Morais-Cabral et al., *Nature* 2001, 414, 37-42).

Structure and Mechanics of the Voltage-Gated Sodium Channel

In contrast to the potassium channel, an X-ray crystal structure of a mammalian $Na_V$ has not been solved, due in large part to the difficulty in obtaining large quantities of the protein in a pure, correctly folded state (but see Payandeh et al., *Nature* 2011, 475, 353 and Payandeh et al., *Nature* 2012, 486, 135 for structural studies of a bacterial sodium channel). Towards that end, the structure of a bacterial homolog of $Na_V$ was recently reported (Nurani et al., *Biochemistry* 2008, 47, 8114-21), and subsequently was linked to a larger family of orthologs, forming a superfamily of proteins (Koishi et al., *J. Biol. Chem.* 2004, 279, 9532-9538). These proteins are believed to be involved in motility, chemotaxis and pH homeostasis (Ito et al., *Proc. Natl. Acad. Sci. U.S.A.* 2004, 101, 10566-10571). More recently, methods for generating milligram quantities of this protein have been reported (Nurani et al., *Biochemistry* 2008, 47, 8114-21). This bacterial homolog consists of only a single six transmembrane domain, which may form a functional unit as a tetramer, however its structural homology to the mammalian sodium channel is not yet clear.

Insights into $Na_V$ structure have relied on a combination of primary sequence analysis, solution NMR analysis, homology modeling based on $K_V$, mutagenesis and toxin binding. Primary sequence analysis of $Na_V$ (Noda et al., *Nature* 1984, 312, 121-128; Guy et al., *Proc. Natl. Acad. Sci. U.S.A.* 1986, 508, 508-512) suggests that, like $K_V$, $Na_V$ is organized as a tetramer with four homologous domains, each containing six transmembrane α-helices. $Na_V$ is a single protein with each domain connected by a large intracellular loop. This so-called α-subunit contains all of the necessary components for a channel that activates and inactivates with changes in membrane potential, and is selective for $Na^+$. In neuronal cells, this α-subunit is generally associated with one or two β-subunits, which slightly alter the channel's gating characteristics. The α-subunit is heavily glycosylated, with carbohydrate comprising between 15%-30% of its molecular weight, and further post-translational modification occurs in the form of sulfation, acylation and phosphorylation (Schmidt et al., *J. Biol. Chem.* 1987, 262, 13713-13723). This molecular topology has been supported by extensive biochemical and electrophysiological studies (Catterall et al., *Neuron* 2000, 26, 13-25).

Cryo-electron microscopy has been used to obtain three-dimensional images of the $Na_V$ α-subunit at 19 Å resolution (Sato et al., *Nature* 2001, 409, 1047-1051). The images were acquired through single particle analysis of the solubilized protein, and signal to noise was improved by signal averaging of proteins that presented in similar orientations. The images show the expected 4-fold symmetry as well as, unexpectedly, a network of pores, one in each domain. Without intending to be bound by theory, it has been hypothesized that, like the potassium channel, a single ion-conducting pore exists through the axis of rotation about the four domains, and that the additional pores represent channels through which the voltage sensor in each domain may pass. The additional pores were not observed in any potassium crystal structure, however, and this hypothesis remains to be further substantiated. While these experiments provide a tantalizing glimpse of the macro-molecular features of the sodium channel, techniques delivering higher resolution will be required to develop a detailed understanding of the mechanical features of the sodium channel.

Two essential mechanical features of $Na_V$ are the ability to activate in response to membrane depolarization, and to inactivate rapidly thereafter. As with $K_V$, activation is coupled to movement of the positively charged S4, the voltage sensor, in the extracellular direction in all four protein domains. S4 contains 4, 5, 6, and 8 positively charged residues in D1, D2, D3 and D4, respectively, positioned at every third residue in the primary sequence (Yang et al., Neuron 1996, 16, 113-22). Studies of gating currents have shown that the equivalent of at least 10 positive charges must cross from the intracellular side of the membrane potential to the external side (Hirschberg et al., J. Gen. Physiol. 1995, 106, 1053-1068). The technique of cysteine scanning followed by intra/extracellular reaction with methanethiosulfonate reagents has shown that in S4/D4 two of the charged residues completely translocate from an intracellularly accessible position to an extracellularly accessible position, and a third charged moiety likely translocates partly through the membrane's potential difference (Yang et al., Neuron 1996, 16, 113-22). Multiplication of this charge movement among four domains accounts for measured gating currents.

Sodium channels must rapidly close following activation, a process that is not the microscopic reverse of activation, but instead leads to a unique, inactivated state. Defects in sodium channel inactivation lead to a variety of symptoms of neuronal hyperexcitability within the heart and throughout the central nervous system (Lehmann-Horn et al., Phys. Rev. 1999, 79, 1217-1372; Lehmann-Horn et al., Pharma. News 2001, 8, 29-36). The molecular mechanisms responsible for inactivation have been studied extensively (Ulbricht Phys. Rev. 2005, 85, 1271-1301). Inactivation appears to occur via occlusion of the channel pore from the cytoplasmic side of the membrane with a conserved sequence of three peptides—isoleucine-phenylalanine-methionine; known as the I-F-M triad—found on the linker region between domains three and four (Bosmans et al., Nature 2008, 456, 202-208 and references therein). Solution state NMR spectroscopy studies (Rohl et al., Biochemistry 1999, 38, 855-861) reveal a helix-turn-latch motif, in which a flexible, conformationally mobile linker follows a stable helix. The linker is attached to a "latch", the I-F-M motif that appears to interact directly with the channel pore, forming a strong hydrophobic interaction that occludes the channel pore in the inactivated state.

The extracellular pore of the sodium channel is of tremendous interest since it is the binding site of the neurotoxins tetrodotoxin (TTX) and saxitoxin (STX), contains the components necessary to impart selectivity for sodium, and appears to be organized quite differently from the potassium channel. The $Na_V$ pore is comprised of the reentrant P-loops connecting S5 to S6 in each of the four protein domains (Yu et al., Genome Biol. 2003, 4, 207.1-207.7). An "outer vestibule" consisting of glutamate-glutamate-methionine-aspartate (E-E-M-D) residues is conserved in all channel isoforms, and in contrast to the potassium channel, the selectivity filter in $Na_V$ consists of a single ring of four amino acids, an aspartate-glutamate-lysine-alanine (D-E-K-A) motif. This selectivity filter is consistent with an ion channel bearing a close phylogenetic relationship to calcium channels (Yu et al., Pharmacol. Rev. 2005, 57, 387-395), and indeed mutation of the D-E-K-A locus to E-E-E-E, as found in the voltage-gated calcium channel, confers the channel with calcium selectivity (Heinemann et al., Nature 1992, 356, 441-443; Favre et al., Biophys. J. 1996, 71, 3110-3125). This close relationship between $Na_V$ and $Ca_V$ channels suggests that structural insights into $Na_V$ may have implications for this broader family of voltage-gated ion channels. In further contrast to the potassium channel, the D-E-K-A locus appears to have some degree of motility during gating and in passing from the nonconductive state to the conductive one (Benitah et al., J. Neurosci. 1999, 19, 1577-1585), and this molecular motion may be involved in slow inactivation (Xiong et al., J. Gen. Physiol. 2003, 122, 323-332). Finally, modeling studies suggest that it is not backbone carbonyls that make up the narrowest part of the channel pore, but in fact the amino acid side chains.

The β-Subunits

While the $Na_V$ α-subunit contains all of the machinery necessary to form a functional and selective ion channel, complexation with one or two β-subunits has subtle but important effects on gating and on channel expression at the plasma membrane. There are three known β-subunits (β1-β3), as well as a fourth that is a splice variant of β1. β1 and β3 are noncovalently bound to the α-subunit, while β2 and β4 form disulfide bonds to the α-subunit (Catterall et al., Neuron 2000, 26, 13-25). Sodium channels in skeletal muscle generally only contain the β1 subunit, whereas other isoforms may contain any of the β subunits. The β-subunits are much smaller than the α-subunits with molecular weights around 45 kDa. These proteins are comprised of a single transmembrane segment, with a large extracellular amino terminus and a smaller intracellular carboxy terminus.

Sodium channel β-subunits play an important role in modifying channel gating with respect to both the voltage dependence and kinetics of activation and inactivation (Isom, Neuroscientist 2001, 7, 42-54 and references therein). For example, when the β1 subunit is coexpressed with the $Na_V$ skeletal muscle α-subunit, activation and inactivation rates are increased and more closely resemble gating characteristics observed in native tissue (Isom et al., Neuron 1994, 12, 1183-1194; Isom et al., J. Biol. Chem. 1994, 270, 3306-3312). Importantly, the gating characteristics of $Na_V$ as well as its modulation by β-subunits are dependent on the particular heterologous host in which the proteins are expressed (Isom, Neuroscientist 2001, 7, 42-54 and references therein). For example, $Na_V1.4$ gates relatively slowly when expressed in Xenopus oocytes, and addition of the β1 subunit results in major changes to channel gating kinetics. When these same channels are expressed in mammalian fibroblasts, addition of the β1 subunit has little effect on gating kinetics.

$Na_V$ β-subunits also play an important role in channel expression at the plasma membrane. Structurally, the large extracellular N-terminus likely adopts an immunoglobulin fold and bears sequence homology with the L1 family of cell adhesion molecules (CAMs) that modulate cell-cell interactions and cell adhesion (Isom et al., Cell 1995, 83, 433-442; Isom et al., Nature 1996, 383, 307-308). These subunits are involved in critical aspects of protein shuttling to the plasma membrane and likely are involved in clustering of sodium channels at nodes of Ranvier. Mutations in $Na_V$ β-subunits have been linked to epilepsy, long QT syndrome, and neuropathic pain, and present a likely future target of pharmacological modulation (Isom, Neuroscientist 2001, 7, 42-54 and references therein; Tseng et al., J. Mol. Microbiol. Biotechnol. 2007, 12, 249-62).

Regulation and Trafficking of $Na_V$

The trafficking of sodium channels and their expression at the cell membrane is a tightly controlled process dependent on association with multiple proteins through protein-protein interactions (Cusdin et al., Traffic 2008, 9, 17-26). The full arsenal of proteins responsible for this process has not been elucidated, however association with β-subunits and with other trafficking proteins substantially increases the rate at which sodium channels are processed through the secretory pathway. In neurons, sodium channels covalently associate with β2-subunits in a post-Golgi compartment and are shuttled to the cell membrane. About 70% of sodium channels lack an associated β2-subunit, and these uncomplexed α-subunits are located primarily in the cytoplasm; complexation and trafficking are likely the rate limiting steps for expression at the plasma membrane (Schmidt et al., *Cell* 1986, 46, 437-444). Association with contactin, a glycosoyl-phosphatidylinositol-anchored CAM protein, also facilitates expression at the plasma membrane (Liu et al., *J. Biol. Chem.* 2001, 276, 46553-46561; Shah et al., *J. Neurosci.* 2004, 24, 7387-7399; Kazarinova-Noyes et al., *J. Neurosci.* 2001, 21, 7517-7525).

Proper localization of all of the components of neuronal signaling, including sodium channels, potassium channels, and $Na^+/K^+$-ATPase is of crucial importance in myelinated neurons. Two regions of the neuron are particularly important with respect to signaling: the nodes of Ranvier and the axon initial segment (AIS, also called the axon hillock). Nodes of Ranvier contain very high concentrations of sodium channels, with densities up to 12,000 channels/$\mu m^2$ reported, and 700,000 channels at a single node (Ritchie et al., *Proc. Natl. Acad. Sci. U.S.A.* 1977, 74, 211-215). Conversely, the regions of membrane that contact myelin contain no more than 25 channels/$\mu m^2$. This arrangement of $Na_V$ channels is central to saltatory conduction (Ritchie et al., *Proc. Natl. Acad. Sci. U.S.A.* 1977, 74, 211-215).

Localization of $Na_V$ channels at nodes of Ranvier and at the AIS is a tightly controlled process that involves three basic components: regulated export of channels from the ER; uniform expression at the cell membrane with selective localized retention; and regulated endocytosis. Many of the same processes that control clustering at nodes of Ranvier are operative at the AIS. The primary $Na_V$ isoforms expressed at these two locations are $Na_V1.2$ and $Na_V1.6$. These sodium channel isoforms are initially inserted uniformly into the plasma membrane, where they freely diffuse (Gamido et al., *Biol. Cell* 2003, 95, 437-445). Diffusion at nodes of Ranvier and at the AIS, however, is tightly restricted, and ankyrin$_G$ and spectrin βIV proteins are believed to anchor sodium channels at these locations. Both of these proteins are known to associate with the cell's underlying actin cytoskeleton (Bennett et al., *Physiol. Rev.* 2001, 81, 1353-1392).

The myelin sheath itself plays a pivotal role in $Na_V$ regulation and clustering. Clusters of $Na_V$ channels begin to develop immediately after glial cells attach themselves to axons, and these clusters appear to translocate along the length of the axon as the myelinating glial cell grows (Dugandzija-Novakovic et al., *J. Neurosci.* 1995, 15, 492-503; Vabnick et al., *J. Neurosci.* 1996, 16, 4914-4922; Vabnick et al., *J. Neurobiol.* 1998, 37, 80-96). While both $Na_V1.2$ and 1.6 are initially expressed in neurons, as myelination occurs $Na_V1.2$ is selectively replaced at nodes of Ranvier with $Na_V1.6$ (Boiko et al., *Neuron* 2001, 30, 91-104). Neither clustering nor upregulation occur in mice that lack myelin basic protein (Koszowski et al., *J. Neurosci.* 1998, 18, 5859-5868), a protein involved in the myelination of neurons in the CNS. Finally, gliomedin, a protein secreted by Schwann cells, contains a CAM binding site and appears to concentrate at the nodal edge of Schwann cells, providing high avidity binding sites for CAMs along with their associated sodium channel β- and α-subunits (Eshed et al., *Neuron* 2005, 47, 215-229).

The rate of turnover of sodium channels in vivo is not precisely known but is believed to be on the order of 1-3 days (Ritchie, *Proc. R. Soc. London* 1988, 233, 423-430). Trafficking is a dynamic process, with delivery of $Na_V$ proteins to the plasma membrane balanced by degradation of existing proteins. Therefore, sodium channel proteins must be continuously trafficked from ribosomes in the soma, along the length of the axon, to the site of insertion in the plasma membrane. The mechanisms that govern selectivity in the process of endocytosis are not known. Nevertheless, both sustained activation of $Na_V$ (Paillart et al., *J. Cell Biol.* 1996, 134, 499-509) and elevated intracellular $Ca^{2+}$ concentration (Kobayashi et al., *Ann. N.Y. Acad. Sci.* 2002, 971, 137-134) appear to lead to increased $Na_V$ endocytosis.

In summary, the regulation, trafficking and subcellular localization of $Na_V$ relies on the association of the $Na_V$ α-subunit with one or more β-subunits, which, in combination with other trafficking proteins, control the rate of expression at the cell membrane. The proteins are distributed uniformly at the cell membrane, then selectively clustered at the AIS and at nodes of Ranvier. Understanding the rate of turnover of $Na_V$ channels and the cofactors that govern selective endocytosis represent current areas of research.

$Na_V$ Isoform Distribution

Ten different voltage-gated sodium channel isoforms have been identified and cloned, and the sequence homology between all isoforms is >50%. The biological relevance of sequence variation among different $Na_V$ isoforms and splice variants is generally attributed to three functional advantages (Caldwell et al., *Adv. Mol. Cell Biol.* 2004, 32, 15-50): each isoform possesses unique signaling characteristics which are appropriate for certain tissue types; different sequences may allow each channel to be recruited and transported by appropriate trafficking molecules; and the unique, non-coding regions may play a role in channel regulation, affecting expression. Nearly all tissues contain more than a single $Na_V$ isoform, the possible exceptions being mature skeletal muscle and cardiac muscle, which express fairly pure populations of $Na_V1.4$ and 1.5, respectively. Nevertheless, some level of tissue isoform specificity exists, and a general understanding of where each isoform is distributed has developed (Table 1).

TABLE 1

The isoform distribution of voltage-gated sodium channels (adapted from: Catterall et al., *Pharmacol. Rev.* 2005, 57, 397-409; see also references therein)

| $Na_V$ isoform | STX sensitive?[a] | Distribution |
| --- | --- | --- |
| 1.1 | Yes | Central neurons: primarily localized to cell bodies; cardiac myocytes |
| 1.2 | Yes | Central neurons: primarily localized to unmyelinated and premyelinated axons |
| 1.3 | Yes | Central neurons primarily expressed in embryonic and early prenatal life; preferentially localized in cell bodies in adult rat brain; cardiac myocytes |
| 1.4 | Yes | High levels in adult skeletal muscle and low levels in neonatal skeletal muscle |
| 1.5 | No | Cardiac myocytes, immature and denervated skeletal muscle, certain brain neurons |
| 1.6 | Yes | Somatodendritic distribution in output neurons of the cerebellum, cerebral cortex, and hippocampus; Purkinje cells in the cerebellar granule cell layer; brainstem and spinal cord, astrocytes, and Schwann cells; DRG; nodes of Ranvier of sensory and motor axons in the PNS; nodes of Ranvier in the CNS |
| 1.7 | Yes | All types of DRG neurons, sympathetic neurons, Schwann cells, and neuroendocrine cells |

TABLE 1-continued

The isoform distribution of voltage-gated sodium channels
(adapted from: Catterall et al., *Pharmacol. Rev.* 2005,
57, 397-409; see also references therein)

| $Na_V$ isoform | STX sensitive?[a] | Distribution |
|---|---|---|
| 1.8 | No | Small and medium-sized DRG neurons and their axons |
| 1.9 | No | C-type DRG neurons, trigeminal neurons and their axons; preferentially expressed in nociceptive DRG neurons |

[a]STX displays single digit nanomolar $IC_{50}$s against sensitive $Na_V$ isoforms, while insensitive isoforms are 200-5000-fold less sensitive.

Sodium channels are found in certain sensory receptors, including those for pain, taste, and sound, where they serve to amplify and transduce sensory information. Some $Na_V$ isoforms appear to have tissue specific distributions, and several isoform specific sodium channelopathies lead to tissue specific dysfunction. For example, mutations in $Na_V 1.4$ have been linked with periodic paralysis (Lehmann-Horn et al., *Physiol. Rev.* 1999, 79, 1317-1372), which is caused by a defect in $Na_V$ inactivation, resulting in channels experiencing prolonged conductance. Without intending to be bound by theory, prolonged conductance is believed to lead to a slow inactivated state, which is mechanistically distinct from fast inactivation and is poorly understood. Recovery from this state is very slow, causing the channels to remain nonconductive for extended periods of time. Individuals displaying this phenotype do not have cognitive deficits or cardiac disorders, which is consistent with a singular location of $Na_V 1.4$ within skeletal muscle. Other isoform specific channelopathies include long QT syndrome (Wang et al., *Cell* 1995, 80, 805-811) and disorders of the central nervous system, including paralysis, ataxia, and dystonia (Kohrman et al., *J. Neurosci.* 1996, 16, 5993-5999; Sprunger et al., *Hum. Mol. Genet.* 1999, 8, 471-479). Similarly, gain of function mutation in $Na_V 1.7$ has been linked to paroxysmal extreme pain disorder, a condition characterized by burning pain in the rectal, ocular or submandibular regions accompanied by skin flushing (Fertleman et al., *Neuron* 2006, 52, 767-774).

$Na_V$ and Pain

The relationship between pain perception and sodium channel expression is a highly active area of current research. The signaling mechanisms that are involved in transmitting pain sensation are closely tied to sodium channel expression (for reviews, see: Amir et al., *J. Pain* 2006, 7, Supp. 3, S1-29; Devor et al., *J. Pain* 2006, 7, Supp. 1, S3-S12; Cummins et al., *Pain* 2007, 131, 243-57). Central to pain signaling is the ability of neurons to fire repetitive bursts of action potentials. In chronic pain conditions, signaling occurs as a result of a reorganization of the components that integrate and send signals both in the central and peripheral nervous system (Devor et al., *J. Pain* 2006, 7, Supp. 1, S3-S12). At least three separate processes that involve $Na_V$ define this reorganization: changes in gene expression; changes in trafficking and accumulation of $Na_V$; and altered $Na_V$ kinetics.

Recent studies have focused on the contribution of individual sodium channel isoforms to pain perception. Four sodium channel isoforms ($Na_V 1.3$, 1.7, 1.8 and 1.9) have displayed altered expression profiles in studies of chronic pain, and a variety of genetic and small molecule (Hoyt et al., *Bioorg. Med. Chem. Lett.* 2007, 17, 4630-4634; Jarvis et al., *Proc. Natl. Acad. Sci. U.S.A.* 2007, 104, 8520-8525) interventions have continued to probe their contributions (for a recent review, see: Krafte et al., *Curr. Opin. Pharmacol.* 2008, 8, 50-56).

Peripheral nerve injury is known to cause upregulation of $Na_V 1.3$. A recent study utilized genetic knockdown to examine if this channel isoform contributes to development and maintenance of chronic pain. In spared nerve injury and nerve axotomy rat pain models, upregulation of $Na_V 1.3$ was observed, however genetic knockdown of $Na_V 1.3$ after injury did not alleviate behaviors associated with hypersensitivity (Lindia et al., *Pain* 2005, 117, 145-153).

Congenital indifference to pain is a rare inherited condition in which patients have a severely decreased ability to sense pain, while maintaining otherwise normal sensory and motor function. Two studies of families expressing this phenotype showed a series of loss-of-function mutations in the SCN9A gene, which encodes for $Na_V 1.7$ (Goldberg et al., *Clin. Genet.* 2007, 71, 311-319; Ahmad et al., *Hum. Mol. Genet.* 2007, 16, 2114-2121). Following up on this result, Wood and co-workers generated global $Na_V 1.7$-null mice, however these animals died shortly after birth. The difference in phenotype between mice and humans is attributed to species-specific variation in channel distribution. The authors therefore utilized the technique of nociceptor-specific gene ablation in which $Na_V 1.7$ was knocked out selectively in nociceptors (Nassar et al., *Proc. Natl. Acad. Sci. U.S.A.* 2004, 101, 12706-12711). These animals exhibited increased mechanical and thermal pain thresholds, and almost complete ablation of response to inflammatory pain.

$Na_V 1.8$ has been an important target for both genetic and small molecule studies since it is expressed preferentially in peripheral sensory neurons. Genetic knockout of $Na_V 1.8$ in mice produced viable, fertile and apparently normal animals. Consistent with $Na_V 1.8$'s role in nociception, these mice showed significantly decreased response to noxious mechanical stimuli and some types of inflammatory pain (Akopian et al., *Nature Neurosci.* 1999, 2, 541-549; Laird et al., *J. Neurosci.* 2002, 22, 8352-8356), however they did not display behavioral changes in neuropathic pain (Kerr et al., *NeuroReport* 2001, 12, 3077-3080). Isolation of sensory neurons in these animals showed increased current densities of TTX-sensitive channels, which suggests that a compensatory mechanism causes upregulation of other $Na_V$ isoforms. Contrasting these results, genetic knockdown of $Na_V 1.8$ in a rat model of neuropathic pain by antisense oligodeoxynucleotides resulted in a reversal of neuropathic pain induced by spinal nerve injury without affecting normal sensory response (Lai et al., *Pain* 2002, 95, 143-152). More recently, siRNA was used to selectively knock down $Na_V 1.8$ expression in rats displaying mechanical allodynia due to chronic constriction nerve injury (Dong et al., *Neuroscience* 2007, 146, 812-821). These rats displayed robust reversal of mechanical allodynia, and knockdown of $Na_V 1.8$ in vivo was confirmed by measuring $Na_V 1.8$ mRNA expression.

$Na_V 1.9$ is also expressed preferentially in nociceptors of the peripheral nervous system, and $Na_V 1.9$ null mutant nice have been utilized in models of mechanical, thermal and inflammatory pain. In one study these animals were found to be viable but did not show mechanical or thermal hypersensitivity after nerve injury or inflammation (Priest et al., *Proc. Nat. Acad. Sci. U.S.A.* 2005, 102, 9382-9387). In a second study, administration of prostaglandin $E_2$, bradykinin, interleukin-1β, capsaicin, and $P2X_3$ and P2Y, agents known to elicit an inflammatory response, $Na_V 1.9$ null mutant mice showed decreased pain hypersensitivity, while normal thermal and mechanical pain responses were unchanged (Amaya et al., *J. Neurosci.* 2006, 26, 12852-12860). Collectively, these studies suggest that $Na_V 1.9$ plays a role in inflammation-induced hypersensitivity of peripheral nerves.

Taken together, genetic knockdown and knockout studies indicate an important role for several sodium channel isoforms in pain signaling. Isoform signature appears to vary with the different types of pain (i.e. inflammatory vs. neuropathic). While these studies implicate certain channel isoforms in the pain response cycle, they are not instructive in terms of the precise trafficking events that must take place when a neuron's signaling characteristics are altered. All of the $Na_V$ isoforms that have been implicated in chronic pain are also present before injury. An understanding of the precise regulatory, trafficking and reorganization events that lead to altered neuronal signaling would offer mechanistic insight into pain development.

Fluorescence Techniques for Visualizing $Na_V$

Interest in the relationship between $Na_V$ and neuronal excitability has led to the development of fluorescence techniques for visualizing sodium channel proteins. A singular example of an $Na_V$-GFP fusion protein was reported in 2002. The c-terminus of the human heart sodium channel (hH1) was labeled with GFP and this construct was successfully transfected into HEK293 cells, displaying identical electrophysiological properties to the wild type protein (Zimmer et al., *J. Membr. Biol.* 2002, 186, 1-12). Examination of the heterologously expressed fusion protein by confocal microscopy revealed high levels of expression in several intracellular membranes, particularly within the endoplasmic reticulum (ER). It was proposed that the ER may serve as a reservoir for cardiac sodium channels, and that transport out of the ER may be the rate-limiting step to expression at the cell membrane.

Antibodies specific for each of the nine $Na_V$ isoforms have been developed, and these tools have helped to further elucidate the distribution of $Na_V$ isoforms in various types of tissues, and at specific locations within a given axon. For example, Levinson and coworkers have shown through isoform specific labeling of fixed nerve tissue that $Na_V$ 1.6 is expressed preferentially at nodes of Ranvier in both sensory and motor axons in the peripheral nervous system, and at nodes of Ranvier in the CNS (Caldwell et al., *Proc. Nat. Acad. Sci. U.S.A.* 2000, 97, 5616-5620).

Several other studies out of the Levinson lab have shown altered sodium channel isoform distribution in developing neurons (Kaplan et al., *Neuron* 2001, 30, 105-119) and in neurons displaying myelination disease states (Ulzheimer et al., *Mol. Cell. Neurosci.* 2004, 25, 83-94). More recently, Levinson and coworkers have used wisdom tooth dental pulp (Henry et al., *J. Pain* 2009, 10, 750-758) to study the correlation between pain prior to tooth extraction and expression of $Na_V$1.7 (Luo et al., *Mol. Pain* 2008, 4, 16-39) and 1.8 (Henry et al., *Neurosci. Lett.* 2005, 380, 32-36). Finally, Levinson has shown differences in $Na_V$1.2 and $Na_V$1.6 at axon initial segments in myelinated vs. non-myelinated axons (Boiko et al., *J. Neurosci.* 2003, 23, 2306-2313). Taken together, these studies show the power of fluorescence techniques and immunohistology in understanding $Na_V$ regulation and distribution. The ability to perform similar experiments in live organisms would allow for observation of the dynamic processes involved in $Na_V$ trafficking, and such is the motivation for development of additional tools for labeling these channels.

In summary, our understanding of the structural mechanics involved in sodium channel molecular function has continued to evolve over the past 15 years, even in the absence of X-ray crystallographic information. Techniques as diverse as synthesis, NMR and protein mutagenesis continue to illuminate the precise structural elements by which nature has designed this exquisitely selective machine for passing ions through the cell membrane.

Regulation, trafficking and localization of $Na_V$ represent vital processes that control the electronic properties of excitable cells. The precise regulatory mechanisms involved in maintaining these processes are not fully understood, however current efforts utilizing immunohistology as a means of visualizing channel expression at the plasma membrane have illuminated distinct changes in expression profiles of individual $Na_V$ isoforms in various pain states.

The challenge of visualizing changes in sodium channel expression in live tissue remains a complex problem with much promise in the potential to illuminate fundamental mechanisms of neuronal excitability. Selective blockade of aberrant sodium current likewise represents a possible solution to diseases of hyperexcitability. Within this context, the development of high affinity small molecule modulators of $Na_V$ activity could provide a fruitful approach to augmenting our understanding of both of these processes.

Compounds

According to one aspect of the invention, novel compounds relating to batrachotoxin are provided. The structures of the compounds may be represented by the general formula (I):

$$\text{(I)}$$

or a pharmaceutically acceptable salt, stereoisomer or prodrug thereof, wherein:

$R_1$ is hydrogen, alkyl, alkenyl, alkynyl, aryl, aralkyl, heteroaryl, heteroaralkyl, cycloalkyl, cycloalkenyl, cycloalkylalkyl, heterocyclyl, heterocyclylalkyl, —C(O)R, or a protecting group, and is optionally substituted with 1 to 3 A groups;

$R_2$ is hydrogen, alkyl, alkenyl, alkynyl, aryl, aralkyl, heteroaryl, heteroaralkyl, cycloalkyl, cycloalkenyl, cycloalkylalkyl, heterocyclyl, heterocyclylalkyl, —C(O)R, or a protecting group, and is optionally substituted with 1 to 3 A groups;

$R_3$ is hydrogen, alkyl, alkenyl, alkynyl, aryl, aralkyl, heteroaryl, heteroaralkyl, cycloalkyl, cycloalkenyl, cycloalkylalkyl, heterocyclyl, heterocyclylalkyl, —C(O)R, or a protecting group, and is optionally substituted with 1 to 3 A groups;

X is O, S, or $$\begin{array}{c}\diagdown\phantom{xx}\diagup\\ \diagup\phantom{xx}\diagdown\\ R_4 \phantom{xxx} R_5;\end{array}$$

$R_4$, $R_5$, $R_6$, and $R_7$ are independently hydrogen, alkyl, alkenyl, alkynyl, alkoxy, alkylamino, aryl, aryloxy, arylamino, aralkyl, aralkoxy, aralkamino, heteroaryl, heteroaryloxy, heteroarylamino, heteroaralkyl, heteroaralkoxy, heteroaralkamino, cycloalkyl, cycloalkenyl, cycloalkylalkyl, cycloalkoxy, cycloalkamino, heterocyclyl, heterocyclyloxy, heterocyclylamino, heterocyclylalkyl, heterocyclylalkoxy, heterocyclylalkamino, silyl, sulfonyl, hydroxyl, thio, amino, alkanoylamino, aroylamino, aralkanoylamino, alkylcarboxy, carbonate, carbamate, guanidinyl, urea, halo, trihalomethyl, cyano, nitro, phosphoryl, sulfonyl, sulfonamindo, or azido, and are optionally substituted with 1 to 3 A groups;

$R_8$ is hydrogen, alkyl, alkenyl, alkynyl, alkoxy, aryl, aralkyl, heteroaryl, heteroaralkyl, cycloalkyl, cycloalkenyl, cycloalkylalkyl, heterocyclyl, or heterocyclylalkyl, and is optionally substituted with 1 to 3 A groups;

each R is independently hydrogen, alkyl, alkenyl, alkynyl, alkoxy, alkylamino, aryl, aryloxy, arylamino, aralkyl, aralkoxy, aralkamino, heteroaryl, heteroaryloxy, heteroarylamino, heteroaralkyl, heteroaralkoxy, heteroaralkamino, cycloalkyl, cycloalkenyl, cycloalkylalkyl, cycloalkoxy, cycloalkamino, heterocyclyl, heterocyclyloxy, heterocyclylamino, heterocyclylalkyl, heterocyclylalkoxy, or heterocyclylalkamino, and is optionally substituted with 1 to 3 A groups; and each A is independently alkyl, alkenyl, alkynyl, alkoxy, alkanoyl, alkylamino, aryl, aryloxy, arylamino, aralkyl, aralkoxy, aralkanoyl, aralkamino, heteroaryl, heteroaryloxy, heteroarylamino, heteroaralkyl, heteroaralkoxy, heteroaralkanoyl, heteroaralkamino, cycloalkyl, cycloalkenyl, cycloalkylalkyl, cycloalkoxy, cycloalkanoyl, cycloalkamino, heterocyclyl, heterocyclyloxy, heterocyclylamino, heterocyclylalkyl, heterocyclylalkoxy, heterocyclylalkanoyl, heterocyclylalkamino, hydroxyl, thio, amino, alkanoylamino, aroylamino, aralkanoylamino, alkylcarboxy, carbonate, carbamate, guanidinyl, urea, halo, trihalomethyl, cyano, nitro, phosphoryl, sulfonyl, sulfonamido, or azido.

As used herein, the term "alkyl" refers to the radical of saturated aliphatic groups, including straight-chain alkyl groups, branched-chain alkyl groups, cycloalkyl (alicyclic) groups, alkyl-substituted cycloalkyl groups, and cycloalkyl-substituted alkyl groups. In some embodiments, a straight chain or branched chain alkyl has 30 or fewer carbon atoms in its backbone (e.g., $C_1$-$C_{30}$ for straight chains, $C_3$-$C_{30}$ for branched chains), and more specifically 20 or fewer. Likewise, some cycloalkyls have from 3-10 carbon atoms in their ring structure, and more specifically have 5, 6 or 7 carbons in the ring structure.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, a halo, a hydroxyl, a carbonyl (such as a keto, a carboxy, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a thio, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

As used herein, the term "alkoxy" refers to an alkyl group, in certain specific embodiments, a lower alkyl group, having an oxygen attached thereto. Representative alkoxy groups include methoxy, ethoxy, propoxy, t-butoxy, and the like.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed above, except where stability is prohibitive. For example, substitution of alkenyl groups by one or more alkyl, cycloalkyl, heterocyclyl, aryl, or heteroaryl groups is contemplated.

The term "$C_{x-y}$" when used in conjunction with a chemical moiety, such as acyl, acyloxy, alkyl, alkenyl, alkynyl, or alkoxy, is meant to include groups that contain from x to y carbons in the chain. For example, the term "$C_{x-y}$-alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-trifluoroethyl, etc. "$C_0$-alkyl" indicates a hydrogen where the group is in a terminal position, or is a bond if internal. The terms "$C_{2-y}$-alkenyl" and "$C_{2-y}$-alkynyl" refer to substituted or unsubstituted unsaturated aliphatic groups analogous in length and possible substitution to the alkyls described above, but that contain at least one double or triple bond, respectively.

The term "alkylamino", as used herein, refers to an amino group substituted with at least one alkyl group.

The term "alkylthio", as used herein, refers to a thiol group substituted with an alkyl group and may be represented by the general formula alkyl-S—.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, cycloalkyl, heterocyclyl, aryl, or heteroaryl groups is contemplated.

The term "amide", as used herein, refers to a group

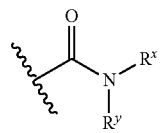

wherein $R^x$ and $R^y$ each independently represent a hydrogen or hydrocarbyl group, or $R^x$ and $R^y$ taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

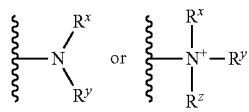

wherein $R^x$, $R^y$, and $R^z$ each independently represent a hydrogen or a hydrocarbyl group, or $R^x$ and $R^y$ taken together with the N atom to which they are attached complete a heterocycle having from 4 to 8 atoms in the ring structure.

The term "aminoalkyl", as used herein, refers to an alkyl group substituted with an amino group.

The term "aralkyl", as used herein, refers to an alkyl group substituted with an aryl group.

The term "aryl" as used herein includes substituted or unsubstituted single-ring aromatic groups in which each atom of the ring is carbon. In certain embodiments, the ring is a 5- to 7-membered ring, and in more specific embodiments is a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "carbamate" is art-recognized and refers to a group

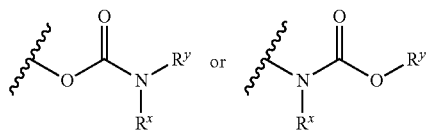

wherein $R^x$ and $R^y$ independently represent hydrogen or a hydrocarbyl group, or $R^x$ and $R^y$ taken together with the atoms to which they are attached complete a heterocycle having from 4 to 8 atoms in the ring structure.

The term "cycloalkyl", as used herein, refers to a non-aromatic saturated or unsaturated ring in which each atom of the ring is carbon. In certain embodiments, a cycloalkyl ring contains from 3 to 10 atoms, and in more specific embodiments from 5 to 7 atoms.

The term "carbonate" is art-recognized and refers to a group $—OCO_2—R^x$, wherein $R^x$ represents a hydrocarbyl group.

The term "carboxy", as used herein, refers to a group represented by the formula $—CO_2H$.

The term "ester", as used herein, refers to a group $—C(O)OR^x$ wherein $R^x$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The term "guanidinyl" is art-recognized and may be represented by the general formula

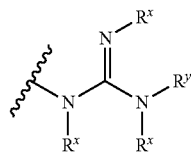

wherein $R^x$ and $R^y$ independently represent hydrogen or a hydrocarbyl.

The terms "halo" and "halogen" as used herein mean halogen and include chloro, fluoro, bromo, and iodo.

The terms "hetaralkyl" and "heteroaralkyl", as used herein, refer to an alkyl group substituted with a hetaryl group.

The terms "heteroaryl" and "hetaryl" include substituted or unsubstituted aromatic single ring structures, in certain specific embodiments 5- to 7-membered rings, more specifically 5- to 6-membered rings, whose ring structures include at least one heteroatom, in some embodiments one to four heteroatoms, and in more specific embodiments one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Typical heteroatoms are nitrogen, oxygen, and sulfur.

The terms "heterocyclyl", "heterocycle", and "heterocyclic" refer to substituted or unsubstituted non-aromatic ring structures, in certain specific embodiments 3- to 10-membered rings, more specifically 3- to 7-membered rings, whose ring structures include at least one heteroatom, in some embodiments one to four heteroatoms, and in more specific embodiments one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "heterocyclylalkyl", as used herein, refers to an alkyl group substituted with a heterocycle group.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes herein, but substituents such as acetyl (which has a =O substituent on the linking carbon) and ethoxy (which is linked through oxygen, not carbon) are not. Hydrocarbyl groups include, but are not limited to, aryl, heteroaryl, carbocycle, heterocycle, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer non-hydrogen atoms in the substituent, and in certain embodiments, six or fewer. A "lower alkyl", for example, refers to an alkyl group that contains ten or fewer carbon atoms, and in specific embodiments six or fewer carbon atoms. In certain embodiments, the acyl, acyloxy, alkyl, alkenyl, alkynyl, and alkoxy substituents defined herein are respectively lower acyl, lower acyloxy, lower alkyl, lower alkenyl, lower alkynyl, and lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, more specifically from 5 to 7.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc., under conditions in which the compound is to be used. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents may include any substituents described herein, for example, a halogen, a hydroxyl, a carbonyl (such as a keto, a carboxy, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain may themselves be substituted, if appropriate.

Unless specifically described as "unsubstituted", references to chemical moieties herein are understood to include substituted variants. For example, reference to an "aryl" group or moiety implicitly includes both substituted and unsubstituted variants.

The term "sulfate" is art-recognized and refers to the group —OSO$_3$H, or a pharmaceutically acceptable salt thereof.

The term "sulfonamide" is art-recognized and refers to the group represented by the general formulae

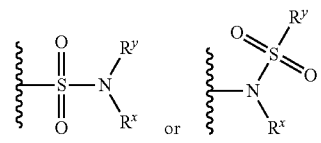

wherein R$^x$ and R$^y$ independently represent hydrogen or hydrocarbyl.

The term "sulfoxide" is art-recognized and refers to the group —S(O)—R$^x$, wherein R$^x$ represents a hydrocarbyl.

The term "sulfonate" is art-recognized and refers to the group —SO$_3$H, or a pharmaceutically acceptable salt thereof.

The term "sulfone" is art-recognized and refers to the group —S(O)$_2$—R$^x$, wherein R$^x$ represents a hydrocarbyl.

The term "thioalkyl", as used herein, refers to an alkyl group substituted with a thiol group.

The term "thioester", as used herein, refers to a group —C(O)SR$^x$ or —SC(O)R$^x$ wherein R$^x$ represents a hydrocarbyl.

The term "thioether", as used herein, is equivalent to an ether, wherein the oxygen is replaced with a sulfur.

The term "urea" is art-recognized and may be represented by the general formula

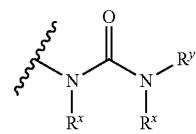

wherein R$^x$ and R$^y$ independently represent hydrogen or a hydrocarbyl.

According to some embodiments of the invention, in compounds of structural formula (I), R$_1$ is hydrogen, alkyl, —C(O)R, or a protecting group, and is optionally substituted with 1 to 3 A groups.

In some embodiments of the invention, the R$_1$ group is hydrogen, alkyl, or a protecting group. In preferred embodiments of the invention, the R$_1$ group is methoxymethyl.

One of ordinary skill in the art would understand that a protecting group is reversibly attached to a desired position of the molecule to control the reaction of other agents at that position. Protecting groups useful in the practice of the instant invention are well known in the art. See, for example, "Greene's Protective Groups in Organic Synthesis, 4$^{th}$ edition", by P. G. M. Wuts and T. W. Greene (Wiley-Interscience, 2006); and "Protecting Groups", by P. Kocienski (Thieme, 2005).

In some embodiments of the invention, the protecting group is an alcohol or amine protecting group. In some embodiments, the protecting group is an acyl group or an acetal. In preferred embodiments, the protecting group is a benzoyl group, a t-butyloxycarbonyl group, or a methoxymethyl ether.

In some embodiments of the invention, the protecting group used is a silyl protecting group.

According to some embodiments of the invention, the $R_2$ group of structural formula (I) is hydrogen, alkyl, —C(O)R, or a protecting group, and is optionally substituted with 1 to 3 A groups.

In some embodiments of the invention, $R_2$ is alkyl, and is optionally substituted with 1 to 3 A groups In preferred embodiments, $R_2$ is methyl.

In certain embodiments, the $R_3$ group is alkyl, aryl, heteroaryl, or —C(O)R, and is optionally substituted with 1 to 3 A groups.

In preferred embodiments, $R_3$ is —C(O)R, and R is alkyl, aryl, heteroaryl, arylamino, or heteroarylamino, and is optionally substituted with 1 to 3 A groups. In even more preferred embodiments, $R_3$ is —C(O)R, and R is a substituted pyrrole, such as

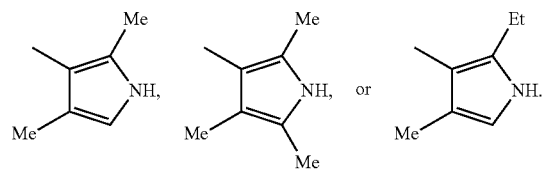

In some embodiments, $R_4$, $R_5$, $R_6$, and $R_7$ are independently hydrogen, alkyl, alkoxyl, cycloalkyl, heterocyclyl, silyl, sulfonyl, carbonate, hydroxyl, thio, amino, halo, cyano, or nitro, and are optionally substituted with 1 to 3 A groups. In specific embodiments, $R_4$, $R_5$, $R_6$, and $R_7$ are independently hydrogen, alkyl, alkoxy, silyl, or halo. In even more specific embodiments, $R_4$, $R_5$, $R_6$, and $R_7$ are hydrogen.

In certain embodiments of the invention, $R_8$ is hydrogen or alkyl. In preferred embodiments, $R_8$ is methyl.

In certain embodiments of the invention, the R group is independently alkyl, aryl, heteroaryl, arylamino, or heteroarylamino.

In preferred embodiments of the invention, X is O or

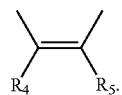

In other preferred embodiments, $R_1$ is hydrogen, —C(O)R, or a protecting group, and is optionally substituted with 1 to 3 A groups; $R_2$ is hydrogen, alkyl, —C(O)R, or a protecting group, and is optionally substituted with 1 to 3 A groups; $R_3$ is —C(O)R, and R is alkyl, aryl, heteroaryl, arylamino, or heteroarylamino, and is optionally substituted with 1 to 3 A groups; $R_4$, $R_5$, $R_6$, and $R_7$ are independently hydrogen, alkyl, alkoxyl, cycloalkyl, heterocyclyl, silyl, sulfonyl, carbonate, hydroxyl, thio, amino, halo, cyano, or nitro, and are optionally substituted with 1 to 3 A groups; $R_8$ is hydrogen or alkyl; R is alkyl; and X is O or

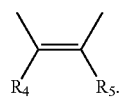

In some specific embodiments, the compound is any one of the following compounds:

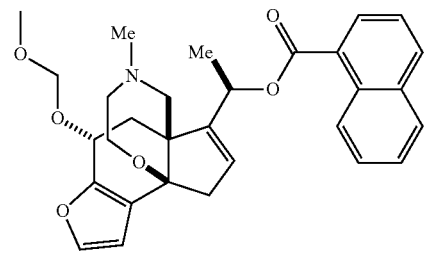

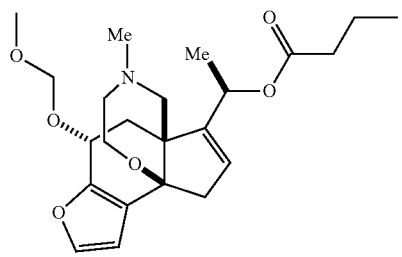

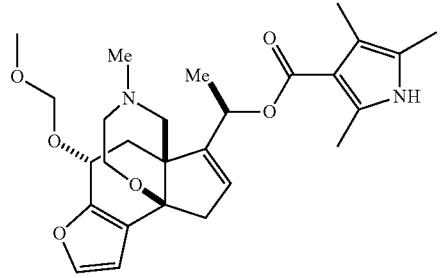

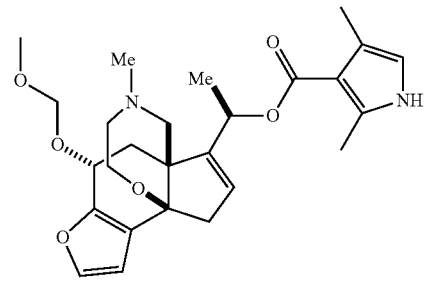

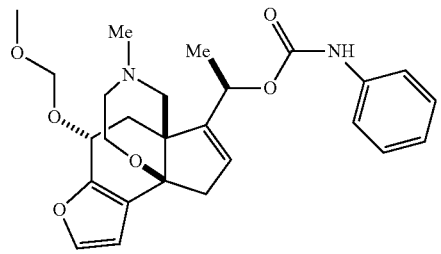

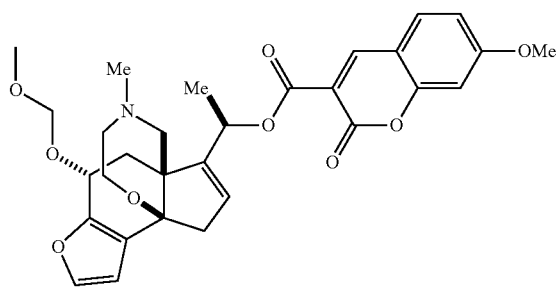

-continued

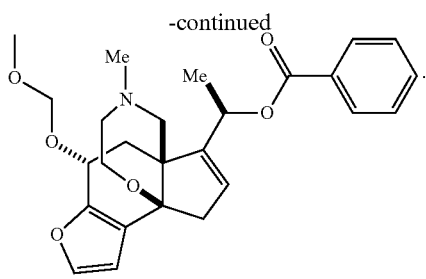

In some embodiments, the compound of the invention modulates the activity of a sodium channel. As described above, the sodium channel is a highly studied drug target, as sodium channelopathies have been associated with arrhythmia, epilepsy, neuropathic pain, and congenital analgesia. Modulation of the sodium channel activity by the compounds of the instant invention may therefore provide a therapeutic benefit to patients suffering such conditions. See, for example, Tsuchida et al., The Effect of Chinese Herbal Medicine Containing Aconitine on the Pain Relief in Interstitial Cystitis Patients—a Preliminary Study. *J. Urology* 2009, 181, 23-24, and references therein; Ameri, A. The Effects of Aconitine Alkaloids on the Central Nervous System. *Progress in Neurobiology* 1998, 56, 211-235.

In certain embodiments, the compounds of the instant invention cause the sodium channel to open. In certain embodiments, the compounds of the invention inactivate the sodium channel. In certain embodiments, the compounds of the invention decrease flow of sodium ions through the sodium channel at a specific membrane potential. Without intending to be bound by theory, these effects on the sodium channel may be responsible for the therapeutic benefits provided to patients by these compounds.

Pharmaceutical Compositions

In another aspect, the instant invention provides pharmaceutical compositions comprising a compound of the invention and a pharmaceutically acceptable carrier.

Pharmaceutically acceptable carriers are well known in the art and include, for example, aqueous solutions such as water or physiologically buffered saline or other solvents or vehicles such as glycols, glycerol, oils such as olive oil or injectable organic esters. In a specific embodiment, such pharmaceutical compositions are for human administration, the aqueous solution is pyrogen free, or substantially pyrogen free. The excipients may be chosen, for example, to effect delayed release of an agent or to selectively target one or more cells, tissues or organs. The pharmaceutical composition may be in dosage unit form such as tablet, capsule, sprinkle capsule, granule, powder, syrup, suppository, injection or the like. The composition may also be present in a transdermal delivery system, e.g., a skin patch.

A pharmaceutically acceptable carrier may contain physiologically acceptable agents that act, for example, to stabilize or to increase the absorption of a compound of the instant invention. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The pharmaceutical composition also may comprise a liposome or other polymer matrix, which may have incorporated therein, for example, a compound of the invention. Liposomes, for example, which consist of phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition, or vehicle, such as a liquid or solid filler, diluent, excipient, solvent, or encapsulating material, involved in carrying or transporting the subject compounds from one organ, or portion of the body, to another organ, or portion of the body. Each carrier must be "acceptable" in the sense of being compatible with the other ingredients of the formulation and not injurious to the patient. Some examples of materials that can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations. See Remington The Science and Practice of Pharmacy, 20th ed. (Alfonso R. Gennaro ed.), 2000.

A pharmaceutical composition containing a compound of the instant invention may be administered to a subject by any of a number of routes of administration including, for example, orally (for example, drenches as in aqueous or non-aqueous solutions or suspensions, tablets, boluses, powders, granules, pastes for application to the tongue); sublingually; anally, rectally, or vaginally (for example, as a pessary, cream, or foam); parenterally (including intramuscularly, intravenously, subcutaneously, or intrathecally as, for example, a sterile solution or suspension); nasally; intraperitoneally; subcutaneously; transdermally (for example as a patch applied to the skin); or topically (for example, as a cream, ointment or spray applied to the skin). The compound may also be formulated for inhalation. In certain embodiments, a compound of the instant invention may be simply dissolved or suspended in sterile water. Details of appropriate routes of administration and compositions suitable for same can be found in, for example, U.S. Pat. Nos. 6,110,973; 5,763,493; 5,731,000; 5,541,231; 5,427,798; 5,358,970; and 4,172,896, as well as in patents cited therein.

The formulations of the present invention may conveniently be presented in unit dosage form and may be prepared by any methods well known in the art of pharmacy. The amount of active ingredient that can be combined with a carrier material to produce a single dosage form will vary depending upon the subject being treated and the particular mode of administration. The amount of active ingredient that can be combined with a carrier material to produce a single dosage form will generally be that amount of the compound that produces a therapeutic effect. Generally, out of one hundred percent, this amount will range from about 1 percent to about 99 percent of active ingredient, in some embodiments from about 5 percent to about 70 percent, and in more specific embodiments from about 10 percent to about 30 percent. For example, compounds of the present disclosure can be formulated in a unit dose form between about 1 µg to 10 mg for treating pain. In some embodiments, compounds or compositions of the present disclosure can be formulated in a unit dose of about 1 µg to 20 µg, of about 20 µg to 1 mg, of about 1 mg to 10 mg, of about 10 mg to 100 mg, and of about 50 mg to 500 mg. In particular, an embodiment including a compound can be formulated in 0.1 µg, 0.2 µg, 0.5 µg, 1 µg, 20 µg, 50 µg, 100 µg, 200 µg, 500 µg, 1 mg, 2 mg, 5 mg, 10 mg, 20 mg, 50 mg, 100 mg, 200 mg, and 500 mg unit dose form.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary, or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that may be used include polymeric substances and waxes. The active ingredient may also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions may also include adjuvants such as wetting agents, emulsifying and suspending agents, sweetening, flavoring, coloring, perfuming, and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Formulations of the pharmaceutical compositions of the invention for rectal, vaginal, or urethral administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Alternatively or additionally, compositions may be formulated for delivery via a catheter, stent, wire, or other intraluminal device. Delivery via such devices may be especially useful for delivery to the bladder, urethra, ureter, rectum, or intestine.

Formulations of the present invention which are suitable for vaginal administration also include pessaries, tampons, creams, gels, pastes, foams, or spray formulations containing such carriers as are known in the art to be appropriate.

Dosage forms for the topical or transdermal administration of a compound of this invention include powders, sprays, ointments, pastes, creams, lotions, gels, solutions, patches, and inhalants. The active compound may be mixed under sterile conditions with a pharmaceutically acceptable carrier, and with any preservatives, buffers, or propellants that may be required.

The ointments, pastes, creams, and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays may contain, in addition to a compound of this invention, excipients such as lactose, talc, silicic acid, aluminum hydroxide, calcium silicates, and polyamide powder, or mixtures of these substances. Sprays may additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms may be made by dissolving or dispersing the compound in the proper medium. Absorption enhancers may also be used to increase the flux of the compound across the skin. The rate of such flux may be controlled by either providing a rate controlling membrane or dispersing the compound in a polymer matrix or gel.

Formulations suitable for transdermal delivery of the instant compounds may include, for example, a vehicle that modulates transdermal permeation of the compound. In some embodiments, for example, the vehicle may be an organic solvent. In some embodiments, the vehicle may be an emulsion. In specific embodiments, the organic solvent may be an alcohol, such as, for example, ethanol, or may be dimethyl sulfoxide. In preferred embodiments, the organic solvent is ethanol. In other preferred embodiments, the organic solvent is dimethyl sulfoxide. In some preferred embodiments, the emulsion is a cream. For example, a eutectic mixture of local anesthetics ("EMLA") is a numbing cream that may be placed on skin to provide pain relief to a patient. Such a cream, either with or without local anesthetics, may be used as a vehicle to modulate the transdermal permeation of the compounds of the instant disclosure and thus to provide pain relief to a patient.

Ophthalmic formulations, eye ointments, powders, solutions, and the like, are also contemplated as being within the scope of this invention.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, and intrasternal injection and infusion.

Pharmaceutical compositions of this invention suitable for parenteral administration comprise one or more compounds of the invention in combination with one or more pharmaceutically acceptable sterile isotonic aqueous or nonaqueous solutions, dispersions, suspensions, or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity may be maintained, for example, by the use of coating materials, such as lecithin, by the maintenance of the required particle size in the case of dispersions, and by the use of surfactants.

These compositions may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, chelators and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsuled matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions that are compatible with body tissue.

Methods of introduction may also be provided by rechargeable or biodegradable devices. Various slow release polymeric devices have been developed and tested in vivo in recent years for the controlled delivery of drugs. A variety of biocompatible polymers (including hydrogels), including both biodegradable and non-degradable polymers, may be used to form an implant for the sustained release of a compound at a particular target site.

Methods of Treatment

The subject compounds and pharmaceutical compositions thereof are useful in the treatment of a subject, wherein the treatment reduces neuronal activity in the subject or brings about muscular relaxation in the subject.

Furthermore, the subject compounds and pharmaceutical compositions thereof are useful in the treatment of a subject suffering from a voltage-gated sodium channel-enhanced ailment. Examples of voltage-gated sodium channel-enhanced ailments usefully treated according to the methods of the instant invention include acute pain, anal fissures, arthritis, back pain, chronic pain, dental pain, fibromyalgia, joint pain, migraine headaches, neck pain, neuropathic pain, obstetric pain, post-herpetic neuralgia, post-operative pain, shingles, tension headaches or trigeminal neuralgia, cancer, cardiac arrythmia, epilepsy, focal dystonia, hyperhidrosis, muscle spasms, and urinary bladder relaxation.

The subject compounds and pharmaceutical compositions thereof are particular useful in the treatment of a subject suffering from pain. Examples of pain that may be usefully treated according to the methods of the instant invention include acute pain, anal fissure pain, arthritis pain, back pain, cancer pain, chronic pain, dental pain, fibromyalgia pain, joint pain, migraine headache pain, neck pain, visceral pain, neuropathic pain, obstetric pain, post-herpetic neuralgia pain, post-operative pain, sympathetically maintained pain, shingles pain, tension headache pain, trigeminal neuralgia pain, myositis pain, musculoskeletal pain, lower back pain, pain from sprains and strains, pain associated with functional bowel disorders such as non-ulcer dyspepsia, non-cardiac chest pain and irritable bowel syndrome, pain associated with myocardial ischemia, toothache pain, and pain from dysmenorrhea.

The subject compounds and pharmaceutical compositions thereof are additionally useful in the treatment of a subject, wherein the treatment reduces or eliminates wrinkles.

The compounds of the present disclosure and the pharmaceutical compositions comprising the same can be administered to a subject in one or more doses. In one embodiment, the compound or composition can be administered in an amount of about 1 µg to 10 mg per dose, e.g., about 1 µg to 5 µg, about 5 µg to 10 µg, about 10 µg to 50 µg, about 50 µg to 100 µg, about 100 µg to 200 µg, about 200 µg to 400 µg, about 400 µg to 800 µg, about 800 µg to 1 mg, about 1 mg to 2 mg, about 2 mg to 3 mg, about 3 mg to 4 mg, about 4 mg to 5 mg, about 5 mg to 6 mg, about 6 mg to 7 mg, about 7 mg to 8 mg, about 8 mg to 9 mg, or about 9 mg to 10 mg per dose.

In another embodiment, the amount of the compound or composition per dose is determined on a per body weight basis. For example, the amount of the compound or composition per dose, as determined on a per body weight basis, may be, for example, about 10 ng/kg, about 15 ng/kg, about 20 ng/kg, about 50 ng/kg, about 100 ng/kg, about 200 ng/kg, about 500 ng/kg, about 1 µg/kg, about 2 µg/kg, about 5 µg/kg, about 10 µg/kg, about 20 µg/kg, about 50 µg/kg, about 100 µg/kg, about 200 µg/kg, about 500 µg/kg, about 1 mg/kg, about 2 mg/kg, or about 5 mg/kg.

For example, in an embodiment, the compound or composition can be administered in an amount of about 15 ng/kg to 150 µg/kg, e.g., about 15 ng/kg to 30 ng/kg, about 30 ng/kg to 60 ng/kg, about 60 mg/kg to 120 ng/kg, about 120 ng/kg to 240 ng/kg, about 240 ng/kg to 480 ng/kg, about 480 ng/kg to 700 ng/kg, about 700 mg/kg to 1 µg/kg, about 1 mg/kg to 2 mg/kg, about 2 mg/kg to 4 mg/kg, about 4 mg/kg to 8 mg/kg, about 8 mg/kg to 15 mg/kg, about 15 mg/kg to 20 µg/kg, about 20 µg/kg to 30 mg/kg, about 30 µg/kg to 40 mg/kg, about 40 µg/kg to 60 µg/kg, about 60 mg/kg to 90 mg/kg, or about 90 µg/kg to 120 mg/kg, or more than about 120 µg/kg.

Those of skill will readily appreciate that dose levels can vary as a function of the specific compound or composition administered, the severity of the symptoms and the susceptibility of the subject to side effects. Preferred dosages for a given compound are readily determinable by those of skill in the art by a variety of means.

In an embodiment, multiple doses of the compound or composition are administered. The frequency of administration of the compound or composition can vary depending on any of a variety of factors, e.g., severity of the symptoms, and the like. For example, in an embodiment, the compound or composition is administered once per month, twice per month, three times per month, every other week (qow), once per week (qw), twice per week (biw), three times per week (tiw), four times per week, five times per week, six times per week, every other day (qod), daily (qd), twice a day (bid), or three times a day (tid). As discussed above, in an embodiment, the compound or composition is administered continuously.

The duration of administration of the compound or composition, e.g., the period of time over which the compound or composition is administered, can vary, depending on any of a variety of factors, e.g., patient response, etc. For example, the compound or composition can be administered over a period of time of about one day to one week, about two weeks to four weeks, about one month to two months, about two months to four months, about four months to six months, about six months to eight months, about eight months to 1 year, about 1 year to 2 years, or about 2 years to 4 years, or more.

It will be readily apparent to one of ordinary skill in the relevant arts that other suitable modifications and adaptations to the methods and applications described herein may be made without departing from the scope of the invention or any embodiment thereof. Having now described the present invention in detail, the same will be more clearly understood by reference to the following Examples, which are included herewith for purposes of illustration only and are not intended to be limiting of the invention.

EXAMPLES

Example 1

Modular Synthesis of the Pentacyclic Core of Batrachotoxin and Select Batrachotoxin Analogue Designs Batrachotoxin and related compounds, such as aconitine and grayanotoxin, are potent neurotoxins that modify the electronic properties of voltage-gated sodium channels ($Na_V$) in excitable cells. Although these toxins are believed to act at a common receptor (site II) located in the intracellular region of the sodium channel (Catterall, *Neuron* 2000, 26, 13-25), each displays a unique pharmacological profile against $Na_V$ (Wang et al., *Cellular Signaling* 2003, 15, 151-159). Collectively, this class of toxins is known to elicit changes in activation potential (Rao et al., *Pflugers Arch—Eur. J. Physiol.* 2000, 439, 349-355), single channel conductance (Correa et al., *J. Gen. Physiol.* 1991, 97, 605-625), ion selectivity (Rao et al., *Pflugers Arch—Eur. J. Physiol.* 2000, 439, 349-355), and the rate of channel inactivation (Krueger et al., *Nature* 1983, 303, 172-174). The precise molecular details by which ligand binding affects these properties is largely unresolved. Site-directed mutagenesis has been used to establish a subset of the residues comprising the batrachotoxin binding site, and a computational model has been developed. See Wang et al., *Molecular Pharmacology* 2006, 69, 788-795.

Synthetic Routes to Batrachotoxin

A retrosynthetic plan for preparing BTX is depicted in Scheme 1. Of the strategies considered for assembling the A/B ring system from an advanced intermediate, a Diels-Alder sequence was selected using furan 3 as the diene component. The choice of this heterocycle as a B-ring surrogate offers flexibility in terms of dienophile selection and is expected to facilitate analogue production. Furan 3 is further deconstructed by unraveling the homomorpholine unit. Latent symmetry elements appear in the resulting tricyclic structure 4 that are revealed in ketone 5. The preparation of 5 follows from dione 6 and a suitably derived furan. In this context, the furan is intended to serve as a 1,2-vicinal dianion equivalent.

Scheme 1 Retrosynthetic analysis of batrachotoxin 1

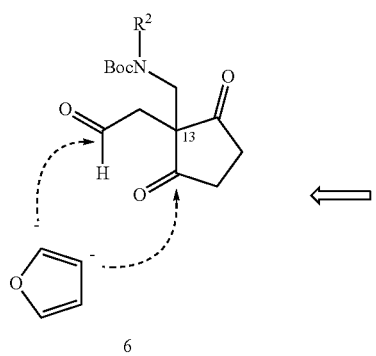
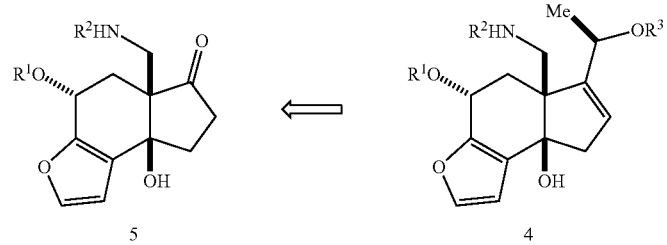

Installation of the C13 quaternary carbon center is performed in the initial stages of the BTX synthesis through a three-step sequence from 1,3-cyclopentadione (Scheme 2). Mannich reaction with this diketone and a suitable imine or iminium electrophile are problematic, as the product readily reverts to starting materials under acidic or basic conditions. McComas et al., *Org. Lett.*, 2002, 4, 2337. The use of sulfone 8 as an imine precursor, however, enables formation of the N-Boc-protected Mannich product 9 in 86% yield. (For the development of a related sulfone see: Guinchard et al., *Org. Lett.*, 2005, 7, 5147.) Both sulfone 8 and the dione product 9 are easily prepared on multigram scales. Subsequent allylation of 9 under basic conditions does not induce retro-Mannich or β-elimination of the NHBoc group; instead, a 2:1 mixture of O- and C-allylated products is furnished. The choice of base has little influence on product selectivity; however, the mixture of isomers converges to the desired C-allylated product 10 upon heating in toluene (98%, two steps).

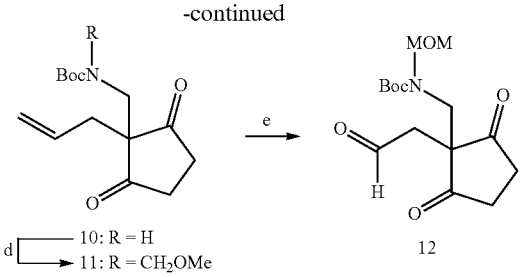

Reagents and conditions: (a) PhSO$_2$Na, aq. CH$_2$=O, HCO$_2$H, MeOH, 78%; (b) 1,3-cyclopentadione, DBU, THF, 86%; (c) allyl bromide, K$_2$CO$_3$; toluene, 110° C., (98%, 2 steps); (d) Me$_3$SiCl, paraformaldehyde, CH$_2$Cl$_2$, 0° C.; 9:1 MeOH/Et$_3$N, 5° C., 80%; (e) O$_3$, CH$_2$Cl$_2$, -78° C.; Me$_2$S, 83%.
DBU = 1,8-diazabicyclo[5.4.0]undec-7-ene.

Ozonolysis of alkene 10 to reveal the tricarbonyl species 13, while successful, gives exclusively hemi-aminal 14 (eq 1). Efforts to protect the nitrogen center in 10 using various alkylating agents (e.g., MeI or Me$_2$SO$_4$) and bases (e.g., NaH or KHMDS) resulted in retro-Mannich reaction. The application of a recently developed protocol for N-methoxymethyl (MOM) protection of carbamates using paraformaldehyde and MeOH successfully affords 11 in 80% yield (Scheme 2). Barnes et al., *Org. Lett.*, 2009, 11, 273. Subsequent alkene cleavage with O$_3$ gives the desired aldehyde 12, an important component of the synthetic plan.

Scheme 2 Initial stages of synthesis

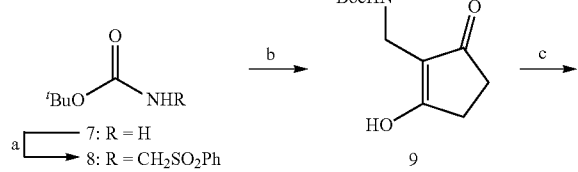

Scheme 3 Predicted stereochemical outcome of furyl anion meso-breaking addition.

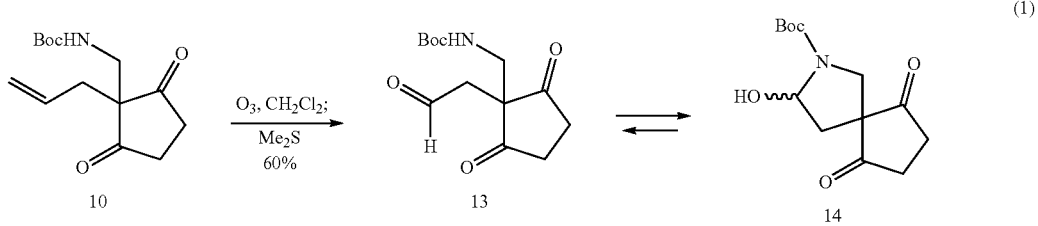

(1)

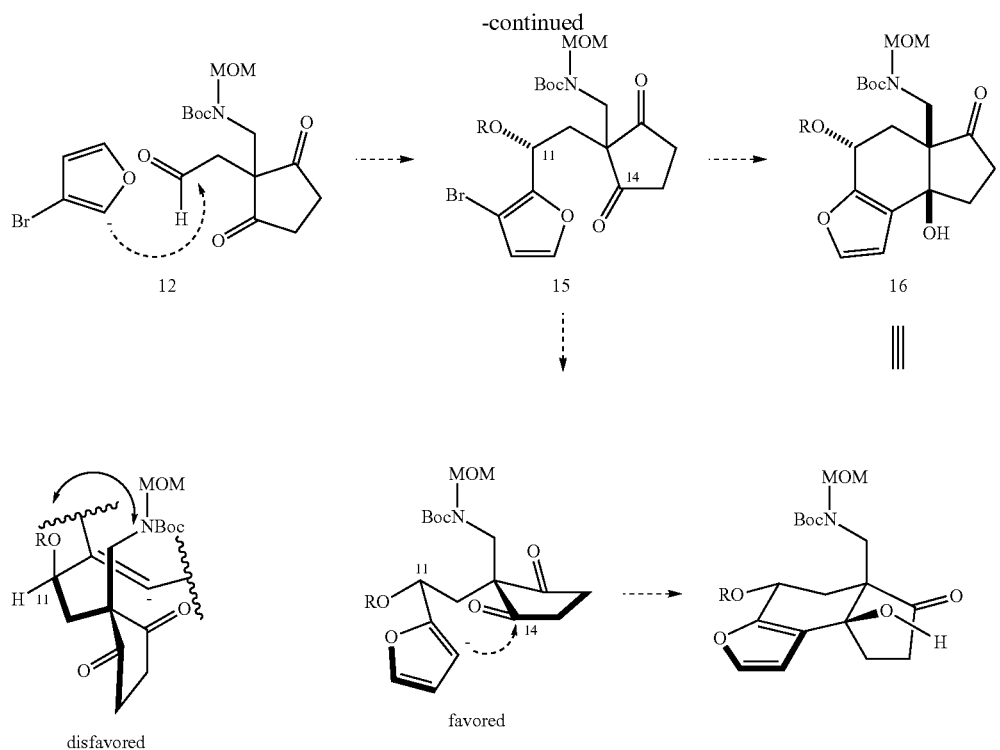

As originally conceived, sequential addition of a vicinal dianion nucleophile to 12 would make possible diastereoselective C-ring formation through a meso-breaking desymmetrization event (Scheme 3). While several potential dianion surrogates were considered at this stage of planning, 3-bromofuran appeared optimal in the first-generation design of our synthesis. Selective C2-lithiation of 3-bromofuran is possible using LiN$^i$Pr$_2$; elimination to the heteroaryne does not occur at reduced temperature. Ly and Schlosser, *Helv. Chim. Acta,* 1977, 60, 2085. Addition of this anion to the aldehyde moiety in 12 was expected to furnish 2° alcohol 15 (R═H). Following alcohol protection, metal-halogen exchange would trigger cyclization to establish the cis-fused C/D ring junction. In theory, the intermediate furyl anion could add to either ketone group to generate diasteromeric products. A preferred transition structure in which the C11-alkoxy group is disposed in a pseudo-equatorial arrangement should favor the desired stereoisomer 16.

Addition of 2-lithio-3-bromofuran to diketo-aldehyde 12 occurs exclusively at C11 to afford a 3:2 diastereomeric mixture of hemiacetals 18 rather than alcohol 17 (Scheme 4). Attempts to promote hemiacetal ring opening and 2° alcohol protection, however, did not prove successful; instead, use of MOMCl and amine base gives the unusual bis-acetal structures 19 in a slightly improved 2:1 diastereomeric ratio. Without intending to be bound by theory, the preference for isomer 19-endo, in which the furan unit is located on the concave face of the bicyclic, may be the result of a stereoelectronic preference for O-lone pair→σ*(C11-C9) delocalization. The value of the major diastereomer 19-endo for generating the C/D ring system of BTX is evident. Treatment of 19 with n-BuLi at −78° C. results in selective lithium-halogen exchange, and intramolecular anion addition to the C14-ketone (BTX numbering) furnishes the bridged tetracycle 20. Lithium-halogen exchange is performed on a 2:1 19-endo/exo mixture to give 60% isolated yield of 20 (89% based on theoretical maximum) and 30% of the proto-debrominated exo product. Access to 19-endo thus enables C/D ring formation with perfect control of relative stereochemistry between the C11 and C14 centers.

Scheme 4 Synthesis of bridged tetracycle 20

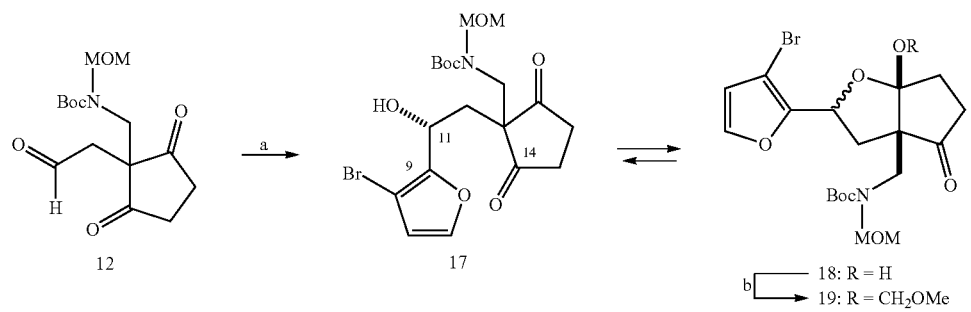

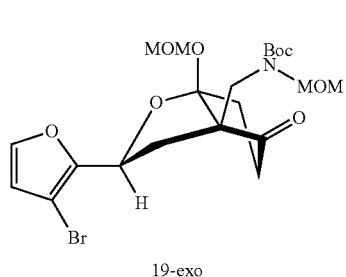
19-exo

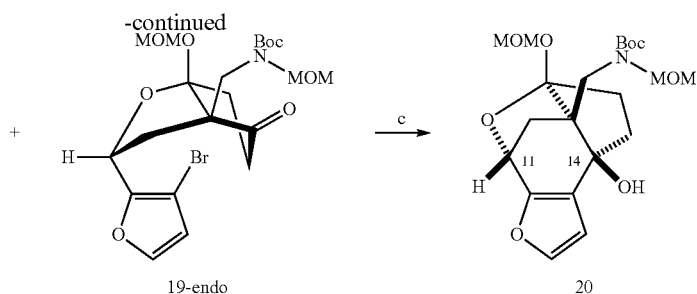
19-endo     20

Reagents and conditions: (a) 3-bromofuran, LiN'Pr₂, THF, -78° C., 3:2 dr, 89%; (b) MOMCl, i-PrNEt₂, 2:1 endo/exo, 80%; (c) n-BuLi, THF, -78° C., 89% based on 19-endo starting material.

Having established a preparative route to 20, a three-step sequence makes possible elaboration of this structure to tricycle 22 (Scheme 5). High yielding, 3° alcohol allylation is effected using a biphasic reaction protocol with 50% aqueous NaOH and n-Bu₄NI as a phase-transfer agent. Goto et al., *Org. Lett.,* 2007, 9, 5373. Subsequent acetal hydrolysis reveals the C17 ketone, which is smoothly transformed to the corresponding vinyl triflate. Stille cross-coupling with (1-ethoxyvinyl)tributyltin followed by aqueous acid treatment affords methyl ketone 23 (81% yield over three steps). Notably, strong acid hydrolysis also cleaves the N-MOM group. Finally, diastereoselective 1,2-reduction of the C20 enone is achieved using i-Bu₂AlH as the hydride source. In this reaction, and without intending to be bound by theory, we speculate that the 2° carbamate may serve as a stereochemical controlling element to favor preferential addition to the si-face of the ketone. Exclusive formation of the β-configured C20-alcohol 24, as required for completing the C/D/E ring synthesis, is consistent with the putative chelate addition model. Crystallographic analysis of an analogue structure confirms the C20-β-configuration.

Scheme 5 Synthesis of tricycle 27

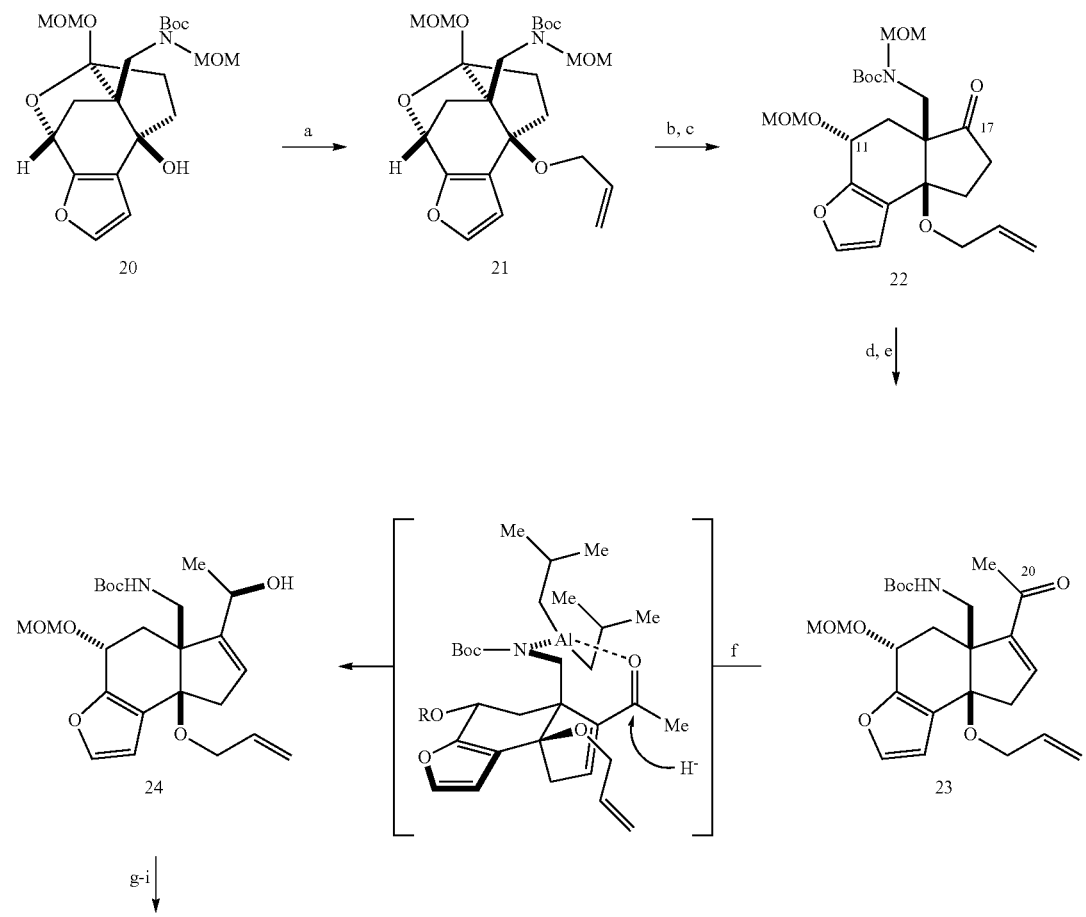

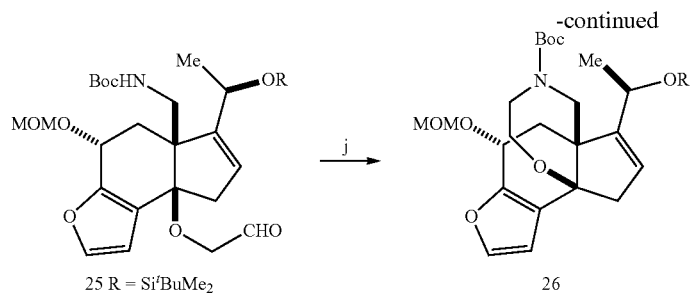

25 R = Si'BuMe₂

-continued

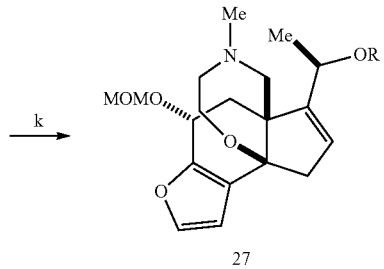

26

27

Reagents and conditions: (a) allyl bromide, n-Bu₄NI, CH₂Cl₂, 50% aq. NaOH, 89%; (b) MeC(O)Cl, MeOH, 0° C., 92%; (c) MOMCl, i-PrNEt₂, CH₂Cl₂, 40° C., 92%; (d) KN(SiMe₃)₂, N (5-chloro-2-pyridyl)triflimide, THF, -78° C., 95%; (e) tributyl(1-ethoxyvinyl)tin, 10 mol % Pd(PPh₃)₄, CuCl, DMSO, 65° C.; 4N aq. HCl, EtOAc, 0° C., 85%; (f) i-Bu₂AlH, toluene, -78° C., 76%; (g) t-BuMe₂SiOTf, 2,6-lutidine, CH₂Cl₂, -78° C., 99%; (h) 14 mol % OsO₄, NMO, H₂O/THF; (i) Pb(OAc)₄, CH₂Cl₂, 91% (over 2 steps); (j) MgSO₄, CH₃CO₂H, DCE; NaBH₃CN, 74%; (k) LiAlH₄, THF, 65° C., 73%. NMO = N-methylmorpholine N-oxide.

Starting from alcohol 24, homomorpholine ring synthesis is achieved through an efficient reductive amination sequence (Scheme 5). Despite the weakly nucleophilic nature of the carbamate moiety, condensation of this group with the intermediate aldehyde 25 is favorable under the action of acetic acid and MgSO₄. In situ iminium ion reduction occurs with NaCNBH₃ to afford the bridging 7-membered ring structure 26 in 74% yield. For a related N-Boc pyrrolidine synthesis, see Sakaguchi et al., *Org. Lett.,* 2008, 10, 5449. The major byproduct of this reaction results from reduction of aldehyde 25 to a primary alcohol. Mesylation of this alcohol and subsequent intramolecular $S_N2$ displacement gives 26, increasing the overall yield of homomorpholine ring closure to 84%. Without intending to be bound by theory, the success of the cyclization of 25 to 26 is attributed to both the highly electrophilic character of the α-alkoxyaldehyde and the geometric constraints of the C/D ring fusion. Following a second metal hydride reaction, this one employing LiAlH₄ to reduce the N-Boc group, assembly of the fully functionalized C/D/E core 27 of the natural product is accomplished. An x-ray crystallographic structure of compound 27, with R═H, is provided in FIG. 1.

We have explored a variety of Diels-Alder reactions with furan 26 in an effort to complete the synthesis of BTX and to evaluate dienophile reactivity for BTX analogue design. For a review of furan Diels-Alder reactions: Kappe et al., *Tetrahedron,* 1997, 53, 14179. Cycloaddition reactions with electron-deficient alkynes showed encouraging preliminary results and -continued 1.
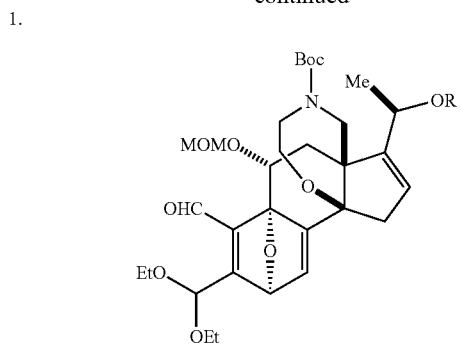
42%
1:1 A/B 2.
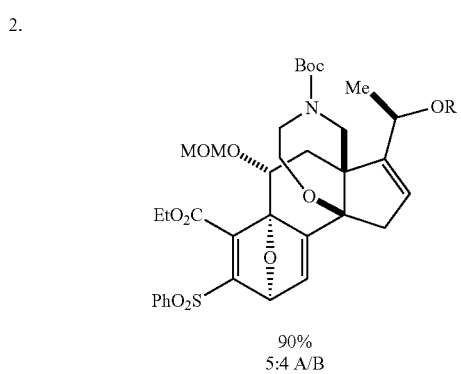
90%
5:4 A/B 3.
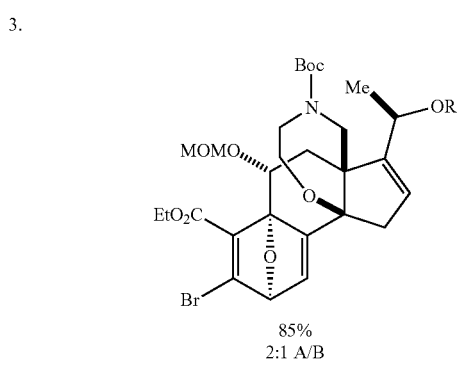
85%
2:1 A/B 4.
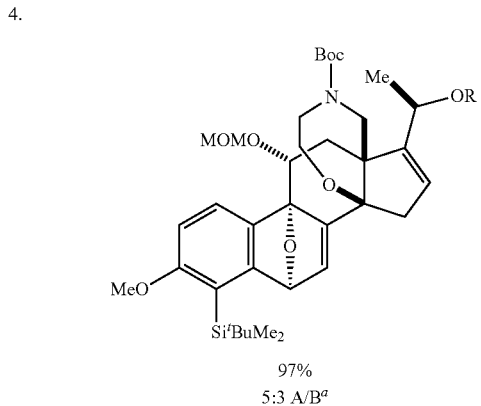
97%
5:3 A/B[a]

5.

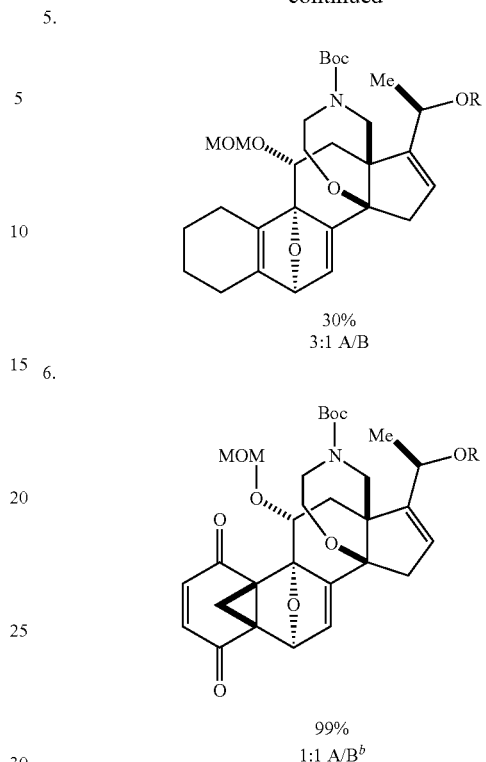

30%
3:1 A/B

6.

99%
1:1 A/B[b]

[a] A regioisomeric Diels-Alder product having C6 S, C9 R stereochemistry is also obtained. [b] The cyclopropane stereochemistry in B is inverted from that depicted (i.e. C5 S, C10 R). In addition, a third product having C5 S, C6 S, C9 R, C10 R stereochemistry is also obtained.

The modest reactivity of furan as a diene for [4+2] cycloadditions and the proclivity of the oxo-bridged bicyclic products to undergo cycloreversion have hindered attempted reactions with several other common dienophiles. Other alkyne and alkene substrates tested include ethyl propiolate and 2-bromo-4-ethoxycyclohexa-1,3-dienecarbaldehyde. Use of high pressure conditions (>6 kbar) with methyl maleic anhydride also resulted in no reaction. Reactions of 26 with highly strained dienophiles have been shown to cycloadd irreversibly with furan and simple furan derivatives. Benzyne, cyclohexyne, and cyclopropene derivatives react productively with 26 to give the expected Diels-Alder adducts (Scheme 6, products 4-6). Akai et al., *Angew. Chem. Int. Ed.,* 2008, 47, 7673; Shakespeare and Johnson, *J. Am. Chem. Soc.,* 1990, 112, 8578; Atanes et al., *Tet. Lett.,* 1998, 39, 3039; Collis et al., *Austr. J. Chem.* 1997, 50, 505. Each of these structures comprises the pentacyclic framework of BTX. Dienophile generation has been found to be most effective using CsF to promote elimination of a vicinally-substituted silyl-vinyl triflate or -vinyl halide, and reaction efficiency is excellent for two of the examples shown. With these [4+2] additions, however, facial selectivities across the furan diene are comparable to those obtained with alkyne dienophiles and only slightly in favor of the desired product.

The Diels-Alder cycloadditions with furan 26 have provided a collection of structurally unique analogues possessing the pentacyclic core of BTX. In addition, reactions of furan 21 with dienophiles, including cyclohexyne and a substituted benzyne have been investigated (Scheme 7). The three-dimensional topology of this tetracyclic structure effectively precludes approach of the dienophile from the α face of the furan, and the desired products 29 and 30 are furnished with >20:1 stereoselectivity. The utility of the CsF-promoted method for generating strained dienophiles is illustrated in these examples, as treatment of 21 with a cyclohexenyl phenyliodonium salt, a known cyclohexyne precursor, gives none of the desired cycloadduct. Fujita et al., *J. Am. Chem. Soc.,* 2004, 126, 7548; Gampe and Carreira, *Angew. Chem. Int. Ed.,* 2011, 50, 2962. Products such as 29 and 30 should facilitate access to BTX analogues with alternative D-ring and/or homomorpholine configurations than those highlighted in Scheme 6 and may allow for preparation of the natural product itself.

Scheme 7 Highly selective cyclohexyne and benzyne Diels-Alder reactions with furan 21

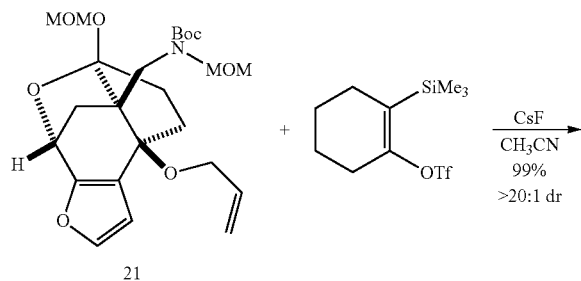

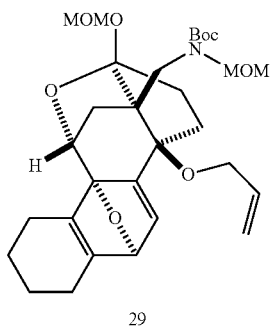

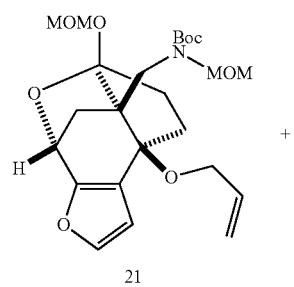

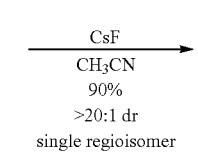

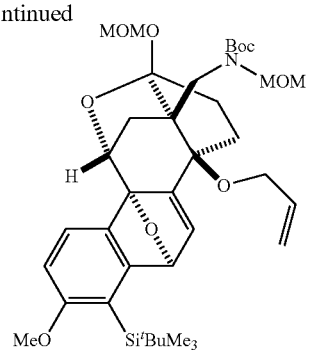

As just described, a synthetic plan that makes available novel pentacyclic forms of BTX possessing the fully elaborated C/D/E ring core has been outlined. Highlights of this work include the application of sulfone 8 for Mannich addition with cyclopentadiene, the use of 3-bromofuran as a vicinal dianion equivalent, desymmetrization of dione 17 through bis-acetal formation, Li—Br exchange for C-ring formation, and homomorpholine assembly through reductive alkylation. In addition, Diels-Alder reactions with furans 21 and 26 and ring-strained dienophiles have been examined for introduction of the A-ring moiety. Use of CsF to trigger benzyne, cyclohexyne, and cyclopropene formation from corresponding trimethylsilyl starting materials has proven to be a general and effective method, affording in most cases high yields of the desired cycloadducts.

Materials and Methods

General.

All reagents were obtained commercially unless otherwise noted. Reactions were performed using oven-dried glassware under an atmosphere of dry nitrogen. Air- and moisture sensitive liquids and solutions were transferred via syringe or stainless steel cannula. Organic solutions were concentrated under reduced pressure (~20 Torr) by rotary evaporation. Dichloromethane ($CH_2Cl_2$), dimethylsulfoxide (DMSO), tetrahydrofuran (THF), acetonitrile (MeCN), and toluene were passed through columns of activated alumina immediately prior to use. Methanol, dichloroethane (DCE), triethylamine, N,N-diisopropylamine and N,N,N-diisopropylethylamine were distilled from $CaH_2$ immediately prior to use. 2,6-Lutidine was dried over activated 3 Å molecular sieves. Chromatographic purification of products was accomplished using forced flow chromatography on Silicycle silica gel 60 (40-63 μm). Thin layer chromatography was performed on EM Science silica gel 60 $F_{254}$ plates (250 μm). Visualization of the developed chromatogram was accomplished by fluorescence quenching and by staining with aqueous potassium permanganate or aqueous ceric ammonium molybdate (CAM) solution.

Nuclear magnetic resonance (NMR) spectra were acquired on a Varian Inova spectrometer operating at 400, 500 or 600 and 100, 125 or 150 MHz for $^1H$ and $^{13}C$, respectively, and are referenced internally according to residual solvent signals. Data for $^1H$ NMR are recorded as follows: chemical shift (δ, ppm), multiplicity (s, singlet; d, doublet; t, triplet; q, quartet; m, multiplet; br, broad), integration, coupling constant (Hz). Data for $^{13}C$ NMR are reported in terms of chemical shift (6, ppm). Infrared spectra were recorded as either thin films using NaCl plates on a Thermo-Nicolet 300 FT-IR spectrometer and are reported in frequency of absorption. High resolution mass spectra were obtained from the Vincent Coates Foundation Mass Spectrometry Laboratory at Stanford University.

Experimental Procedures and Characterization for Compounds Appearing in Schemes 2, 4, and 5:

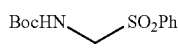

8 tert-Butyl((phenylsulfonyl)methyl)carbamate

Formic acid (8.0 mL, 212 mmol, 1.2 equiv) was added dropwise to a vigorously stirred solution of PhSO$_2$Na (72.5 g, 442 mmol, 2.5 equiv), t-butylcarbamate (20.7 g, 177 mmol), and 37% w/w aqueous formaldehyde (28.7 g, 353 mmol, 2.0 equiv) in 410 mL of H$_2$O and 135 mL of CH$_3$OH. The solution was stirred for 10 days, during which time a white precipitate formed. The solid material was collected by vacuum filtration with a sintered glass funnel, and the flask and filter cake were washed with 5×20 mL portions of H$_2$O. The isolated product 8 was dried in vacuo (37.6 g, 78%). Additional purification of this material was deemed unnecessary based on the recorded NMR data. $^1$H NMR (CDCl$_3$, 500 MHz) δ 7.92 (d, 2H, J=7.7 Hz), 7.66 (t, 1H, J=7.5 Hz), 7.55 (t, 2H, J=7.8 Hz), 5.33 (br s, 1H), 4.53 (d, 2H, J=7.0 Hz), 1.25 (s, 9H) ppm; $^{13}$C NMR (CDCl$_3$, 100 MHz) δ 154.1, 137.0, 134.4, 129.4, 129.2, 81.3, 62.3, 28.2 ppm; IR (thin film) ν 3355, 1696, 1366, 1288, 1145, 1087, 1009 cm$^{-1}$; HRMS (ES$^+$) calcd C$_{12}$H$_{17}$NO$_4$S 294.0776. found 294.0770 (MNa$^+$).

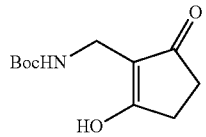

9 tert-Butyl((2-hydroxy-5-oxocyclopent-1-en-1-yl)methyl)carbamate

To a solution of 8 (17.8 g, 65.5 mmol, 1.1 equiv) and 1,3-cyclopentanedione (5.8 g, 59.6 mmol) in 250 mL of THF was added dropwise over 7 min 1,8-diazabicyclo[5.4.0]undec-7-ene (8.9 mL, 59.5 mmol, 1.0 equiv). After stirring this mixture for 10 min, a second portion of 1,8-diazabicyclo[5.4.0]undec-7-ene was added (9.8 mL, 65.5 mmol, 1.1 equiv) dropwise. The reaction was stirred for 21 h then concentrated under reduced pressure to one-third its original volume. The contents were transferred to a separatory funnel with 100 mL of CHCl$_3$ and the organic layer was washed with 400 mL of a pH 4 aqueous NaH$_2$PO$_4$/Na$_2$HPO$_4$ buffer. The aqueous fraction was collected and extracted with 5×160 mL of CHCl$_3$. The combined organic extracts were dried over Na$_2$SO$_4$, filtered and concentrated under reduced pressure to an orange oil. Purification of this material by chromatography on silica gel (gradient elution: 3.5→4% MeOH/CH$_2$Cl$_2$) afforded vinylogous acid 9 as a white solid (11.6 g, 86%). TLC R$_f$=0.56 (10% MeOH/CH$_2$Cl$_2$); $^1$H NMR (CDCl$_3$, 500 MHz) δ 5.34 (br s, 1H), 3.77 (d, 2H, J=6.4 Hz), 2.56-2.53 (m, 2H), 2.46-2.43 (m, 2H), 1.45 (s, 9H) ppm; $^{13}$C NMR (CDCl$_3$, 125 MHz) δ 160.3, 116.2, 81.7, 31.5, 28.45, 28.50 ppm; note: $^{13}$C NMR signal for C17 could not be detected; IR (thin film) ν 3315, 2978, 2929, 1643, 1523, 1383, 1169 cm$^{-1}$; HRMS (ES$^+$) calcd C$_{11}$H$_{17}$NO$_4$ 250.1056. found 250.1051 (MNa$^+$).

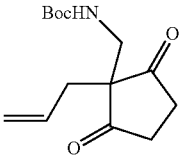

10

To a suspension of 9 (5.1 g, 22.3 mmol) and K$_2$CO$_3$ (6.2 g, 44.7 mmol, 2.0 equiv) in 90 mL of acetone was added allyl bromide (7.8 mL, 89.4 mmol, 4.0 equiv). The reaction was stirred at 60° C. for 6 h, cooled to room temperature, and filtered through a large pad of Celite. The flask and filter cake were rinsed with ~80 mL of CH$_2$Cl$_2$, and the combined filtrates were concentrated under reduced pressure to a dark yellow oil. This material was transferred to a reparatory funnel with 100 mL of CH$_2$Cl$_2$ and 40 mL of a pH 4 aqueous NaH$_2$PO$_4$/Na$_2$HPO$_4$ buffer. The organic layer was collected and the aqueous fraction was extracted with 4×50 mL of CH$_2$Cl$_2$. The combined organic extracts were dried over Na$_2$SO$_4$, filtered, and concentrated under reduced pressure to a yellow oil. The product was determined to be a ~2:1 mixture of C- to O-allylated products by $^1$H NMR, and was deemed pure for immediate use in the subsequent reaction. The allylated material was dissolved in 200 mL of toluene and stirred at reflux for 48 h. Following this time, the reaction was cooled to room temperature and concentrated under reduced pressure. Purification of the isolated material by chromatography on silica gel (40% EtOAc/hexanes) furnished the diketone 10 as a yellow oil (5.8 g, 98% yield). TLC R$_f$=0.67 (5% MeOH/CH$_2$Cl$_2$); $^1$H NMR (CDCl$_3$, 500 MHz) δ 5.60-5.52 (m, 1H), 5.09-5.07 (m, 1H), 5.05 (s, 1H), 4.84 (s, 1H), 3.32 (d, 2H, J=6.4 Hz), 2.79-2.72 (m, 2H), 2.67-2.58 (m, 2H), 2.36 (d, 2H, J=7.5 Hz), 1.39 (s, 9H) ppm; $^{13}$C NMR (CDCl$_3$, 125 MHz) δ 215.1, 156.0, 131.2, 120.5, 80.3, 61.2, 43.9, 37.5, 36.4, 28.4 ppm; IR (thin film) ν 3373, 2979, 2931, 1719, 1520, 1251, 1170 cm$^{-1}$; HRMS (ES$^+$) calcd C$_{14}$H$_{21}$NO$_4$ 290.1369. found 290.1363 (MNa$^+$).

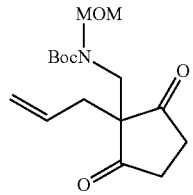

11

A flame-dried 250 mL round-bottomed flask equipped with a magnetic stir bar was charged with diketone 10 (7.7 g, 28.8 mmol), paraformaldehyde (1.3 g, 43.2 mmol, 1.5 equiv), and 95 mL of CH$_2$Cl$_2$. The flask was placed in an ice bath and freshly distilled chlorotrimethylsilane (9.4 g, 86.4 mmol, 3.0 equiv) was added dropwise over a 3 min period. The mixture was stirred at 0° C. for 4 h and then a solution of Et$_3$N (1.9 mL, 13.6 mmol, 0.5 equiv) in 17 mL of MeOH was added. White smoke emanated from the reaction mixture upon addition of this methanolic solution. The contents were stirred for 30 min at 0° C. Following this time, the reaction mixture was slowly poured into a separatory funnel containing 300 mL of saturated aqueous NaHCO$_3$ (note: vigorous gas evolution is observed in this quench). The organic layer was collected, and the aqueous layer was extracted with 4×100 mL of $CH_2Cl_2$. The combined organic extracts were dried over $Na_2SO_4$, filtered and concentrated under reduced pressure to a yellow oil. Purification of this material by chromatography on silica gel (gradient elution: 14:4:1→7:2:1 hexanes/$CH_2Cl_2$/acetone) afforded the carbamate 11 as a light yellow oil (7.2 g, 80%). TLC $R_f$=0.41 (7:2:1 hexanes/$CH_2Cl_2$/acetone); $^1H$ NMR ($CDCl_3$, 400 MHz, 45° C.) δ 5.57-5.47 (m, 1H), 5.05-4.99 (m, 2H), 4.44 (s, 2H), 3.53 (s, 2H), 3.11 (s, 3H), 2.65-2.56 (m, 2H), 2.52-2.46 (m, 2H), 2.23 (d, 2H, J=7.1 Hz), 1.40 (s, 9H) ppm; $^{13}C$ NMR ($CDCl_3$, 100 MHz, 45° C.) δ 213.8, 155.3, 130.8, 120.4, 81.2, 80.2, 60.7, 55.2, 48.9, 40.0, 35.9, 28.2 ppm; IR (thin film) ν 2979, 2933, 1726, 1705, 1419, 1367, 1299, 1159 $cm^{-1}$; HRMS ($ES^+$) calcd $C_{16}H_{25}NO_5$ 334.1631. found 334.1626 ($MNa^+$).

mixture at −78° C. for 3 h, a solution of lithium bromide (2.84 g, 32.7 mmol, 1.25 equiv) in 20 mL of THF was added. After 45 min, aldehyde 12 (8.20 g, 26.2 mmol, azeotropically dried with toluene) was added as a solution in 75 mL THF. Transfer of this material was made quantitative with an additional 25 mL of THF. Following an additional 30 min at −78° C., the reaction was quenched by the addition of 300 mL of saturated aqueous $NH_4Cl$. The contents were transferred to a separatory funnel with 200 mL of EtOAc and the organic phase was collected. The aqueous fraction was extracted with 2×300 mL of EtOAc. The combined organic extracts were dried over $Na_2SO_4$, filtered and concentrated under reduced pressure to a yellow foam. Purification of this material by chromatography on silica gel (35% EtOAc/hexanes) afforded a 3:2 diastereomeric mixture of hemi-ketals 18 (10.7 g, 89%) as a white foam. TLC $R_f$=0.52 (50% EtOAc/hexanes); HRMS ($ES^+$) calcd $C_{19}H_{26}BrNO_7$ 482.0791. found 482.0788 ($MNa^+$).

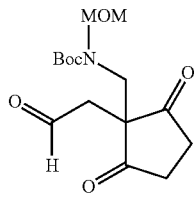

12

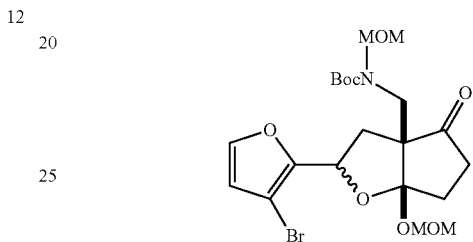

19

A stream of $O_3$ was bubbled for 45 min through a −78° C. solution of alkene 11 (9.30 g, 29.9 mmol) in 150 mL of $CH_2Cl_2$ containing approximately 3 mg of Sudan III dye. At the end of this period, the solution changed from red to pale blue-gray in color. Thin layer chromatography indicated complete consumption of starting material. The solution was then sparged with a stream of $N_2$ gas for 45 min while warming to room temperature. Dimethyl sulfide (11.0 mL, 149 mmol, 5.0 equiv) was added and the mixture was stirred for 8 h. All volatiles were then removed under reduced pressure to afford an off-white foam. Purification of this material by chromatography on silica gel (gradient elution: 40→50% EtOAc/hexanes then 1:1:1 EtOAc/hexanes/$CH_2Cl_2$) afforded aldehyde 12 as a white solid (7.8 g, 83%). TLC $R_f$=0.40 (50% EtOAc/hexanes); $^1H$ NMR ($CDCl_3$, 400 MHz) δ 9.35 (s, 1H), 4.51 (s, 2H), 3.38 (s, 2H), 3.21 (s, 5H), 2.87 (d, 4H, J=0.2 Hz), 1.40 (s, 9H) ppm; $^{13}C$ NMR ($CDCl_3$, 100 MHz) δ 214.3, 199.0, 155.5, 81.7, 80.4, 56.4, 55.8, 50.3, 49.5, 36.1, 28.2 ppm; IR (thin film) ν 2930, 2854, 1723, 1718, 1418, 1369, 1297, 1158, 1086 $cm^{-1}$; HRMS ($ES^+$) calcd $C_{15}H_{23}NO_6$ 336.1423. found 336.1419 ($MNa^+$).

Chloromethyl methyl ether (6.7 mL, 88.6 mmol, 4.0 equiv) and diisopropylethylamine (19.3 mL, 111.0 mmol, 5.0 equiv) were added sequentially to a solution of hemi-ketals 18 (10.2 g, 22.2 mmol) in 110 mL of $CH_2Cl_2$. The solution was stirred at reflux for 15 h, then cooled to room temperature and diluted with 150 mL of a pH 4 aqueous $NaH_2PO_4$/$Na_2HPO_4$ buffer. After 30 min of vigorous stirring, the mixture was transferred with 100 mL of $CH_2Cl_2$ to a separatory funnel containing 120 mL of a pH 4 aqueous $NaH_2PO_4$/$Na_2HPO_4$ buffer. The organic layer was collected, and the aqueous fraction was extracted with 3×100 mL of $CH_2Cl_2$. The combined organic extracts were dried over $Na_2SO_4$, filtered and concentrated under reduced pressure to a yellow foam. Purification of this material by chromatography on silica gel (35% EtOAc/hexanes) afforded a 2:1 diastereomeric mixture of ketones 19 (9.0 g, 80%) as a light yellow foam. TLC $R_f$=0.56 (40% EtOAc/hexanes); $^1H$ NMR ($CDCl_3$, 400 MHz, mixture of diastereomers) δ 7.32-7.28 (m, 2H), 6.35-6.31 (m, 2H), 5.27-5.23 (m, 2H), 5.11-5.10 (m, 2H), 5.03-4.96 (m, 2H), 4.72-4.68 (m, 4H), 4.62-4.50 (m, 2H), 4.09-4.01 (m, 2H), 3.44 (s, 6H), 3.37 (s, 2H), 3.27 (s, 6H), 2.68-2.64 (m, 2H), 2.52-2.49 (m, 4H), 2.44-2.38 (m, 4H), 1.42 (s, 18H) ppm; HRMS ($ES^+$) calcd $C_{21}H_{30}BrNO_8$ 526.1053. found 526.1049 ($MNa^+$). The relative stereochemistry of the major and minor diastereomeric products was not assigned.

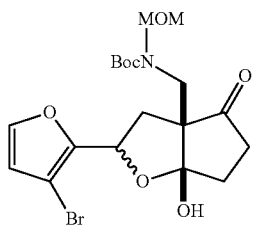

18

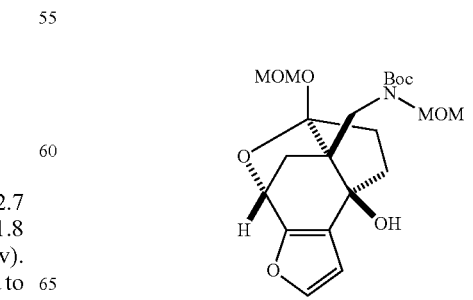

20

To an ice-cold solution of diisopropylamine (4.62 mL, 32.7 mmol, 1.25 equiv) in 100 mL of THF was added n-BuLi (21.8 mL of a 1.5 M solution in hexanes, 32.7 mmol, 1.25 equiv). The mixture was stirred at 0° C. for 20 min and then cooled to −78° C. before 3-bromofuran (2.94 mL, 32.7 mmol, 1.25 equiv) was added dropwise via cannula. After stirring this To a −78° C. solution of ketones 19 (1.59 g, 3.14 mmol) in 31 mL of THF was added n-BuLi (1.4 mL of a 2.5 M solution in hexanes, 3.5 mmol, 1.1 equiv) dropwise over 30 sec. After stirring the mixture at −78° C. for 45 min, the reaction was quenched with 45 mL of saturated aqueous NH$_4$Cl. The mixture was warmed to room temperature, diluted with 25 mL of EtOAc and 15 mL of H$_2$O, and stirred vigorously until the both phases had clearly separated. The material was transferred to a separatory funnel, the organic layer was collected, and the aqueous fraction was extracted with 2×75 mL of EtOAc. The combined organic extracts were dried over Na$_2$SO$_4$, filtered and concentrated under reduced pressure to a yellow oil. Purification of this material by chromatography on silica gel (40% EtOAc/hexanes) afforded tertiary alcohol 20 (793 mg, 59%) as a clear oil and the debrominated 19-exo product (401 mg, 30%) as a clear oil. Tertiary alcohol 20: TLC R$_f$=0.37 (40% EtOAc/hexanes); $^1$H NMR (CDCl$_3$, 400 MHz) δ 7.22 (d, 1H, J=1.8 Hz), 6.46 (s, 1H), 5.28 (s, 1H), 4.99 (d, 1H, J=6.4 Hz), 4.96 (d, 1H, J=5.3 Hz), 4.91 (d, 1H, J=9.6 Hz), 4.73 (d, 1H, J=5.9 Hz), 4.60 (d, 1H, J=10.2 Hz), 4.07 (d, 1H, J=16.1 Hz), 3.78 (dd, 1H, J=15.5, 0.4 Hz), 3.41 (s, 3H), 3.30 (s, 3H), 2.21-1.91 (m, 5H), 1.61-1.56 (m, 1H), 1.48 (s, 9H) ppm; $^{13}$C NMR (CDCl$_3$, 100 MHz) δ 157.7, 155.2, 142.1, 122.7, 114.8, 108.5, 92.1, 81.7, 80.4, 77.6, 70.6, 61.3, 56.4, 56.0, 44.2, 37.0, 35.6, 34.5, 28.6 ppm; IR (thin film) ν 3417, 2976, 1699, 1674, 1307, 1148, 1030 cm$^{-1}$; HRMS (ES$^+$) calcd C$_{21}$H$_{31}$NO$_8$ 448.1948. found 448.1942 (MNa$^+$).

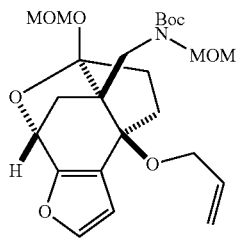

21

Allyl bromide (1.1 mL, 12.6 mmol, 8.0 equiv) was added dropwise to a vigorously stirred solution of alcohol 20 (670 mg, 1.57 mmol) and tetrabutylammonium iodide (582 mg, 1.57 mmol, 1.0 equiv) in 11 mL of CH$_2$Cl$_2$ and 21 mL of 50% w/w aqueous NaOH (note: a rapid stir rate, a large stir bar, and a large flask size to solution volume ratio should be used to obtain an optimal product yield). The biphasic solution was stirred for 12 h, then cooled to 0° C. and diluted with 50 mL of EtOAc and 50 mL of H$_2$O. The mixture was transferred to a reparatory funnel, the organic fraction was collected, and the aqueous layer was extracted with 3×50 mL of EtOAc. The combined organic extracts were dried over Na$_2$SO$_4$, filtered and concentrated under reduced pressure to a yellow oil. Purification of this material by chromatography on silica gel (20% EtOAc/hexanes) afforded allyl ether 21 (652 mg, 89%) as a white solid. TLC R$_f$=0.58 (40% EtOAc/hexanes); $^1$H NMR (CDCl$_3$, 400 MHz) δ 7.27 (d, 1H, J=1.2 Hz), 6.33 (dd, 1H, J=1.9, 0.8 Hz), 6.00-5.90 (m, 1H), 5.33 (d, 1H, J=17.5 Hz), 5.14 (d, 1H, J=10.2 Hz), 4.96 (t, 3H, J=9.3 Hz), 4.85 (d, 1H, J=10.2 Hz), 4.67 (d, 1H, J=6.5 Hz), 4.51 (dd, 1H, J=11.4, 5.4 Hz), 4.18-4.15 (m, 1H), 3.82 (dd, 1H, J=11.5, 4.6 Hz), 3.47 (d, 1H, J=15.4 Hz), 3.40 (s, 3H), 3.27 (s, 3H), 2.27-2.13 (m, 4H), 1.88 (q, 1H, J=9.6 Hz), 1.54-1.45 (m, 1H), 1.46 (s, 9H) ppm; $^{13}$C NMR (CDCl$_3$, 100 MHz) δ 157.8, 156.6, 142.4, 135.6, 119.3, 116.8, 115.6, 108.1, 92.1, 82.4, 80.0, 79.7, 70.4, 65.9, 59.9, 56.5, 55.5, 42.4, 36.5, 35.3, 33.7, 28.5 ppm; IR (thin film) ν 2978, 2930, 1700, 1295, 1146, 1034 cm$^{-1}$; HRMS (ES$^+$) calcd C$_{24}$H$_{35}$NO$_8$ 488.2261. found 488.2249 (MNa$^+$).

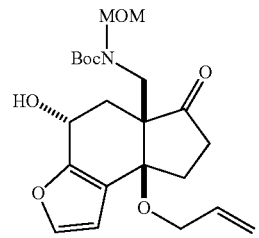

21A

Acetyl chloride (0.56 mL, 7.8 mmol, 3.0 equiv) was added to 18 mL of MeOH. The mixture was stirred at 0° C. for 30 min and then added dropwise over 2 min via cannula to an ice-cold solution of bis-acetal 21 (1.22 g, 2.62 mmol) in 9 mL of MeOH and 6 mL of THF. After 15 min, the reaction was quenched by slow addition of 60 mL of saturated aqueous NaHCO$_3$. The reaction was diluted with 60 mL of EtOAc and warmed to room temperature. The contents were transferred to a reparatory funnel with 40 mL of EtOAc and 30 mL of H$_2$O. The organic layer was collected and the aqueous fraction was extracted with 2×80 mL of EtOAc. The combined organic extracts were dried over Na$_2$SO$_4$, filtered and concentrated under reduced pressure to a white foam. Purification of this material by chromatography on silica gel (gradient elution: 40→50% EtOAc/hexanes) afforded keto-alcohol 21A (1.0 g, 92%) as a white solid. TLC R$_f$=0.27 (40% EtOAc/hexanes); $^1$H NMR (CDCl$_3$, 400 MHz) δ 7.41 (d, 1H J=1.5 Hz), 6.37 (d, 1H, J=2.0 Hz), 5.80 (ddt, 1H, J=16.8, 10.8, 5.6 Hz), 5.20 (dd, 1H, J=17.2, 1.4 Hz), 5.08 (d, 1H, J=10.2 Hz), 4.68 (dt, 3H, J=29.6, 7.9 Hz), 4.17 (d, 1H, J=15.1 Hz), 3.85 (d, 2H, J=5.1 Hz), 3.25 (d, 4H, J=16.9 Hz), 2.89 (d, 1H, J=9.2 Hz), 2.80 (dd, 1H, J=19.3, 9.9 Hz), 2.71 (d, 1H, J=15.2 Hz), 2.58 (q, 1H, J=11.4 Hz), 2.42 (dd, 1H, J=12.0, 9.2 Hz), 2.20 (dd, 1H, J=15.2, 6.3 Hz), 1.88 (dd, 1H, J=19.6, 9.7 Hz), 1.44 (s, 9H) ppm; $^{13}$C NMR (CDCl$_3$, 100 MHz) δ 220.2, 156.1, 154.5, 144.2, 134.9, 119.4, 116.4, 108.4, 81.2, 80.6, 80.2, 65.5, 60.5, 58.2, 55.8, 48.3, 35.6, 34.4, 30.6, 28.4 ppm; IR (thin film) ν 3502, 2976, 2928, 1729, 1701, 1417, 1296, 1141, 1087 cm$^{-1}$; HRMS (ES$^+$) calcd C$_{22}$H$_{31}$NO$_7$ 444.1999. found 444.1995 (MNa$^+$).

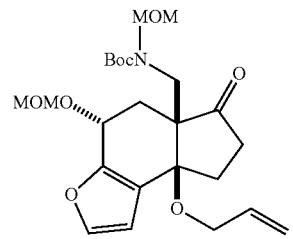

22

To a solution of keto-alcohol 21A (447 mg, 1.06 mmol) in 13 mL of CH$_2$Cl$_2$ were added chloromethyl methyl ether (0.56 mL, 7.4 mmol, 7.0 equiv) and diisopropylethylamine (2.77 mL, 15.9 mmol, 15.0 equiv). White smoke emanated from the reaction mixture upon addition of diisopropylethylamine. The solution was heated to reflux for 12 h, cooled to room temperature, and diluted with 45 mL a pH 4 aqueous NaH$_2$PO$_4$/Na$_2$HPO$_4$ buffer. After 30 min of vigorous stirring, the contents were transferred to a separatory funnel with 50 mL of CH$_2$Cl$_2$. The organic layer was collected, and the aqueous fraction was extracted with 3×50 mL of CH$_2$Cl$_2$. The combined organic extracts were washed with 1×50 mL of saturated aqueous NaCl, dried over Na$_2$SO$_4$, filtered, and concentrated under reduced pressure to a yellow oil. Purification of this material by chromatography on silica gel (40% EtOAc/hexanes) afforded ketone 22 (457 mg, 92%) as a clear oil. TLC R$_f$=0.51 (50% EtOAc/hexanes); $^1$H NMR (CDCl$_3$, 400 MHz) δ 7.45 (s, 1H), 6.44 (d, 1H, J=2.0 Hz), 5.82 (ddt, 1H, J=16.8, 10.8, 5.6 Hz), 5.23 (dq, 1H, J=17.2, 1.6 Hz), 5.10 (d, 1H, J=10.2 Hz), 4.79-4.65 (m, 4H), 4.58 (d, 1H, J=6.7 Hz), 4.15-3.97 (m, 1H), 3.84-3.74 (m, 2H), 3.41 (s, 3H), 3.31 (s, 3H), 3.24-3.20 (m, 1H), 2.89 (d, 1H, J=14.8 Hz), 2.64-2.35 (m, 3H), 1.93 (ddt, 2H, J=14.5, 7.2, 5.7 Hz), 1.45 (s, 9H) ppm; $^{13}$C NMR (CDCl$_3$, 100 MHz) δ 214.4, 156.0, 152.4, 144.1, 134.8, 121.1, 116.4, 108.3, 94.0, 81.3, 80.8, 80.5, 65.7, 62.9, 55.8, 55.6, 55.0, 48.5, 36.2, 33.3, 32.3, 28.4 ppm; IR (thin film) ν 2976, 2933, 1745, 1700, 1417, 1367, 1298, 1146, 1087, 1034 cm$^{-1}$; HRMS (ES$^+$) calcd C$_{24}$H$_{35}$NO$_8$ 488.2261. found 488.2255 (MNa$^+$).

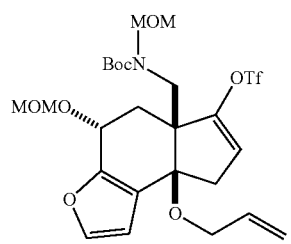

A solution of ketone 22 (203 mg, 0.44 mmol) in 1.0 mL of THF was added via cannula to a −78° C. solution of KN(SiMe$_3$)$_2$ (130 mg, 0.65 mmol, 1.5 equiv) in 1.0 mL of THF. Transfer of the ketone was made quantitative with an additional 2×0.5 mL of THF. The resulting yellow mixture was stirred at −78° C. for 40 min. A solution of N-(5-chloro-2-pyridyl)triflimide (234 mg, 0.60 mmol, 1.4 equiv), in 1.0 mL of THF was then added dropwise via cannula. Transfer of the triflimide was made quantitative with an additional 2×0.5 mL of THF. The deep orange solution was stirred at −78° C. for 3 h before the reaction was quenched by the addition of 12 mL of saturated aqueous NH$_4$Cl. The mixture was warmed to room temperature and transferred to a separatory funnel with 10 mL of EtOAc and 8 mL of H$_2$O. The organic layer was collected and the aqueous fraction was extracted with 2×30 mL of EtOAc. The combined organic extracts were dried over Na$_2$SO$_4$, filtered and concentrated under reduced pressure to a yellow, amorphous solid. Purification of the isolated material by chromatography on silica gel (gradient elution: 20→30% EtOAc/hexanes) furnished vinyl triflate 22A as a clear oil (247 mg, 95%). TLC R$_f$=0.63 (40% EtOAc/hexanes); $^1$H NMR (CDCl$_3$, 400 MHz, mixture of rotameric isomers) δ $^1$H NMR (400 MHz; CDCl$_3$) δ 7.41 (s, 1H), 6.38 (s, 1H), 5.81 (ddt, 1H, J=17.2, 10.5, 5.3 Hz), 5.31 (s, 1H), 5.22 (d, 1H, J=17.2 Hz), 5.11 (d, 1H, J=10.1 Hz), 5.02-4.40 (m, 1H), 4.91 (d, 1H, J=10.5 Hz), 4.81-4.78 (m, 2H), 4.60-4.56 (m, 1H), 4.00-3.52 (m, 1H), 3.81-3.66 (m, 3H), 3.38 (s, 3H), 3.27 (s, 3H), 2.93 (d, 1H, J=15.2 Hz), 2.69-2.59 (m, 2H), 2.02 (dd, 1H, J=15.5, 4.4 Hz), 1.48 (s, 9H) ppm; $^{13}$C NMR (CDCl$_3$, 100 MHz, mixture of rotameric isomers) δ 156.6, 151.8, 149.9, 143.7, 134.4, 121.3, 120.1, 116.8, 109.3, 108.6, 94.2, 82.1, 80.9, 80.3, 66.5, 62.0, 55.7, 55.5, 53.2, 48.5, 41.2, 33.7, 28.4 ppm; IR (thin film) ν 2933, 1707, 1423, 1211, 1146, 1032 cm$^{-1}$; HRMS (ES$^+$) calcd C$_{25}$H$_{34}$F$_3$NO$_{10}$S 620.1754. found 620.1751 (MNa$^+$).

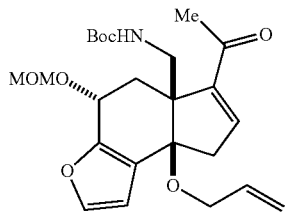

In an inert atmosphere N$_2$ glove box, Pd(PPh$_3$)$_4$ (192 mg, 166 mmol, 0.1 equiv), LiCl (423 mg, 10.0 mmol, 6.0 equiv), and CuCl (823 mg, 8.3 mmol, 5.0 equiv) were weighed into an oven-dried Schlenk flask containing vinyl triflate 22A (993 mg, 1.7 mmol). The flask was stoppered with a polyethylene cap and the side-arm fitted with a rubber septum. The vessel was removed from the glove box and charged with tributyl-1-ethoxyvinyltin (618 μL, 1.8 mmol, 1.1 equiv) and 33 mL of DMSO. The suspension was degassed through two freeze-pump-thaw cycles and then restored to a nitrogen atmosphere. The sealed vessel was placed in a 60° C. oil bath and the contents stirred at this temperature for 13 h. Following this time, the mixture was cooled to room temperature and transferred with 120 mL of Et$_2$O to a separatory funnel containing 200 mL of saturated aqueous NaCl and 60 mL of 5% aq NH$_4$OH. The organic layer was collected, and the aqueous fraction was extracted with 2×80 mL of Et$_2$O. The combined organic extracts were washed with 40 mL of saturated aqueous NaCl, dried over Na$_2$SO$_4$, filtered and concentrated under reduced pressure to a brown oil. The isolated material was dissolved in 55 mL of EtOAc and cooled to 0° C. To this solution was added 5.4 mL of 4.0 N aqueous HCl dropwise. The reaction mixture was stirred for 5.5 h at 0° C. then quenched by slow addition of 100 mL of saturated aqueous NaHCO$_3$. The solution was warmed to room temperature and transferred to a separatory funnel with 120 mL of EtOAc and 40 mL of saturated aqueous NaHCO$_3$. The organic layer was collected and the aqueous fraction was extracted of 2×75 mL of EtOAc. The organic extracts were combined, dried over Na$_2$SO$_4$, and concentrated under reduced pressure to a yellow oil. Purification of this material by chromatography on silica gel (gradient elution: 30→60% EtOAc/hexanes) furnished methyl ketone 23 as an off-white foam (633 mg, 85% over 2 steps). TLC R$_f$=0.57 (60% EtOAc/hexanes); $^1$H NMR (CDCl$_3$, 400 MHz) δ 7.41 (d, 1H, J=1.8 Hz), 6.46 (d, 1H, J=16.8 Hz), 6.40 (d, 1H, J=1.3 Hz), 5.87 (ddt, 1H, J=16.8, 10.9, 5.6 Hz), 5.60 (dd, 1H, J=8.1, 3.8 Hz), 5.25 (dd, 1H, J=17.2, 1.5 Hz), 5.14 (dd, 1H, J=10.4, 1.3 Hz), 4.78 (s, 1H), 4.64 (d, 1H, J=6.9 Hz), 4.41 (d, 1H, J=7.0 Hz), 3.95-3.81 (m, 2H), 3.75 (dd, 1H, J=14.0, 7.9 Hz), 3.37 (s, 3H), 3.25 (dd, 1H, J=13.9, 4.1 Hz), 3.12-3.00 (m, 2H), 2.80 (dd, 1H, J=17.9, 3.2 Hz), 2.19 (s, 3H), 1.71 (dd, 1H, J=15.0, 3.9 Hz), 1.42 (s, 9H) ppm; $^{13}$C NMR (CDCl$_3$, 100 MHz) δ 197.7, 156.4, 151.8, 147.2, 143.5, 139.6, 134.8, 122.0, 116.9, 109.1, 93.9, 84.0, 78.8, 66.9, 62.9, 55.5, 54.1, 45.7, 45.6, 30.1, 28.6, 27.5 ppm; IR (thin film) ν 3454, 2980, 2932, 1711, 1676, 1504, 1167, 1028 cm$^{-1}$; HRMS (ES$^+$) calcd C$_{24}$H$_{33}$NO$_7$ 470.2155. found 470.2150 (MNa$^+$).

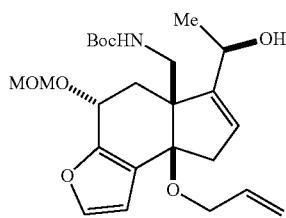

24

To a −78° C. solution of ketone 23 (191 mg, 0.43 mmol) in 8.5 mL of toluene was added dropwise diisobutylaluminum hydride (0.70 mL of a 1.0 M solution in toluene, 0.70 mmol, 1.64 equiv). The reaction was stirred at −78° C. for 50 min and then quenched with 5 mL of 1.0 M aqueous potassium sodium tartrate. The ice bath was removed and the mixture was stirred vigorously at room temperature for 5 h. The contents were then transferred to a reparatory funnel with 10 mL of EtOAc and the organic phase was collected. The aqueous layer was extracted with 2×20 mL of EtOAc. The combined organic extracts were washed with 15 mL of saturated aqueous NaCl, dried over $Na_2SO_4$, filtered and concentrated under reduced pressure to a yellow oil. Purification of this material by chromatography on silica gel (gradient elution: 50→75% EtOAc/hexanes) afforded secondary alcohol 24 as a clear oil (145 mg, 76%, single diastereomer). TLC $R_f$=0.36 (1:1:1 EtOAc/hexanes/$CH_2Cl_2$); $^1$H NMR ($CDCl_3$, 400 MHz) δ 7.33 (d, 1H, J=1.9 Hz), 6.35 (d, 1H, J=1.9 Hz), 5.82 (ddt, 1H, J=16.8, 10.9, 5.6 Hz), 5.71 (s, 1H), 5.21-5.16 (m, 2H), 5.09 (d, 1H, J=10.4 Hz), 4.85 (d, 1H, J=6.9 Hz), 4.82 (d, 1H, J=4.7 Hz), 4.62 (d, 1H, J=6.9 Hz), 4.26 (q, 1H, J=6.3 Hz), 4.15 (s, 1H), 3.84 (d, 2H, J=5.4 Hz), 3.35 (s, 3H), 3.30 (dd, 1H, J=14.2, 6.7 Hz), 3.10 (dd, 1H, J=14.2, 6.3 Hz), 2.75-2.61 (m, 2H), 2.29 (d, 1H, J=15.7 Hz), 2.13 (dd, 1H, J=15.8, 5.3 Hz), 1.36 (s, 9H), 1.28 (d, 3H, J=6.4 Hz) ppm; $^{13}$C NMR ($CDCl_3$, 100 MHz) δ 156.2, 150.2, 149.8, 143.4, 134.8, 125.0, 122.7, 116.9, 109.6, 95.1, 84.4, 79.0, 66.9, 63.7, 61.7, 56.1, 55.6, 45.5, 44.4, 32.5, 28.6, 23.0 ppm; IR (thin film) ν 3448, 2926, 2853, 1701, 1149, 1083 cm$^{-1}$; HRMS (ES$^+$) calcd $C_{24}H_{35}NO_7$ 472.2312. found 472.2308 (MNa$^+$). The stereochemistry at C20 was assigned based on 1D NOE correlations.

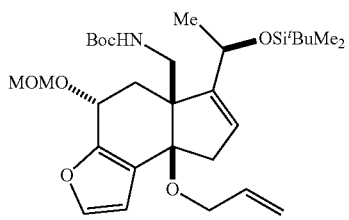

24A

To a −78° C. solution of alcohol 24 (80 mg, 0.18 mmol) in 1.8 mL of $CH_2Cl_2$ was added 2,6-lutidine (83 mL, 0.72 mmol, 4.0 equiv) and $^t$BuMe$_2$SiOTf (82 mL, 0.36 mmol, 2.0 equiv). The reaction was stirred at −78° C. for 2 h then quenched by the addition of 5 mL of saturated aqueous $NH_4Cl$. The mixture was transferred to a separatory funnel with 5 mL of $CH_2Cl_2$. The organic phase was collected and the aqueous layer was extracted with 4×10 mL of $CH_2Cl_2$. The combined organic extracts were dried over $Na_2SO_4$, filtered and concentrated under reduced pressure to a clear oil. Purification of this material by chromatography on silica gel (10% EtOAc/hexanes) yielded the desired product as a clear oil, which solidified upon standing (100 mg, 99%). TLC $R_f$=0.70 (30% EtOAc/hexanes); $^1$H NMR ($CDCl_3$, 400 MHz) δ 7.35 (d, 1H, J=1.9 Hz), 6.37 (d, 1H, J=1.9 Hz), 5.93-5.83 (m, 1H), 5.63 (t, 1H, J=1.5 Hz), 5.49 (dd, 1H, J=9.0, 3.3 Hz), 5.24 (dq, 1H, J=17.2, 1.6 Hz), 5.13 (dd, 1H, J=10.5, 1.4 Hz), 4.90 (d, 1H, J=6.8 Hz), 4.84-4.80 (m, 2H), 4.71 (d, 1H, J=6.8 Hz), 3.93 (d, 2H, J=5.3 Hz), 3.62 (dd, 1H, J=14.2, 9.1 Hz), 3.43 (s, 3H), 3.18 (dd, 1H, J=14.3, 3.6 Hz), 2.74 (dt, 1H, J=15.7, 2.2 Hz), 2.63 (dt, 1H, J=15.7, 2.2 Hz), 2.39 (dd, 1H, J=15.5, 6.0 Hz), 2.01 (dd, 1H, J=15.5, 2.0 Hz), 1.45 (br d, 9H), 1.36 (d, 3H, J=6.5 Hz), 0.84 (s, 9H), −0.07 (s, 3H), −0.15 (s, 3H) ppm; $^{13}$C NMR ($CDCl_3$, 100 MHz) δ 156.6, 150.9, 150.7, 142.6, 135.1, 122.7, 121.9, 116.5, 109.5, 95.5, 85.7, 78.8, 67.2, 66.5, 64.6, 55.6, 54.6, 43.3, 40.3, 31.4, 25.9, 24.5, 18.4, −3.3, −5.0, −5.3 ppm; IR (thin film) ν 3456, 2930, 2856, 1715, 1498, 1172, 1084, 1042 cm$^{-1}$; HRMS (ES$^+$) calcd $C_{30}H_{49}NO_7Si$ 586.3176. found 586.3172 (MNa$^+$).

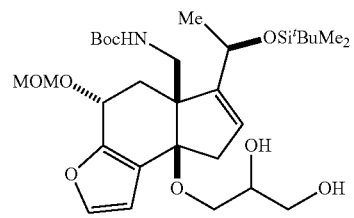

24B

To a solution of 24A (208 mg, 0.37 mmol) in 1.5 mL of THF were added sequentially N-methylmorpholine N-oxide (60 mg, 0.52 mmol, 1.4 equiv) and $OsO_4$ (330 mL of a 4 wt % solution in $H_2O$, 52 μmol, 0.14 equiv). The light yellow mixture was stirred for 4 h and the reaction was then quenched by the addition of 5 mL of saturated aqueous $Na_2S_2O_3$. The contents were transferred to a separatory funnel with 5 mL of EtOAc. The organic phase was collected and the aqueous layer was extracted with 3×10 mL of EtOAc. The combined organic extracts were washed with 10 mL of saturated aqueous $Na_2S_2O_3$, dried over $Na_2SO_4$, filtered and concentrated under reduced pressure to an off-white foam. This material (~1:1 mixture of diastereomers) was deemed pure by $^1$H NMR and used immediately in the subsequent reaction. TLC $R_f$=0.30 (5% MeOH/$CH_2Cl_2$); $^1$H NMR ($CDCl_3$, 500 MHz, mixture of diol diastereomers) δ 7.32-7.30 (m, 2H), 6.32-6.31 (m, 2H), 5.73 (s, 2H), 5.15-5.08 (m, 2H), 4.88-4.86 (m, 2H), 4.81-4.78 (m, 2H), 4.73-4.68 (m, 3H), 4.64-4.62 (m, 2H), 4.28 (m, 1H), 3.92-3.81 (m, 2H), 3.73-3.67 (m, 2H), 3.56-3.51 (m, 3H), 3.44-3.39 (m, 2H), 3.39-3.37 (m, 6H), 3.32-3.31 (m, 1H), 3.28-3.27 (m, 2H), 2.89-2.82 (m, 2H), 2.79-2.74 (m, 2H), 2.61-2.52 (m, 4H), 2.07-1.93 (m, 4H), 1.40-1.39 (m, 18H), 1.26-1.25 (m, 6H), 0.81 (m, 18H), −0.09-0.10 (m, 6H), −0.15-0.16 (m, 6H) ppm; $^{13}$C NMR ($CDCl_3$, 125 MHz, mixture of diol diastereomers) δ 156.44, 156.38, 150.78, 150.60, 148.96, 148.91, 143.1, 142.9, 124.41, 124.39, 122.5, 109.51, 109.32, 95.50, 95.44, 83.9, 83.6, 79.87, 79.84, 71.4, 71.1, 68.0, 67.4, 66.95, 66.88, 64.05, 63.90, 63.73, 55.7, 54.02, 53.96, 43.75, 43.72, 43.0, 41.8, 33.7, 33.3, 28.75, 28.72, 26.0, 23.95, 23.90, 18.47, 18.45, −4.89, −4.92, −5.27, −5.34 ppm; IR (thin film) ν 3418, 2931, 2858, 1760, 1698, 1367, 1253, 1170, 1094, 1038 cm$^{-1}$; HRMS (ES$^+$) calcd $C_{30}H_{51}NO_9Si$ 620.3231. found 620.3228 (MNa$^+$).

25

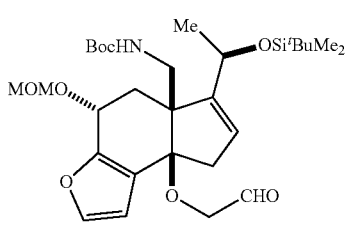

To a solution of diol 24B (28 mg, 47 mmol) in 1.0 mL of $CH_2Cl_2$ was added solid $Pb(OAc)_4$ (21 mg, 47 mmol, 1.0 equiv) in a single portion. The solution changed from clear to light peach in color and became opaque within 10 seconds following this addition. The mixture was stirred for 30 min and the reaction was then quenched by the addition of 3 mL of saturated aqueous $Na_2S_2O_3$. The contents were transferred to a separatory funnel with 5 mL of $CH_2Cl_2$. The organic phase was collected and the aqueous layer was extracted with 3×5 mL of $CH_2Cl_2$. The combined organic extracts were washed with 5 mL of saturated aqueous NaCl, dried over $Na_2SO_4$, filtered through Celite and concentrated under reduced pressure to an off-white foam. Purification of this material by chromatography on silica gel (60% EtOAc/hexanes) afforded aldehyde 25 as a white foam (25 mg, 91% over 2 steps). TLC $R_f$=0.56 (60% EtOAc/hexanes); $^1$H NMR ($CDCl_3$, 400 MHz) δ 9.62 (s, 1H), 7.35 (d, 1H, J=1.9 Hz), 6.32 (d, 1H, J=1.9 Hz), 5.84 (dd, 1H, J=9.4, 2.9 Hz), 5.63 (br s, 1H), 4.87 (d, 2H, J=6.9 Hz), 4.83-4.78 (m, 3H), 4.69 (d, 2H, J=6.9 Hz), 4.19-4.11 (m, 2H), 3.69 (dd, 1H, J=14.4, 9.5 Hz), 3.41 (s, 3H), 3.13 (dd, 1H, J=14.4, 3.2 Hz), 2.71-2.59 (m, 2H), 2.38 (dd, 1H, J=15.6, 6.0 Hz), 2.02 (dd, 1H, J=15.5, 2.1 Hz), 1.43 (s, 9H), 1.36 (d, 3H, J=6.6 Hz), 0.82 (s, 9H), −0.09 (s, 3H), −0.17 (s, 3H) ppm; $^{13}$C NMR ($CDCl_3$, 125 MHz) δ 199.3, 156.8, 151.24, 151.06, 143.0, 122.5, 120.8, 109.1, 95.5, 86.0, 79.0, 71.6, 67.2, 64.4, 55.7, 54.7, 43.4, 39.7, 31.0, 28.7, 26.0, 24.5, 18.4, −4.9, −5.3 ppm; IR (thin film) ν 3404, 2930, 2856, 1708, 1508, 1251, 1094, 1030 cm$^{-1}$; HRMS (ES$^+$) calcd $C_{29}H_{47}NO_8Si$ 588.2969. found 588.2969 (MNa$^+$).

26

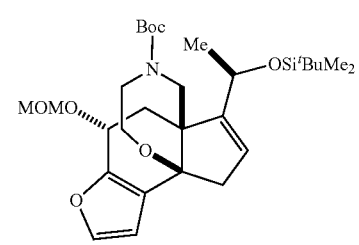

26A

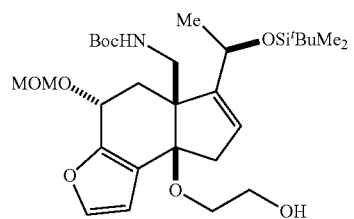

To a solution of aldehyde 25 (216 mg, 0.38 mmol) in 4.4 mL of $CH_2Cl_2$ was added 0.2 mL of AcOH (3.4 mmol, 9 equiv) and $MgSO_4$ (210 mg, 1.74 mmol, 4.6 equiv). The suspension was stirred for 2.5 h and then solid $NaBH_3CN$ (48 mg, 0.76 mmol, 2 equiv) was added in a single portion. The contents were stirred for 1 h, after which time additional $NaBH_3CN$ (36 mg, 0.57 mmol, 1.5 equiv) and $MgSO_4$ (40 mg, 0.33 mmol, 0.9 equiv) was added. Following an additional 12 h of stirring, the reaction was quenched by the addition of 10 mL of saturated aqueous $NaHCO_3$. Upon cessation of gas evolution, the mixture was transferred to reparatory funnel with 10 mL of EtOAc. The organic phase was collected and the aqueous layer was extracted with 3×8 mL of EtOAc. The combined organic extracts were dried over $Na_2SO_4$, filtered and concentrated under reduced pressure to a white foam. Purification of this material by chromatography on silica gel (gradient elution: 20→50% EtOAc/hexanes) afforded tertiary carbamate 26 (155 mg) as a white foam and alcohol 26A (34 mg) as a clear oil (90% combined yield). Tertiary carbamate 26: TLC $R_f$=0.64 (40% EtOAc/hexanes); $^1$H NMR ($CDCl_3$, 400 MHz) δ 7.38 (s, 1H), 6.38 (d, 1H, J=1.7 Hz), 5.62 (s, 1H), 4.84 (s, 2H), 4.78 (d, 1H, J=0.6 Hz), 4.62 (d, 1H, J=6.8 Hz), 4.23-4.08 (m, 2H), 3.92-3.88 (m, 1H), 3.46 (d, 1H, J=13.3 Hz), 3.39 (s, 3H), 3.31-3.13 (m, 3H), 3.05 (t, 1H, J=12.4 Hz), 2.89 (d, 1H, J=16.8 Hz), 2.61 (d, 1H, J=16.8 Hz), 2.20 (q, 2H, J=9.7 Hz), 1.50-1.39 (m, 12H), 0.87 (s, 9H), 0.02 (s, 3H), −0.05 (d, 3H, J=5.4 Hz) ppm. $^{13}$C NMR ($CDCl_3$, 125 MHz, mixture of rotameric isomers) δ 155.95, 155.82, 151.4, 151.0, 149.7, 149.0, 143.58, 143.45, 123.86, 123.71, 122.7, 122.1, 108.64, 108.59, 95.1, 94.9, 86.92, 86.85, 80.6, 79.9, 66.83, 66.69, 64.32, 64.20, 63.9, 57.7, 57.3, 55.54, 55.43, 49.3, 48.60, 48.54, 48.0, 45.2, 31.65, 31.63, 31.3, 28.9, 28.6, 26.1, 25.0, 24.5, 18.3, −4.63, −4.65, −4.69, −4.77 ppm; IR (thin film) ν 2929, 2855, 1693, 1421, 1251, 1139 1097, 1051 cm$^{-1}$; HRMS (ES$^+$) calcd $C_{29}H_{47}NO_7Si$ 572.3020. found 572.3016 (MNa$^+$). Primary alcohol 26A: TLC $R_f$=0.27 (40% EtOAc/hexanes); $^1$H NMR ($CDCl_3$, 600 MHz) δ 7.35 (d, 1H, J=1.4 Hz), 6.37 (s, 1H), 5.79 (s, 1H), 5.05 (d, 1H, J=10.3 Hz), 4.91 (d, 1H, J=6.8 Hz), 4.85-4.84 (m, 1H), 4.76 (d, 1H, J=5.4 Hz), 4.67 (d, 1H, J=6.8 Hz), 4.19 (s, 1H), 4.00 (dd, 1H, J=13.7, 10.8 Hz), 3.64 (s, 2H), 3.42 (s, 3H), 3.38 (s, 2H), 2.78 (d, 1H, J=13.8 Hz), 2.60 (s, 2H), 2.09 (dd, 1H, J=15.5, 5.8 Hz), 2.02 (t, 1H, J=13.7 Hz), 1.44 (s, 9H), 1.29 (d, 3H, J=6.5 Hz), 0.86 (s, 9H), −0.05 (s, 3H), −0.12 (s, 3H) ppm; $^{13}$C NMR ($CDCl_3$, 150 MHz) δ 156.4, 150.6, 148.9, 142.8, 124.5, 122.7, 109.6, 95.5, 83.3, 79.8, 68.1, 66.9, 64.0, 62.4, 55.7, 54.0, 43.8, 42.4, 33.5, 28.7, 26.0, 23.9, 18.5, −4.9, −5.3 ppm; IR (thin film) ν 3435, 2929, 2856, 1707, 1510, 1250, 1172, 1094, 1048, 1032 cm$^{-1}$; HRMS (ES$^+$) calcd $C_{29}H_{49}NO_8Si$ 590.3125. found 590.3124 (MNa$^+$).

Alternative method for the preparation of 26: To an ice-cold solution of alcohol 26A (37 mg, 65 mmol) in 1.0 mL of $CH_2Cl_2$ was added $Et_3N$ (45 mL, 0.32 mmol, 5 equiv) and methanesulfonyl chloride (15 mL, 0.19 mmol, 3 equiv). The reaction was stirred at 0° C. for 30 min and then quenched by the addition of 6 mL of saturated aqueous $NH_4Cl$. The solution was transferred to a separatory funnel with 6 mL of $CH_2Cl_2$ and 4 mL of $H_2O$. The organic phase was collected and the aqueous phase was extracted with 3×5 mL of $CH_2Cl_2$. The combined organic extracts were dried over $Na_2SO_4$, filtered and concentrated under reduced pressure to a yellow oil. Purification of this material by chromatography on silica gel (40% EtOAc/hexanes) afforded the methanesulfonate product as a clear oil (32 mg, 76%). TLC $R_f$=0.51 (51% EtOAc/hexanes). The methanesulfonate product was immediately dissolved in 2.0 mL of THF and to this solution was added KO$^t$Bu (0.66 mL of a 0.3 M solution in THF, 0.20 mmol, 4.0 equiv). The resulting yellow mixture was stirred for 4 h and then diluted with 5 mL of saturated aqueous $NH_4Cl$. The contents were transferred to a separatory funnel with 5 mL of EtOAc. The organic phase was collected and the aqueous layer was extracted with 3×5 mL of EtOAc. The combined organic extracts were dried over Na₂SO₄, filtered and concentrated under reduced pressure to a yellow oil. Purification of this material by chromatography on silica gel (20% EtOAc/hexanes) afforded tertiary carbamate 26 as a white foam (23 mg, 86%).

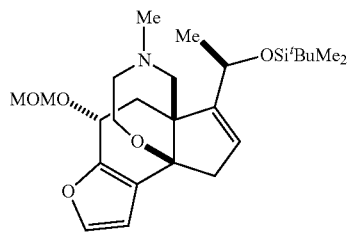

27

To a solution of tertiary carbamate 26 (32 mg, 0.59 mmol) in 1.0 mL of THF was added LiAlH₄ (0.24 mL of a 1.0 M solution in THF, 0.24 mmol, 4 equiv). The solution was stirred for 20 min and then heated to 65° C. and stirred for an additional 3.5 h. Following this time, the mixture was cooled to room temperature and H₂O (10 mL), 15% v/v aqueous NaOH (10 mL), and H₂O (30 mL) were added successively. The resulting white, opaque suspension was filtered through a small pad of Celite, rinsing the flask and filter cake with ~10 mL of Et₂O. The combined filtrates were concentrated under reduced pressure to a yellow solid. Purification of this material by chromatography on silica gel (30% EtOAc/hexanes) afforded tertiary amine 27 as a white crystalline solid (20 mg, 73%). TLC R$_f$=0.60 (40% EtOAc/hexanes); ¹H NMR (CDCl₃, 600 MHz) δ 7.36 (s, 1H), 6.36 (s, 1H), 5.61 (s, 1H), 4.87 (d, 2H, J=6.0 Hz), 4.68 (t, 2H, J=7.8 Hz), 3.46-3.44 (m, 1H), 3.41 (s, 3H), 3.39-3.35 (m, 1H), 2.92 (dd, 1H, J=14.8, 5.3 Hz), 2.83-2.79 (m, 2H), 2.70-2.63 (m, 1H), 2.55-2.47 (m, 2H), 2.32 (s, 3H), 1.90 (dd, 1H, J=15.0, 4.9 Hz), 1.35 (d, 3H, J=6.4 Hz), 0.89 (s, 9H), 0.06 (s, 3H), 0.01 (s, 3H) ppm; ¹³C NMR (CDCl₃, 125 MHz) δ 151.3, 143.3, 123.9, 122.6, 108.8, 95.3, 86.7, 66.7, 65.1, 63.9, 61.2, 60.8, 58.3, 55.6, 48.3, 45.4, 37.3, 29.9, 26.2, 24.7, 18.4, −4.17, −4.35 ppm; IR (thin film) v 2930, 2855, 1462, 1253, 1150, 1095, 1052, 1019 cm⁻¹; HRMS (ES⁺) calcd C₂₅H₄₁NO₅Si 486.2652. found 486.2644 (MNa⁺).

Experimental Procedures and Characterization Data for Select Dienophile Precursors:

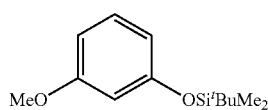

S1

To a solution of 3-methoxyphenol (1.7 g, 13.8 mmol) and ᵗBuMe₂SiCl (2.7 g, 18.0 mmol, 1.3 equiv) in 12.6 mL of DMF was added solid imidazole (1.5 g, 22.0 mmol, 1.6 equiv) in a single portion. Following the addition, the solution was stirred for 45 min. The reaction was quenched by the addition of 70 mL of H₂O and diluted with 20 mL of Et₂O. The contents were transferred to a reparatory funnel with 20 mL of Et₂O. The organic phase was collected and the aqueous layer was extracted with 3×75 mL of Et₂O. The combined organic extracts were washed with 1×25 mL of saturated aqueous NaCl, dried over MgSO₄, filtered, and concentrated under reduced pressure to furnish a yellow oil. Purification of this material by chromatography on silica gel (gradient elution: 3→8% EtOAc/hexanes) afforded silyl ether S1 as a clear oil (2.9 g, 88%). TLC R$_f$=0.43 (5% EtOAc/hexanes); ¹H NMR (CDCl₃, 500 MHz) δ 7.13 (t, 1H, J=8.2 Hz), 6.53 (dd, 1H, J=8.3, 2.4 Hz), 6.46 (dd, 1H, J=8.0, 2.2 Hz), 6.41 (t, 1H, J=2.3 Hz), 3.78 (s, 3H), 0.99 (s, 9H), 0.21 (s, 6H) ppm; ¹³C NMR (CDCl₃, 125 MHz) δ 160.9, 157.1, 129.9, 112.8, 107.0, 106.6, 55.5, 25.9, 18.5, −4.1 ppm; IR (thin film) v 2956, 2932, 2859, 1600, 1491, 1290, 1270, 1202, 1152, 976, 841 cm⁻¹; HRMS (ES⁺) calcd C₁₃H₂₂O₂Si 239.1467. found 239.1459 (MH⁺).

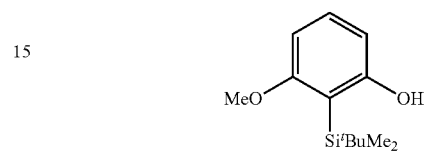

S2

To a −78° C. solution of diisopropylamine (5.2 mL, 36.9 mmol, 4.1 equiv) in 50 mL of THF was added nBuLi (14.4 mL of a 2.5M solution in hexanes, 36 mmol, 4.0 equiv). The mixture was stirred at −78° C. for 30 min, warmed to 0° C. for 20 min, and then re-cooled to −78° C. before a solution of silyl ether S1 (2.15 g, 9.00 mmol) in 20 mL of THF was added dropwise via cannula. Transfer of this material was made quantitative with 5 mL of THF. The solution was warmed to room temperature and then heated to 63° C. for 30 min. Following this time, the solution was cooled to room temperature and the reaction was quenched by addition of 75 mL of saturated aqueous NH₄Cl and 75 mL of Et₂O. The contents were transferred to a reparatory funnel with 40 mL of Et₂O and the organic phase was collected. The aqueous layer was extracted with 3×80 mL of Et₂O. The combined organic extracts were dried over MgSO₄, filtered and concentrated under reduced pressure to furnish a yellow oil. Purification of this material by chromatography on silica gel (5→8% EtOAc/hexanes) afforded phenol S2 as a pale yellow solid (1.19 g, 56%). TLC R$_f$=0.32 (8% EtOAc/hexanes); ¹H NMR (CDCl₃, 400 MHz) δ 7.19 (t, 1H, J=8.1 Hz), 6.43 (dd, 1H, J=8.2, 0.4 Hz), 6.36 (dd, 1H, J=8.0, 0.8 Hz), 5.01 (s, 1H), 3.73 (s, 3H), 0.92 (s, 9H), 0.37 (s, 6H) ppm; ¹³C NMR (CDCl₃, 100 MHz) δ 166.1, 162.2, 131.7, 110.0, 108.8, 102.7, 55.1, 27.1, 18.6, −1.7 ppm; IR (thin film) v 3533, 2954, 2895, 2855, 1592, 1457, 1431, 1250, 1077, 826, 777 cm⁻¹.

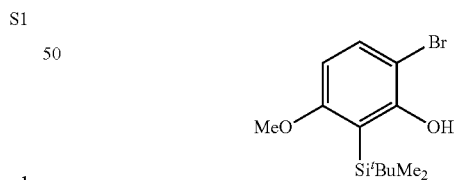

S3

To a solution of phenol S2 (674 mg, 2.83 mmol) in 31 mL of deoxygenated THF (sparged with N₂ gas for 1 h) at −40° C. was added N-bromosuccinimide (327 mg, 1.84 mmol, 0.65 equiv) in the dark. After stirring this mixture for 10 min, an additional portion of N-bromosuccinimide was added (327 mg, 1.84 mmol, 0.65 equiv). The resultant bright yellow solution was stirred in the dark at −40° C. for 50 min. The reaction was then quenched by addition of 20 mL of saturated aqueous Na₂S₂O₃ and warmed to room temperature. The contents were transferred to a separatory funnel with 20 mL of Et₂O and the organic phase was collected. The aqueous layer was extracted with 3×30 mL of Et$_2$O. The combined organic extracts were washed with 1×15 mL of saturated aqueous Na$_2$S$_2$O$_3$, dried over MgSO$_4$, filtered and concentrated under reduced pressure to a yellow oil. Purification of this material by chromatography on silica gel (100% heptanes) yielded phenol S3 a clear oil (362 mg, 40%). TLC R$_f$=0.41 (100% heptanes); $^1$H NMR (CDCl$_3$, 400 MHz) δ 7.39 (d, 1H, J=8.7 Hz), 6.34 (d, 1H, J=8.8 Hz), 5.68 (s, 1H), 3.72 (s, 3H), 0.91 (s, 9H), 0.34 (s, 6H) ppm; $^{13}$C NMR (CDCl$_3$, 100 MHz) δ 165.6, 157.3, 133.4, 112.2, 104.4, 102.8, 55.3, 27.1, 18.7, −1.6 ppm; IR (thin film) v 3512, 2954, 2894, 2854, 1580, 1459, 1414, 1303, 1279, 1240, 1081, 827 cm$^{-1}$.

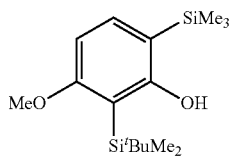

S4

To a solution of phenol S3 (237 mg, 0.75 mmol) and Me$_3$SiCl (244 mg, 2.25 mmol, 3.0 equiv) in 7.5 mL of CH$_2$Cl$_2$ was added imidazole (3.0 mL of a 1.0 M solution in CH$_2$Cl$_2$, 3.0 mmol, 4.0 equiv). Following the addition, the solution was stirred for 1 h. The reaction was then quenched by the addition of 8 mL of H$_2$O and diluted with 10 mL of Et$_2$O. The contents were transferred to a separatory funnel with 10 mL of Et$_2$O. The organic phase was collected and the aqueous layer was extracted with 3×10 mL of Et$_2$O. The combined organic extracts were washed with 1×15 mL of saturated aqueous NaCl, dried over MgSO$_4$, filtered and concentrated under reduced pressure to furnish the trimethylsilyl ether as a white, crystalline solid. This material was deemed pure by $^1$H NMR and used immediately in the subsequent reaction.

To a −78° C. solution of trimethylsilyl ether in 10 mL of Et$_2$O was added $^t$BuLi dropwise over 1 min. The solution was warmed slowly to 0° C. over 2.5 h, following which time the reaction was quenched by addition of 20 mL of saturated aqueous NH$_4$Cl. The mixture was warmed to room temperature and the contents then transferred to a separatory funnel with 20 mL of Et$_2$O. The organic phase was collected and the aqueous layer was extracted with 3×10 mL of Et$_2$O. The combined organic extracts were washed with 1×10 mL of saturated aqueous NH$_4$Cl, dried over MgSO$_4$, filtered and concentrated under reduced pressure to a white solid. Purification of this material by chromatography on silica gel (100% hexanes→1% Et$_2$O/hexanes) afforded phenol S4 as a white, crystalline solid (164 mg, 71% over 2 steps). TLC R$_f$=0.39 (100% hexanes); $^1$H NMR (CDCl$_3$, 500 MHz) δ 7.35 (d, 1H, J=8.1 Hz), 6.45 (d, 1H, J=8.1 Hz), 5.47 (s, 1H), 3.73 (s, 3H), 0.93 (s, 9H), 0.42 (s, 6H), 0.28 (s, 9H) ppm; $^{13}$C NMR (CDCl$_3$, 125 MHz) δ 167.5, 167.2, 138.2, 117.6, 108.1, 102.4, 54.9, 27.1, 18.7, −0.5, −1.6 ppm; IR (thin film) v 3594, 2956, 2856, 1579, 1559, 1460, 1368, 1243, 1197, 1173, 1114, 1080, 839 cm$^{-1}$.

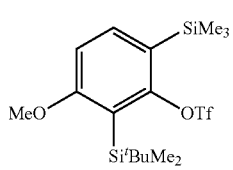

S5

To an ice-cold suspension of NaH (15 mg, 0.63 mmol, 1.6 equiv) in 1 mL of DMF was added dropwise via cannula a solution of phenol S4 (123 mg, 0.40 mmol) in 2 mL of DMF. Transfer of this material was made quantitative with 1 mL of DMF. After stirring this mixture for 50 min at 0° C., PhNTf$_2$ was added (1.0 mL of a 0.44 M solution in DMF, 0.44 mmol, 1.1 equiv). The flask was removed from the ice bath and the reaction was warmed to room temperature. The reaction was stirred for 2 h at this temperature then quenched by addition of 10 mL of saturated aqueous NH$_4$Cl. The contents were transferred to a separatory funnel with 15 mL of Et$_2$O and 5 mL of H$_2$O. The organic phase was collected and the aqueous layer was extracted with 3×10 mL of Et$_2$O. The combined organic extracts were washed with 1×10 mL of saturated aqueous NH$_4$Cl, dried over MgSO$_4$, filtered and concentrated under reduced pressure to an orange crystalline solid. Purification of this material by chromatography on silica gel (100% hexanes→4% EtOAc/hexanes) afforded aryl triflate S5 as a light orange, crystalline solid (154 mg, 88%). TLC R$_f$=0.51 (2% EtOAc/hexanes); $^1$H NMR (CDCl$_3$, 500 MHz) δ 7.53 (d, 1H, J=8.2 Hz), 6.86 (d, 1H, J=8.2 Hz), 3.81 (s, 3H), 0.91 (s, 9H), 0.33 (s, 6H), 0.32 (s, 6H) ppm; $^{13}$C NMR (CDCl$_3$, 125 MHz) δ 166.5, 155.9, 139.3, 126.5, 122.3, 118.7 (q, T$_{CF}$=319 Hz), 109.6, 55.2, 28.6, 18.3, 0.7, −0.7 ppm; IR (thin film) v 2931, 2855, 1581, 1392, 1251, 1211, 1137, 1039, 842 cm$^{-1}$.

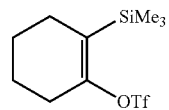

S6

To a −78° C. solution of 2-(trimethylsilyl)cyclohex-2-enone (Shih et al., *J. Org. Chem.* 1980, 45, 4462-4471) (190 mg, 1.13 mmol) in 4 mL of THF was added 1-selectride (1.15 mL of a 1.0 M solution in THF, 1.15 mmol, 1.02 equiv). The reaction was stirred at −78° C. for 3.5 h. Following this time, a solution of PhNTf$_2$ (484 mg, 1.36 mmol, 1.2 equiv) in 1 mL of THF was added dropwise via syringe. The resulting clear solution was warmed to room temperature and stirred for an additional 13 h, during which time the mixture became light yellow. The reaction was quenched with 10 mL of saturated aqueous NH$_4$Cl and the contents were transferred to a repatory funnel with 20 mL of Et$_2$O and 10 mL of H$_2$O. The organic phase was collected and the aqueous layer was extracted with 3×10 mL of Et$_2$O. The combined organic extracts were dried over MgSO$_4$, filtered and concentrated under reduced pressure to a yellow oil. Purification of this material by chromatography on silica gel (24% Et$_2$O/hexanes) afforded vinyl triflate S6 (Atanes et al., *Tetrahedron Lett.* 1998, 39, 3039-3040) as a clear oil (130 mg, 38%). TLC R$_f$=0.68 (5% Et$_2$O/hexanes); $^1$H NMR (CDCl$_3$, 400 MHz) δ 2.39 (tt, 2H, J=6.0, 2.8 Hz), 2.19 (tt, 2H, J=5.7, 2.8 Hz), 1.78-1.72 (m, 2H), 1.60-1.54 (m, 2H), 0.18 (s, 9H) ppm; $^{13}$C NMR (CDCl$_3$, 100 MHz) δ 154.7, 128.1, 118.5 (q, T$_{CF}$=318 Hz), 28.63, 28.47, 23.2, 22.0, −1.1 ppm; IR (thin film) v 2949, 1652, 1411, 1248, 1209, 1145, 989, 895, 841 cm$^{-1}$; HRMS (ES$^+$) calcd C$_{10}$H$_{17}$F$_3$O$_3$SSi 325.0518. found 325.0512 (MNa$^+$).

Experimental Procedures and Characterization Data for Diels-Alder Adducts (Schemes 6 and 7):

General Method for Regio- and Stereochemical Assignment of Diels-Alder Adducts.

Regio- and stereochemical assignments were based on $^1$H NOE analysis where indicated. In cycloaddition reactions with tetracycle 26, characteristic H11 shifts ranging from 5.0-5.4 ppm were noted for the desired α-oxo-bridged products. By contrast, H11 chemical shifts of 4.3-4.5 ppm are measured for structurally equivalent 3-oxo-bridged isomers. The characteristic resonance frequency of H11 was used in subsequent product analyses to tentatively assign α vs. β-oxo bridge stereochemistry. In Diels-Alder reactions with intermediate 21, NOE experiments from initial experiments confirmed that cycloaddition occurred exclusively from the β-face of the furan. For all other cycloaddition reactions with 21, the oxo-bridged stereochemistry was assigned by analogy. Note: For many compounds, $^1$H NMR spectra of Diels-Alder products displayed mixtures of rotameric isomers. In select instances, peak signals coalesced by performing $^1$H NMR analysis at elevated temperature (as noted). For certain products, resolution of the $^1$H NMR spectra was not possible even when recorded at high temperature. Data for these compounds are reported from analyses performed at ambient temperature.

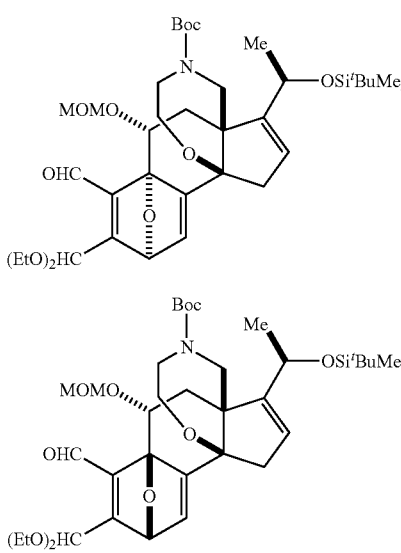

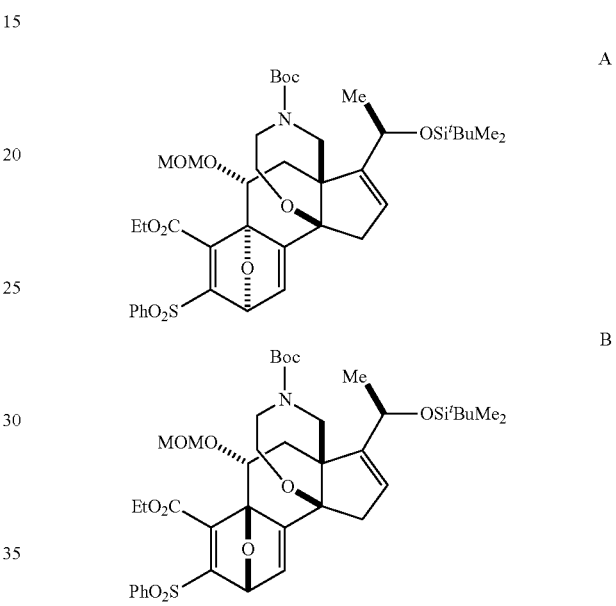

Entry 1, Scheme 6:

A suspension of furan 26 (12.5 mg, 23 mmol), 4,4-diethoxybut-2-ynal (57 mg, 0.37 mmol, 16 equiv), di-t-butylhydroxytoluene (0.5 mg, 23 mmol, 0.1 equiv), and $Na_2CO_3$ (2.5 mg, 23 mmol, 1.0 equiv) was stirred in the dark at 90° C. for 21 h. Following this time, the orange-brown mixture was cooled to room temperature and filtered through Celite. The flask and filter cake were washed with ~10 mL of $CH_2Cl_2$, and the combined filtrates were concentrated under reduced pressure to a brown oil. Purification of this material by chromatography on silica gel (15→30% EtOAc/hexanes) afforded cycloadduct A (3.5 mg) as a yellow oil and cycloadduct B (3.5 mg) as a yellow oil (42% combined yield). Isomer A: TLC $R_f$=0.37 (40% EtOAc/hexanes); $^1$H NMR (CDCl$_3$, 600 MHz, 45° C.) δ 10.14 (s, 1H), 6.54 (s, 1H), 5.70 (s, 1H), 5.57 (s, 1H), 5.43 (s, 1H), 5.35-5.34 (m, 1H), 4.74-4.71 (m, 2H), 4.34 (s, 1H), 4.06-4.04 (m, 2H), 3.77-3.72 (m, 2H), 3.68-3.56 (m, 4H), 3.53-3.48 (m, 3H), 3.32 (s, 3H), 2.93 (d, 1H, J=16.7 Hz), 2.22-2.13 (m, 2H), 1.83 (t, 1H, J=12.4 Hz), 1.50 (s, 9H), 1.34-1.33 (m, 3H), 1.24-1.18 (m, 6H), 0.88 (s, 9H), 0.03-0.02 (m, 6H) ppm; IR (thin film) ν 2930, 1692, 1367, 1251, 1055 cm$^{-1}$. Isomer B: TLC $R_f$=0.51 (40% EtOAc/hexanes); $^1$H NMR (CDCl$_3$, 600 MHz) δ 10.14 (s, 1H), 6.81 (d, 1H, J=1.9 Hz), 5.72 (s, 1H), 5.63 (s, 1H), 5.48 (d, 1H, J=1.8 Hz), 4.71 (d, 1H, J=6.6 Hz), 4.60 (d, 1H, J=6.6 Hz), 4.56 (d, 1H, J=5.5 Hz), 4.51 (d, 1H, J=15.4 Hz), 4.23 (dd, 1H, J=13.5, 4.6 Hz), 3.83-3.78 (m, 1H), 3.60-3.53 (m, 5H), 3.50 (d, 1H, J=15.5 Hz), 3.38-3.35 (m, 1H), 3.32 (s, 3H), 3.18 (d, 1H, J=13.0 Hz), 2.50-2.48 (m, 1H), 2.37-2.33 (m, 2H), 2.12 (d, 1H, J=17.2 Hz), 1.45 (s, 9H), 1.28-1.22 (m, 6H), 1.18 (t, 3H, J=7.0 Hz), 0.91 (s, 9H), 0.22 (s, 3H), 0.14 (s, 3H) ppm; IR (thin film) ν 2929, 1692, 1367, 1251, 1053 cm$^{-1}$. Isomer A: the structure and the stereochemistry of the oxo bridge were assigned based on 1D NOE correlations. Isomer B: The stereochemistry of the oxo bridge was assigned following the general procedure outlined above.

Entry 2, Scheme 6:

A solution of furan 26 (37 mg, 67 mmol) and ethyl-3-(phenylthio)propiolate (Shen and Schultz, Tetrahedron Lett. 1981, 22, 3347-3350) (46 mg, 0.19 mmol, 2.9 equiv) in 0.6 mL of toluene was stirred at 63° C. for 5 h. Following this time, the reaction mixture was cooled to room temperature and concentrated under reduced pressure to a yellow oil. Purification of this material by chromatography on silica gel (gradient elution: 4→11% acetone/CHCl$_3$) afforded cycloadduct A as a white amorphous solid and cycloadduct B as a white foam (47 mg, 90% combined yield). Major isomer A: TLC $R_f$=0.37 (40% EtOAc/hexanes); $^1$H NMR (CDCl$_3$, 500 MHz) δ 8.04 (d, 2H, J=7.7 Hz), 7.64 (t, 1H, J=7.4 Hz), 7.55 (t, 2H, J=7.7 Hz), 6.74-6.69 (m, 1H), 5.71 (br s, 1H), 5.56-5.50 (m, 1H), 4.97 (d, 1H, J=12.3 Hz), 4.67 (d, 1H, J=6.9 Hz), 4.56 (d, 1H, J=6.9 Hz), 4.33-4.24 (m, 3H), 4.14-3.94 (m, 2H), 3.80-3.44 (m, 4H), 3.17-3.08 (m, 3H), 2.97 (d, 1H, J=17.0 Hz), 2.29-2.24 (m, 1H), 2.08 (dd, 1H, J=13.2, 3.4 Hz), 1.76-1.70 (m, 1H), 1.48-1.46 (m, 9H), 1.39-1.28 (m, 6H), 0.88-0.84 (m, 9H), −0.01-0.02 (m, 6H) ppm; IR (thin film) ν 2931, 1723, 1691, 1410, 1367, 1322, 1251, 1154, 1106, 1048 cm$^{-1}$; HRMS (ES$^+$) calcd C$_{40}$H$_{57}$NO$_{11}$SSi 810.3320. found 810.3328 (MNa$^+$). Minor isomer B: TLC $R_f$=0.44 (40% EtOAc/hexanes); $^1$H NMR (CDCl$_3$, 500 MHz) δ 7.93 (d, 2H, J=7.6 Hz), 7.68 (t, 1H, J=7.4 Hz), 7.58 (t, 2H, J=7.8 Hz), 6.79 (s, 1H), 5.78 (s, 1H), 5.41 (d, 1H, J=2.0 Hz), 4.65 (d, 1H, J=6.7 Hz), 4.54-4.44 (m, 3H), 4.33-4.37 (m, 1H), 4.25-4.20 (m, 1H), 4.13 (dd, 1H, J=13.6, 4.9 Hz), 3.70-3.65 (m, 1H), 3.56-3.54 (m, 2H), 3.36 (d, 1H, J=15.0 Hz), 3.25 (s, 3H), 3.13

(d, 1H, J=13.0 Hz), 2.97 (d, 1H, J=17.2 Hz), 2.40-2.37 (m, 1H), 2.22 (dd, 1H, J=17.3, 2.3 Hz), 2.00 (t, 1H, J=14.2 Hz), 1.43 (s, 9H), 1.31 (t, 4H, J=7.1 Hz), 1.27-1.25 (m, 6H), 0.87 (s, 9H), 0.19-0.12 (m, 6H) ppm; IR (thin film) ν 2931, 2857, 1727, 1692, 1448, 1411, 1367, 1320, 1257, 1161, 1132, 1083, 1049, 834, 776, 728, 598 cm$^{-1}$; HRMS (ES$^+$) calcd C$_{40}$H$_{57}$NO$_{11}$SSi 810.3320. found 810.3316 (MNa$^+$). Isomers A and B: The stereochemistry of each oxo bridge was assigned following the general procedure outlined above. The structure of each isomer was assigned based on 1D NOE correlations.

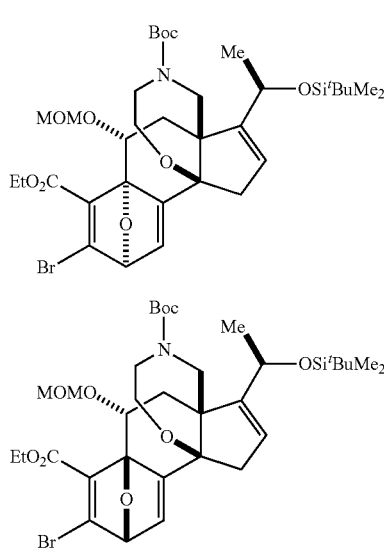

Entry 3, Scheme 6:

A suspension of furan 26 (10.5 mg, 19 mmol), ethyl bromopropiolate (39.5 mg, 0.22 mmol, 12.0 equiv), and Na$_2$CO$_3$ (8 mg, 75 mmol, 4.0 equiv) in 0.5 mL of toluene was stirred at 105° C. for 44 h. Following this time, the opaque, brown mixture was cooled to room temperature and filtered through Celite. The flask and filter cake were washed with ~15 mL of Et$_2$O. The combined filtrates were concentrated under reduced pressure to a brown oil. Purification of this material by chromatography on silica gel (15→25% EtOAc/hexanes) afforded cycloadduct A (7.5 mg, 53%) as a yellow oil and cycloadduct B (4.5 mg, 32%) as a yellow oil. Major isomer A: TLC R$_f$=0.19 (20% EtOAc/hexanes); $^1$H NMR (CDCl$_3$, 400 MHz) δ 6.68-6.63 (m, 1H), 5.71 (br s, 1H), 5.34-5.31 (m, 1H), 5.20 (d, 1H, J=1.9 Hz), 4.74 (d, 1H, J=6.7 Hz), 4.70 (d, 1H, J=6.7 Hz), 4.32-3.94 (m, 2H), 4.26 (q, 4H, J=7.1 Hz), 4.15-4.04 (m, 1H), 3.76-3.66 (m, 2H), 3.52-3.49 (m, 2H), 3.32 (s, 3H), 2.96 (d, 1H, J=16.9 Hz), 2.27-2.22 (m, 1H), 2.15-2.12 (m, 1H), 1.85-1.79 (m, 1H), 1.48 (s, 9H), 1.38-1.25 (m, 6H), 0.86 (s, 9H), 0.01 (s, 3H), 0.00 (s, 3H) ppm; IR (thin film) ν 2931, 2857, 1732, 1463, 1410, 1368, 1250, 1151, 1099, 1023 cm$^{-1}$; HRMS (ES$^+$) calcd C$_{34}$H$_{52}$BrNO$_9$Si 748.2493. found 750.2482 (MNa$^+$). Isomers A and B: The stereochemistry of each oxo bridge was assigned following the general procedure outlined above. The structure was determined through 1D NOE correlations (between H5 and H6) of the debrominated products.

General Procedure for CsF-Promoted Diels-Alder Reactions.

To a solution of furan diene and dienophile precursor (2.0-6.0 equiv) in MeCN was added solid CsF (3.0-10.0 equiv) in one portion. The suspension was stirred until thin layer chromatography indicated complete consumption of the starting furan (or the lack of additional conversion). The mixture was filtered through a small pad of dry Celite, and the flask and filter cake were rinsed with EtOAc. The combined filtrates were concentrated under reduced pressure to a thin film, which was dissolved in 19:1 Et$_2$O:EtOAc and filtered a second time through dry Celite. The filter cake was washed with a solution of 19:1 Et$_2$O/EtOAc, and the combined filtrates were concentrated under reduced pressure. Purification of the isolated material was performed by chromatography on silica gel (conditions given below).

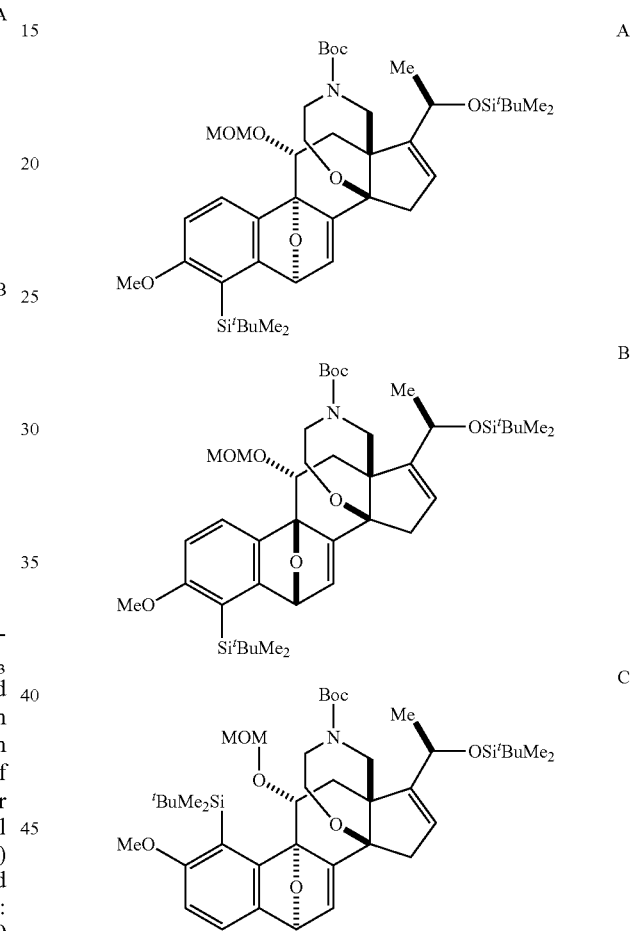

Entry 4, Scheme 6:

Reaction performed with furan 26 (14 mg, 25 mmol), benzyne precursor S5 (27 mg, 61 mmol, 2.4 equiv), CsF (20 mg, 0.131 mmol, 5.2 equiv) and 0.7 mL of MeCN. The reaction mixture was stirred for 21 h. Purification by chromatography on silica gel (15→20% EtOAc/hexanes) furnished cycloadduct A (6 mg) as a clear oil and cycloadducts B and C as a 3:5 mixture of diastereomers (13 mg, 97% combined yield). Isomer A: TLC R$_f$=0.28 (15% EtOAc/hexanes); $^1$H NMR (CDCl$_3$, 600 MHz, 45° C.) δ 7.25 (d, 1H, J=8.0 Hz), 6.59 (s, 1H), 6.38 (d, 1H, J=7.9 Hz), 5.74 (br s, 1H), 5.70 (br s, 1H), 5.01 (dd, 1H, J=11.8, 3.5 Hz), 4.74-4.67 (m, 2H), 4.43-4.39 (m, 1H), 4.08 (d, 1H, J=14.6 Hz), 3.94 (t, 1H, J=12.2 Hz), 3.70 (s, 4H), 3.50-3.40 (m, 3H), 3.32 (s, 3H), 2.88 (d, 1H, J=17.1 Hz), 2.36-2.31 (m, 1H), 2.21-2.19 (m, 1H), 2.03 (t, 1H, J=12.8 Hz), 1.50 (s, 9H), 1.36 (d, 3H, J=6.4 Hz), 0.92-0.90 (m, 18H), 0.30 (s, 3H), 0.26 (s, 3H), 0.06 (d, 6H, J=2.1

Hz) ppm; IR (thin film) ν 2928, 2856, 1695, 1462, 1407, 1366, 1246, 1152, 1106 cm$^{-1}$; HRMS (ES$^+$) calcd C$_{42}$H$_{67}$NO$_8$Si$_2$ 792.4303. found 792.4318 (MNa$^+$). The relative stereochemistry of both the oxo bridge and the $^t$BuMe$_2$Si-group were assigned based on 1D NOE correlations. Isomers B and C: the stereochemistry of the oxo bridge for each product was assigned following the general procedure outlined above. The structure of each adduct was assigned based on 1D NOE correlations.

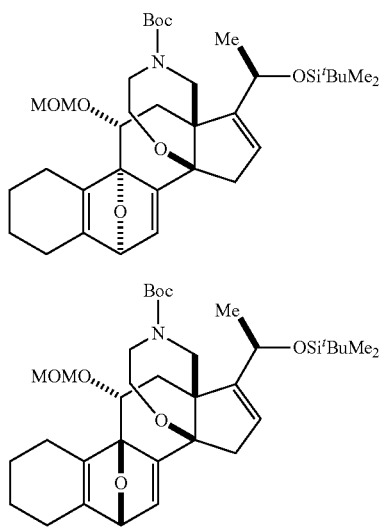

A

B

Entry 5, Scheme 6:

Reaction performed with furan 26 (11 mg, 25 mmol), cyclohexyne precursor S6 (21 mg, 69 mmol, 3.3 equiv), CsF (31 mg, 0.20 mmol, 9.9 equiv) and 0.5 mL of MeCN. The reaction mixture was stirred for 17 h. Purification by chromatography on silica gel (15→20% EtOAc/hexanes) afforded cycloadducts A (3 mg) as a clear oil and B (1 mg) as a clear oil (30% combined yield). Isomer A: TLC R$_f$=0.24 (20% EtOAc/hexanes); $^1$H NMR (CDCl$_3$, 600 MHz, 45° C.) δ 6.58 (s, 1H), 5.70 (s, 1H), 5.05 (s, 1H), 4.72-4.61 (m, 3H), 4.37-4.36 (m, 1H), 4.07 (br s, 1H), 3.96 (d, 1H, J=14.9 Hz), 3.69-3.60 (m, 2H), 3.50-3.48 (m, 2H), 3.38 (s, 3H), 2.93 (d, 1H, J=17.0 Hz), 2.40-2.28 (m, 3H), 2.16 (s, 1H), 2.11-2.04 (m, 3H), 1.91-1.85 (m, 2H), 1.67 (br s, 2H), 1.49 (s, 9H), 1.33 (d, 3H, J=6.2 Hz), 0.88 (s, 9H), 0.03 (d, 6H, J=5.6 Hz) ppm; IR (thin film) ν 2929, 2856, 1695, 1366, 1251, 1152, 1100, 1044 cm$^{-1}$; HRMS (ES$^+$) calcd C$_{35}$H$_{55}$NO$_7$Si 652.3646. found 652.3653 (MNa$^+$). Isomers A and B: the stereochemistry of each oxo bridge was assigned following the general procedure outlined above.

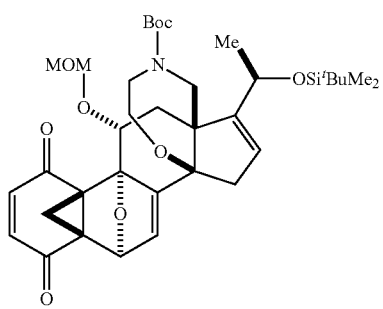

A

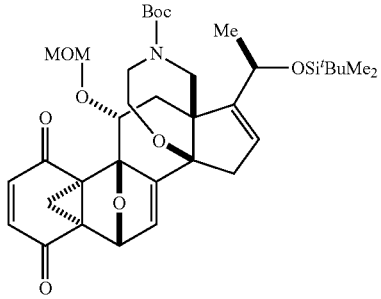

B

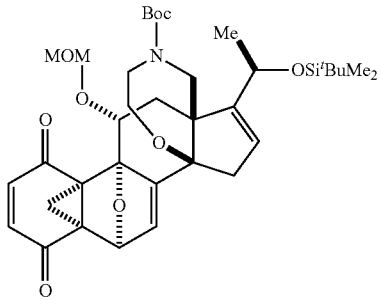

C

Entry 6, Scheme 6:

Reaction performed with furan 26 (17.5 mg, 32 mmol), 1-bromo-6-(trimethylsilyl)-bicyclo[4.1.0]hept-3-ene-2,5-dione (Collis et al., Austr. J. Chem. 1997, 50, 505-513) (19.5 mg, 71 mmol, 2.2 equiv), CsF (19 mg, 0.13 mmol, 4.0 equiv), and 0.5 mL of MeCN. The reaction mixture was stirred for 2.5 h. Purification by chromatography on silica gel (30→50% EtOAc/hexanes) furnished cycloadducts A, B, and C as a 3:3:2 mixture of products as a yellow oil (21 mg, 99%). TLC R$_f$=0.18 (30% EtOAc/hexanes), HRMS (ES$^+$) calcd C$_{36}$H$_{51}$NO$_9$Si 692.3231. found 692.3238 (MNa$^+$). Isomers A, B, and C: the stereochemistry of each oxo bridge was assigned following the general procedure outlined above. In the endo product, H7 appears at 6.5 ppm and H6 at 5.0 ppm (Δ=1.5 ppm), whereas in the exo products, H7 appears between 6.1-6.3 ppm and H7 at 5.5 (Δ≤0.8 ppm). These chemical shift differences are consistent with the stereochemical assignment, as based on available literature precedent (Collis et al., Austr. J. Chem. 1997, 50, 505-513).

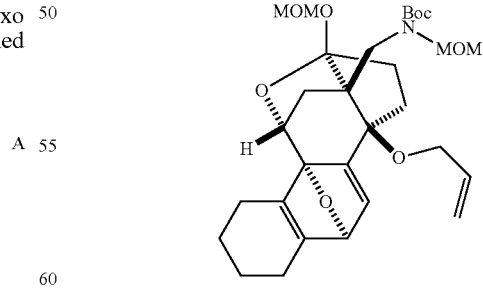

29

Reaction performed with furan 21 (15 mg, 32 mmol), cyclohexyne precursor S6 (27 mg, 89 mmol, 2.8 equiv), CsF (30 mg, 0.20 mmol, 6.1 equiv) and 0.5 mL of MeCN. The reaction mixture was stirred for 23 h. Purification by chromatography on silica gel (40→60% EtOAc/hexanes) furnished 29 as a clear oil. TLC R$_f$=0.30 (60% EtOAc/hexanes); $^1$H NMR (CDCl$_3$, 600 MHz) δ 6.99-6.96 (m, 1H), 5.86-5.77 (m, 1H), 5.24-5.15 (m, 1H), 5.12 (s, 1H), 5.09 (d, 1H, J=10.3 Hz), 5.04-5.00 (m, 1H), 4.92 (d, 1H, J=10.2 Hz), 4.86 (d, 1H, J=10.2 Hz), 4.66-4.62 (m, 2H), 4.32-3.48 (m, 4H), 3.38 (s, 3H), 3.27 (s, 3H), 2.40-2.33 (m, 2H), 2.28-2.09 (m, 7H), 2.04-1.96 (m, 3H), 1.77-1.77 (m, 1H), 1.69 (s, 1H), 1.48 (s, 9H) ppm; IR (thin film) ν 2932, 1699, 1293, 1146, 1080, 1033, 904 cm$^{-1}$; HRMS (ES$^+$) calcd C$_{30}$H$_{43}$NO$_8$ 568.2887. found 568.2887 (MNa$^+$). The stereochemistry of the oxo bridge was assigned following the general procedure outlined above.

Reaction performed with furan 21 (13 mg, 28 mmol), benzyne precursor S5 (25 mg, 57 mmol, 2.0 equiv), CsF (20 mg, 0.13 mmol, 4.7 equiv) and 0.7 mL of MeCN. The reaction mixture was stirred for 20 h. Purification by chromatography on silica gel (30% EtOAc/hexanes) furnished 30 as a clear oil (17 mg, 90%). TLC R$_f$=0.30 (30% EtOAc/hexanes); $^1$H NMR (CDCl$_3$, 400 MHz) δ 7.11 (d, 1H, J=7.9 Hz), 6.95 (s, 1H), 6.32 (d, 1H, J=7.9 Hz), 5.80 (d, 1H, J=1.9 Hz), 5.67-5.52 (m, 1H), 5.07 (d, 1H, J=6.3 Hz), 5.04-4.84 (m, 5H), 4.68 (d, 1H, J=6.1 Hz), 4.12-3.27 (m, 3H), 3.70 (s, 3H), 3.40 (s, 3H), 3.27 (s, 3H), 2.92-2.87 (m, 1H), 2.58-2.49 (m, 2H), 2.30-2.13 (m, 3H), 2.08-2.03 (m, 1H), 1.51 (s, 9H), 0.87 (s, 9H), 0.34 (s, 3H), 0.28 (s, 3H) ppm; IR (thin film) ν 2928, 2855, 1700, 1453, 1420, 1366, 1292, 1246, 1147, 1034 cm$^{-1}$; HRMS (ES$^+$) calcd C$_{37}$H$_{55}$NO$_9$Si 708.3544. found 708.3546 (MNa$^+$). The stereochemistry of the oxo bridge and the structure of the cycloadduct were assigned based on 1D NOE correlations.

X-ray Structure Determination

Compound 27 (with R=H) crystallizes as colorless-block-like crystals from a dichloromethane/pentane solution. There are two molecules of the compound in the unit cell of the primitive, centrosymmetric triclinic space group P-1. As such, the compound is a racemic mixture.

The structure of the tricyclic compound is shown in FIG. 1. Of note is the intra-molecular hydrogen bond from the hydroxyl, O3, to the adjacent ether oxygen O4 (O3 . . . O4=2.8319(14) Å). The hydroxyl hydrogen was initially located from a difference Fourier map and subsequently refined in an idealized position riding on the hydroxyl oxygen, with allowed rotation to minimize the electron density contribution. All other hydrogens were included in idealized locations and allowed to refine with the atom to which they are bonded. The bond distances and angles within the molecule are as expected.

Crystal data for C$_{19}$H$_{27}$NO$_5$; M$_r$=349.42; Triclinic; space group P-1; a=9.5184(4) Å; b=9.5693(4) Å; c=10.8747(4) Å; α=66.8710(10)°; β=77.529(2)°; γ=76.674(2)°; V=877.63(6) Å$^3$; Z=2; T=100(2) K; λ(Cu—Kα)=1.54178 Å; μ(Cu—Kα)=0.779 mm$^{-1}$; d$_{calc}$=1.322 g·cm$^{-3}$; 8631 reflections collected; 3089 unique (R$_{int}$=0.0183); giving R$_1$=0.0404, wR$_2$=0.1031 for 2987 data with [I>2σ(I)] and R$_1$=0.0414, wR$_2$=0.1041 for all 3089 data. Residual electron density (e$^-$·Å$^{-3}$) max/min: 0.310/−0.376.

An arbitrary sphere of data were collected on a colorless block-like crystal, having approximate dimensions of 0.45× 0.43×0.25 mm, on a Bruker APEX diffractometer using a combination of ω- and φ-scans of 0.5°. Data were corrected for absorption and polarization effects and analyzed for space group determination. The structure was solved by direct methods and expanded routinely. The model was refined by full-matrix least-squares analysis of F$^2$ against all reflections. All non-hydrogen atoms were refined with anisotropic thermal displacement parameters. Unless otherwise noted, hydrogen atoms were included in calculated positions. Thermal parameters for the hydrogens were tied to the isotropic thermal parameter of the atom to which they are bonded (1.5× for methyl, 1.2× for all others).

Example 2

Synthesis of Alternative Batrachotoxin Analogues

The structures depicted in Scheme 8 can be prepared by adaptation of the synthetic route described in Example 1. These compounds represent alternative analogues of the natural product batrachotoxin.

Scheme 8. Generic structures acting as sodium current inhibitors with voltage-gated sodium channels.

R$_1$ = methoxymethyl, (other) acetal, acyl
R$_2$ = methyl, t-Butoxycarbonyl, alkyl, acyl
R = alkyl, aryl, heteroaryl
R$_4$, R$_5$, R$_6$ = H, methoxy, carbocycle, heterocycle The synthetic route used to prepare precursors to the furan-based compounds of generic structure 51 is described in Example 1. An overview of synthetic route used to prepare 6-membered fused aromatic analogues of structure 52 is shown in Scheme 9 (e.g., with R$_5$=methoxy; R$_4$, R$_6$=H).

Scheme 9. Example of synthetic route to an aromatic methoxy analog of 52.

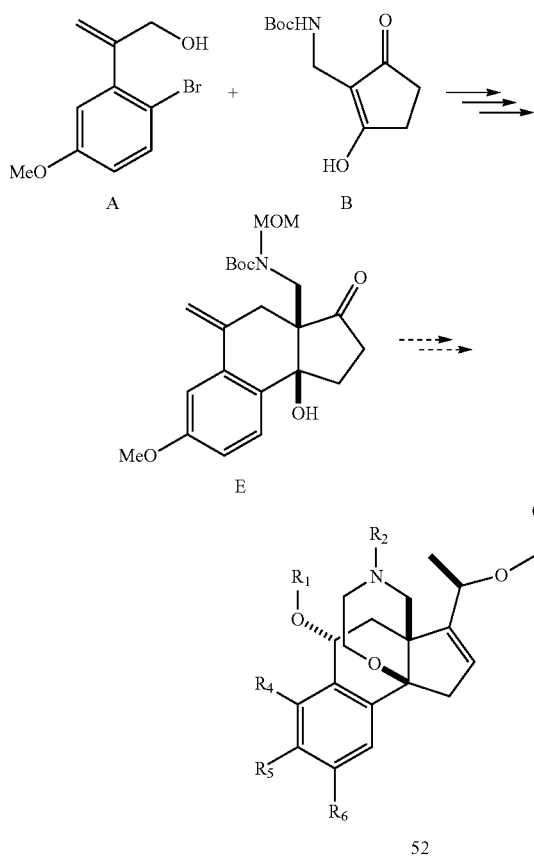

Synthesis of Compounds Based on Furan-Fused Structure 51.

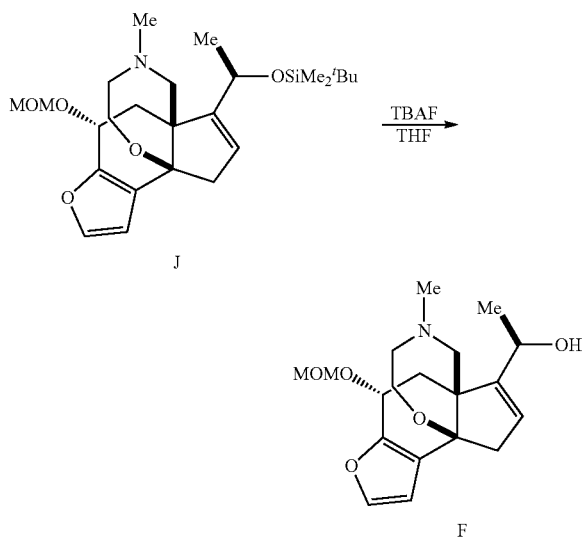

To a stirred solution of J (45 mg, 0.097 mmol) in THF (1 ml) was added TBAF (1M in THF, 200 μL, 2.0 mmol) at rt. The solution was stirred until the reaction reached completion as indicated by TLC (50% EtOAc/hexanes). The reaction was quenched with saturated aqueous ammonium chloride. The mixture was partitioned between EtOAc and water. The aqueous phase was extracted three times with EtOAc. The combined organic phases were dried over MgSO$_4$, filtered and concentrated under reduced pressure. The residue was purified by flash column chromatography (2% to 5% MeOH/CH$_2$Cl$_2$) to afford F (32.5 mg, 0.093 mmol, 96%) as a colorless crystalline solid.

$^1$H NMR (500 MHz; CDCl$_3$): δ 7.38 (d, J=1.9 Hz, 1H), 6.39 (d, J=1.9 Hz, 1H), 5.70 (s, 1H), 4.90 (m, 2H), 4.63 (d, J=6.9 Hz, 1H), 4.23-4.22 (m, 1H), 3.52-3.48 (m, 1H), 3.38-3.34 (m, 4H), 3.07 (dd, J=15.4, 4.3 Hz, 1H), 2.89 (dd, J=17.4, 2.0 Hz, 1H), 2.71-2.62 (m, 3H), 2.50 (t, J=10.7 Hz, 1H), 2.33 (s, 3H), 2.27 (d, J=12.7 Hz, 1H), 2.14-2.11 (m, 1H), 1.34 (d, J=6.5 Hz, 3H).

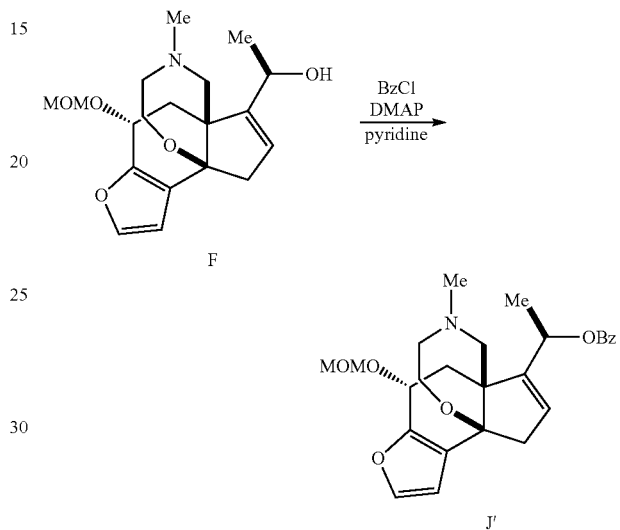

To a stirred solution of F (4.2 mg, 0.012 mmol) in pyridine (1 ml) was added benzoyl chloride (2.0 mg, 0.014 mmol) and 4-(dimethylamino)pyridine (1.5 mg) at rt. After stirring for 12 h at rt, the reaction mixture was partitioned between dichloromethane and 10% copper sulfate aqueous solution. The organic phase was separated, dried over Na$_2$SO$_4$, filtered and concentrated under reduced pressure. The residue was purified by flash column chromatography (2% to 5% MeOH/CH$_2$Cl$_2$) to afford J' (2.5 mg, 0.0055 mmol, 46%) as a colorless oil.

$^1$H NMR (500 MHz; CDCl$_3$): δ 8.03 (dd, J=8.3, 1.2 Hz, 2H), 7.55-7.51 (m, 1H), 7.42-7.39 (m, 2H), 7.35 (d, J=1.9 Hz, 1H), 6.38 (d, J=1.9 Hz, 1H), 5.91 (t, J=2.1 Hz, 1H), 5.83 (q, J=6.3 Hz, 1H), 4.75 (t, J=5.3 Hz, 1H), 4.58 (d, J=6.8 Hz, 1H), 4.36 (d, J=6.7 Hz, 1H), 3.53 (dt, J=12.9, 3.4 Hz, 1H), 3.44-3.38 (m, 1H), 3.12 (s, 3H), 2.91 (dd, J=17.5, 1.3 Hz, 1H), 2.79-2.73 (m, 3H), 2.62-2.45 (m, 3H), 2.36 (s, 3H), 1.97 (dd, J=14.2, 5.5 Hz, 1H), 1.52 (d, J=6.4 Hz, 3H).

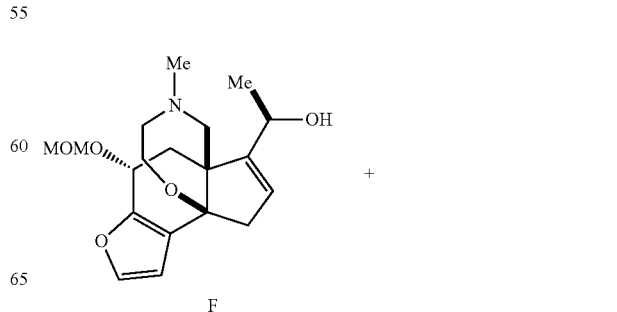

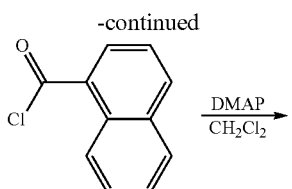

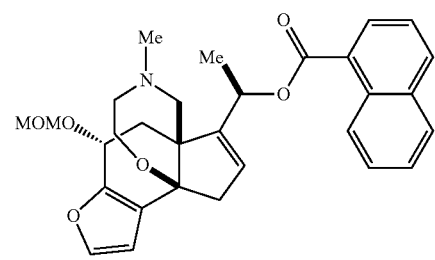

K

To a stirred solution of F (3 mg, 0.0086 mmol) in dichloromethane (1 ml) were added 1-naphthoyl chloride (3.2 mg, 0.17 mmol) and 4-(dimethylamino)pyridine (2 mg, 0.017 mmol) at rt. After stirring for 2.5 h at rt, the reaction mixture was partitioned between dichloromethane and saturated aqueous sodium bicarbonate. The organic phase was dried over MgSO$_4$, filtered and concentrated under reduced pressure. The residue was purified by flash column chromatography (20% to 50% EtOAc/hexanes) to afford K (3.3 mg, 0.0066 mmol 77%).

$^1$H NMR (500 MHz; CDCl$_3$): δ 8.96 (d, J=8.6 Hz, 1H), 8.17 (dd, J=7.2, 0.9 Hz, 1H), 7.99 (d, J=8.1 Hz, 1H), 7.87 (d, J=7.9 Hz, 1H), 7.59-7.55 (m, 1H), 7.53-7.50 (m, 1H), 7.46 (t, J=7.7 Hz, 1H), 7.35 (d, J=1.8 Hz, 1H), 6.39 (d, J=1.8 Hz, 1H), 5.94-5.90 (m, 2H), 4.77 (t, J=5.0 Hz, 1H), 4.56 (d, J=6.8 Hz, 1H), 4.36 (d, J=6.8 Hz, 1H), 3.57-3.52 (m, 1H), 3.46-3.41 (m, 1H), 3.06 (s, 3H), 2.95-2.91 (m, 1H), 2.85-2.75 (m, 3H), 2.63-2.49 (m, 3H), 2.39 (s, 3H), 2.05-1.98 (m, 1H), 1.61 (d, J=6.4 Hz, 3H).

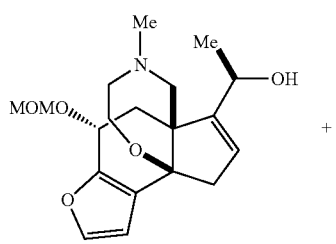

F

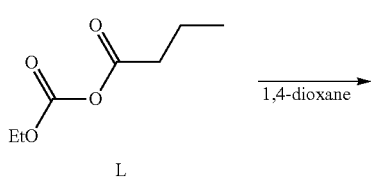

L

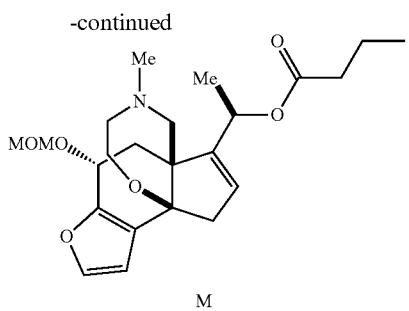

M

To a stirred solution of F (3.5 mg, 0.0100 mmol) in 1,4-dioxane (0.5 ml) was added anhydride L (16 mg, 0.043 mmol) at rt. After stirring for 3 h at 90° C., the reaction mixture was concentrated in vacuo. The residue was purified by preparative thin layer chromatography (50% EtOAc/hexanes) to afford M (0.442 μmol, 5%).

$^1$H NMR (600 MHz; CDCl$_3$): δ 7.36 (d, J=1.8 Hz, 1H), 6.36 (d, J=1.8 Hz, 1H), 5.78 (s, 1H), 5.59 (q, J=6.0 Hz, 1H), 4.81 (t, J=5.4 Hz, 1H), 4.77 (d, J=6.8 Hz, 1H), 4.65 (d, J=6.9 Hz, 1H), 3.53-3.50 (m, 1H), 3.45-3.36 (m, 4H), 2.85 (d, J=16.5 Hz, 1H), 2.79-2.64 (m, 3H), 2.57 (t, J=9.3 Hz, 1H), 2.52 (d, J=13.2 Hz, 1H), 2.46-2.42 (m, 1H), 2.33 (s, 3H), 2.27-2.22 (m, 2H), 1.88 (dd, J=13.9, 5.4 Hz, 1H), 1.65 (dq, J=14.8, 7.4 Hz, 2H), 1.40 (d, J=6.4 Hz, 3H), 0.94 (t, J=7.4 Hz, 3H).

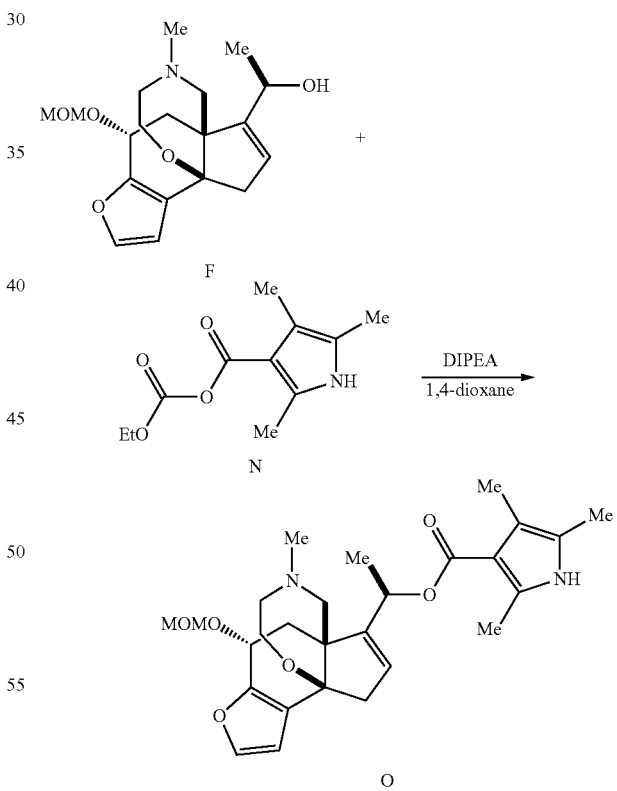

O

To a stirred solution of F (5 mg, 0.014 mmol) in 1,4-dioxane (0.5 ml) were added anhydride N (16 mg, 0.07 mmol) and N,N-diisopropylethylamine (1 drop) at rt. After stirring for 3 h at 90° C., the reaction mixture was concentrated in vacuo. The residue was purified by preparative thin layer chromatography (60% EtOAc/hexanes) to afford O (0.0018 mmol, 13%).

¹H NMR (600 MHz; CDCl₃): δ 7.59 (s, 1H), 7.35 (d, J=1.7 Hz, 1H), 6.37 (d, J=1.7 Hz, 1H), 5.84 (s, 1H), 5.73 (q, J=6.3 Hz, 1H), 4.77 (t, J=5.3 Hz, 1H), 4.62 (d, J=6.8 Hz, 1H), 4.46 (d, J=6.7 Hz, 1H), 3.56-3.53 (m, 1H), 3.42 (ddd, J=12.7, 9.6, 2.6 Hz, 1H), 3.20 (s, 3H), 2.88 (dd, J=17.3, 1.6 Hz, 1H), 2.78-2.71 (m, 3H), 2.60-2.45 (m, 3H), 2.41 (s, 3H), 2.36 (s, 3H), 2.10 (s, 3H), 2.08 (s, 3H), 1.95-1.92 (m, 1H), 1.47 (d, J=6.4 Hz, 3H).

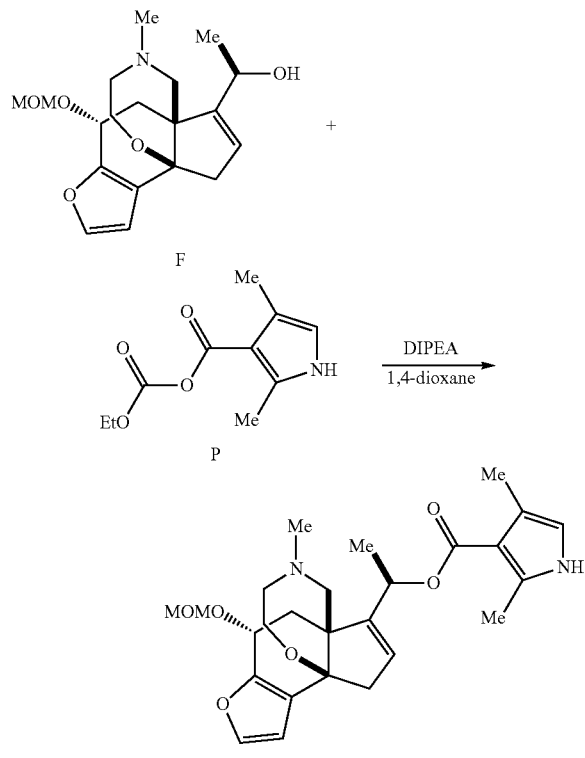

To a stirred solution of F (4 mg, 0.0115 mmol) in 1,4-dioxane (0.5 ml) were added anhydride P (16 mg, 0.07 mmol) and N,N-diisopropylethylamine (1 drop, excess) at rt. After stirring for 3 h at 90° C., the reaction mixture was concentrated in vacuo. The residue was purified by preparative thin layer chromatography (60% EtOAc/hexanes) to afford Q (0.0023 mmol, 20%).

¹H NMR (600 MHz; CDCl₃): δ 7.79 (s, 1H), 7.35 (d, J=1.8 Hz, 1H), 6.37 (d, J=1.8 Hz, 1H), 6.30 (s, 1H), 5.84 (s, 1H), 5.73 (q, J=6.3 Hz, 1H), 4.76 (t, J=5.3 Hz, 1H), 4.61 (d, J=6.7 Hz, 1H), 4.44 (d, J=6.8 Hz, 1H), 3.55-3.52 (m, 1H), 3.41 (ddd, J=13.1, 9.1, 2.3 Hz, 1H), 3.18 (s, 3H), 2.88 (dd, J=17.4, 2.0 Hz, 1H), 2.78-2.70 (m, 3H), 2.57 (td, J=10.9, 2.4 Hz, 1H), 2.52 (d, J=13.2 Hz, 1H), 2.48-2.40 (m, 4H), 2.36 (s, 3H), 2.18 (d, J=0.9 Hz, 3H), 1.96-1.92 (m, 1H), 1.47 (d, J=6.4 Hz, 3H).

Synthesis of Compounds Based on Aryl-Fused Structure 52.

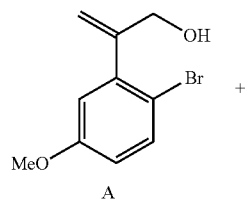

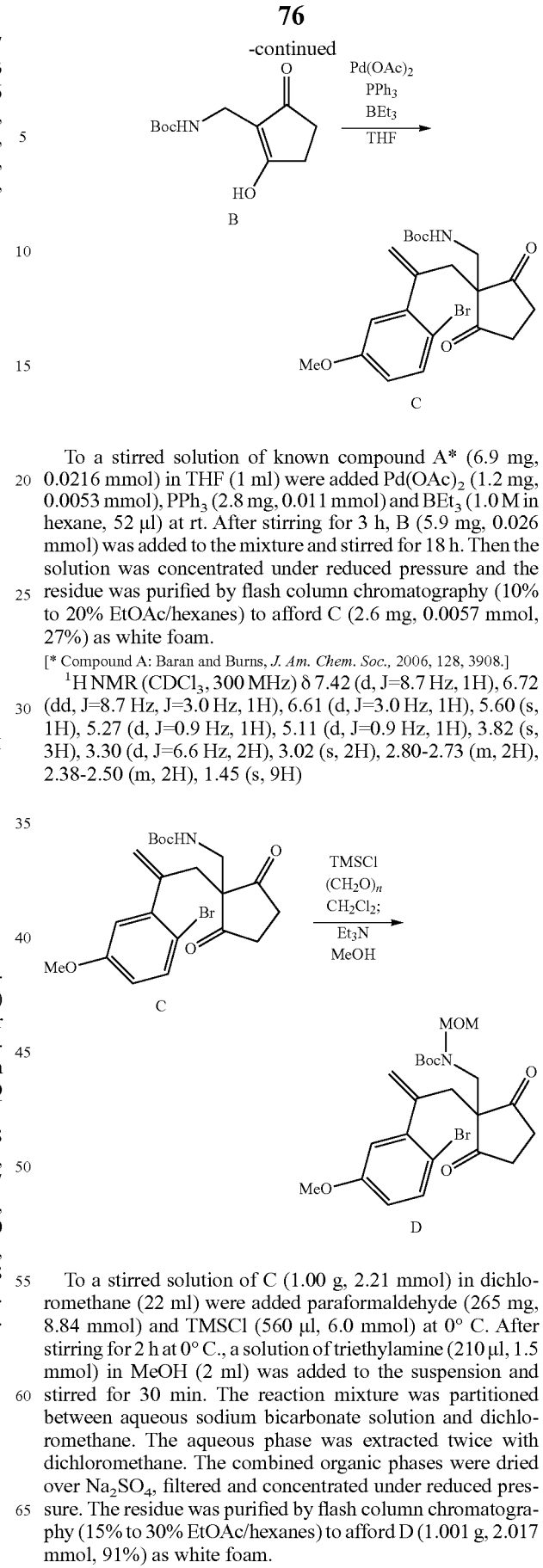

To a stirred solution of known compound A* (6.9 mg, 0.0216 mmol) in THF (1 ml) were added Pd(OAc)₂ (1.2 mg, 0.0053 mmol), PPh₃ (2.8 mg, 0.011 mmol) and BEt₃ (1.0 M in hexane, 52 μl) at rt. After stirring for 3 h, B (5.9 mg, 0.026 mmol) was added to the mixture and stirred for 18 h. Then the solution was concentrated under reduced pressure and the residue was purified by flash column chromatography (10% to 20% EtOAc/hexanes) to afford C (2.6 mg, 0.0057 mmol, 27%) as white foam.

[* Compound A: Baran and Burns, *J. Am. Chem. Soc.*, 2006, 128, 3908.]

¹H NMR (CDCl₃, 300 MHz) δ 7.42 (d, J=8.7 Hz, 1H), 6.72 (dd, J=8.7 Hz, J=3.0 Hz, 1H), 6.61 (d, J=3.0 Hz, 1H), 5.60 (s, 1H), 5.27 (d, J=0.9 Hz, 1H), 5.11 (d, J=0.9 Hz, 1H), 3.82 (s, 3H), 3.30 (d, J=6.6 Hz, 2H), 3.02 (s, 2H), 2.80-2.73 (m, 2H), 2.38-2.50 (m, 2H), 1.45 (s, 9H)

To a stirred solution of C (1.00 g, 2.21 mmol) in dichloromethane (22 ml) were added paraformaldehyde (265 mg, 8.84 mmol) and TMSCl (560 μl, 6.0 mmol) at 0° C. After stirring for 2 h at 0° C., a solution of triethylamine (210 μl, 1.5 mmol) in MeOH (2 ml) was added to the suspension and stirred for 30 min. The reaction mixture was partitioned between aqueous sodium bicarbonate solution and dichloromethane. The aqueous phase was extracted twice with dichloromethane. The combined organic phases were dried over Na₂SO₄, filtered and concentrated under reduced pressure. The residue was purified by flash column chromatography (15% to 30% EtOAc/hexanes) to afford D (1.001 g, 2.017 mmol, 91%) as white foam.

¹H NMR (CDCl₃, 300 MHz) δ 7.39 (d, J=6.3 Hz, 1H), 6.71-6.62 (m, 2H), 5.25 (s, 1H), 5.13 (s, 1H), 4.49 (br s, 2H), 3.79 (s, 3H), 3.69-3.48 (m, 2H), 3.16 (s, 3H), 2.99-2.88 (m, 2H), 2.71-2.54 (m, 2H), 2.52-2.39 (m, 2H), 1.43 (br s, 9H)

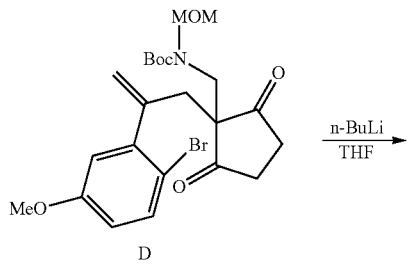

D

To a stirred solution of D (1.40 g, 2.82 mmol) in THF (28 ml) was added n-BuLi (1.0 M in hexane, 3.0 ml, 3.0 mmol) over 10 min at −78° C. After stirring for 1 h, the reaction was quenched with saturated aqueous ammonium chloride. The mixture was partitioned between EtOAc and water. The aqueous phase was extracted twice with EtOAc. The combined organic phases were washed with brine, dried over Na₂SO₄, filtered and concentrated under reduced pressure. The residue was purified by flash column chromatography (15% to 30% EtOAc/hexanes) to afford E (571 mg, 1.37 mmol, 49%) as white foam.

¹H NMR (CDCl₃, 300 MHz) δ 7.01 (d, J=8.7 Hz, 1H), 7.09 (d, J=1.2 Hz, 1H), 6.88 (dd, J=1.2 Hz, 8.7 Hz, 1H), 5.99 (s, 1H), 5.58 (d, J=2.4 Hz, 1H), 4.96 (d, J=2.4 Hz, 1H), 4.65 (d, J=10.7 Hz, 1H), 4.34 (d, J=10.7 Hz, 1H), 3.88-3.78 (m, 4H), 3.51 (d, J=16.2 Hz, 1H), 3.22 (s, 3H), 2.79-2.60 (m, 2H), 2.56-2.28 (m, 3H), 2.13 (d, J=11.4 Hz, 1H), 1.10 (s, 9H)

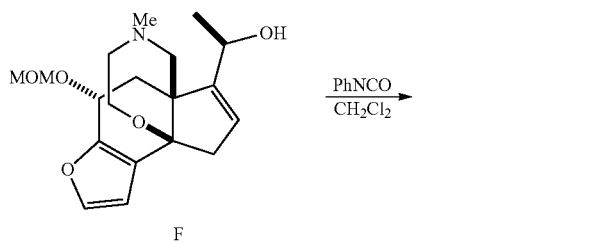

To a stirred solution of F (2.2 mg, 0.0066 mmol) in dichloromethane (1 ml) was added phenyl isocyanate (2 μl, 0.02 mmol) at rt. After stirring for 2.5 h, the solution was concentrated to a half of the initial volume. The residue was purified by flash column chromatography (15% to 40% EtOAc/hexanes) to afford G (2.4 mg, 0.0047 mmol, 71%) as white foam.

¹H NMR (CDCl₃, 400 MHz) δ 7.42-7.25 (m, 5H), 7.04 (t, J=7.2 Hz, 1H), 6.62 (s, 1H), 6.39 (s, 1H), 5.80 (s, 1H), 5.48 (q, J=7.2 Hz, 1H), 4.81 (t, J=4.8 Hz, 1H), 4.72 (d, J=7.2 Hz, 1H), 4.61 (d, J=7.2 Hz, 1H), 3.55-3.38 (m, 2H), 3.28 (s, 3H), 2.97-2.81 (m, 2H), 2.79-2.64 (m, 2H), 2.58-2.48 (m, 2H), 2.41 (d, J=12.4 Hz, 1H), 2.37 (s, 3H), 2.00 (dd, J=12.4 Hz, J=4.8 Hz, 1H), 1.47 (d, J=6.4 Hz, 3H)

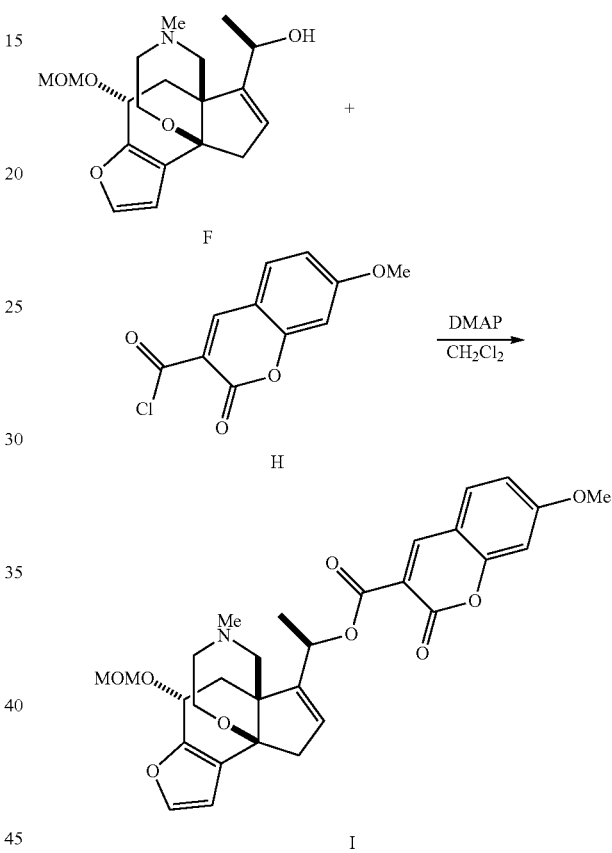

To a stirred solution of F (1.1 mg, 0.0033 mmol) in dichloromethane (1 ml) were added H (5.8 mg, 0.024 mmol) and 4-(dimethylamino)pyridine (2.6 mg, 0.021 mmol) at rt. After stirring for 47 h at 40° C., the reaction mixture was partitioned between dichloromethane and saturated aqueous sodium bicarbonate. The organic phase was dried over MgSO₄, filtered and concentrated under reduced pressure. The residue was purified by preparative thin layer chromatography (60% EtOAc/hexanes) to afford I (0.7 mg, 0.001 mmol, 38%) as white foam.

¹H NMR (CDCl₃, 400 MHz) δ 8.41 (s, 1H), (d, J=8.4 Hz, 1H), 7.17 (s, 1H), 7.04 (t, J=8.4 Hz, 1H), 6.88 (dd, J=7.2 Hz, J=1.2 Hz, 1H), 6.80 (d, J=1.2 Hz, 1H), 6.39 (s, 1H), 5.86 (q, J=6.8 Hz, 1H), 4.81 (t, J=4.0 Hz, 1H), 4.68 (d, J=7.2 Hz, 1H), 4.58 (d, J=7.2 Hz, 1H), 3.90 (s, 3H), 3.58-3.38 (m, 2H), 3.28 (s, 3H), 2.97-2.70 (m, 4H), 2.62-2.45 (m, 3H), 2.38 (s, 3H), 1.96 (dd, J=12.0 Hz, J=4.0 Hz, 1H), 1.47 (d, J=6.4 Hz, 3H).

Some analogues of structure 51 (e.g., R₁=OCH₂OMe, R₂=Me, R=aryl, alkyl) have been assayed in vitro using patch-clamp electrophysiology. These compounds were found to significantly reduce sodium currents generated by the alpha subunit of rat Nav1.4 channels heterologously expressed in Chinese hamster ovarian (CHO) cells.

Example 3

Visualizing Dermal Permeation of Sodium Channel Modulators by Mass Spectrometric Imaging This example provides a simple approach for measuring penetration of a drug through skin and developing a map of drug distribution as it passes through the skin layers. Many clinically employed analgesics and anesthetics for relieving pain modulate voltage-gated sodium channels ($Na_vs$), a family of integral membrane proteins responsible for the rising phase of action potentials in electrically conducting cells. Nayak and Das, *Biotechnology Letters*, 2013, 35, 1351. One such example is lidocaine, a prescription-based injectable and topical pharmaceutical. In addition to clinically employed anesthetics, natural neurotoxic alkaloids, such as saxitoxin, neosaxitoxin (Rodriguez-Navarro et al., *Anesthesiology*, 2007, 106, 339), batrachotoxin (Bosmans et al., *Febs Letters*, 2004, 577, 245), and aconitine (Ameri, *Progress in Neurobiology*, 1998, 56, 211), are sodium channel modulators currently being investigated as potential pain therapeutics and local anesthetics (Rodriguez-Navarro et al., *Anesthesiology*, 2007, 106, 339; Andavan and Lemmens-Gruber, *Current Medicinal Chemistry*, 2011, 18, 377; Butterworth, *Regional Anesthesia and Pain Medicine*, 2011, 36, 101). The high specificity and high affinity that neurotoxins have for sodium channels in comparison to common anesthetics form the basis for their prospective use as potent analgesics. Butterworth, *Regional Anesthesia and Pain Medicine*, 2011, 36, 101. High affinity leads to lower dosing requirements and the potential for lower toxicity due to greater selectivity. For example, a study has shown that neosaxitoxin is roughly 1 million-fold more potent than lidocaine. Bokesch et al., *Journal of Pharmacology and Experimental Therapeutics*, 1986, 237, 773.

As described herein for batrachotoxin, synthetic routes for the development of neurotoxins have been explored with the goal of producing these molecules in the laboratory in larger amounts than what can be reasonably isolated from natural resources, and also of producing analogs with unique physicochemical and pharmacological properties. Andresen and Du Bois, *Journal of the American Chemical Society*, 2009, 131, 12524; Devlin and Du Bois, *Chemical Science*, 2013, 4, 1059; Mulcahy and Du Bois, *Journal of the American Chemical Society*, 2008, 130, 12630; Shinohara et al., *Chemistry—a European Journal*, 2011, 17, 12144. However, little to nothing is known about the ability of these compounds to penetrate human skin necessary to produce a topical analgesic effect. Different methods have been used to analyze the transdermal absorption of compounds through the skin, including skin extraction measurements (Touitou et al., *Journal of Controlled Release*, 1998, 56, 7), quantitative autoradiography (Fabin and Touitou, *International Journal of Pharmaceutics*, 1991, 74, 59), and spectroscopic methods such as fluorescence (Lieb et al., *Journal of Investigative Dermatology*, 1992, 99, 108), and FTIR (Sennhenn et al., *Skin Pharmacology*, 1993, 6, 152). Mass spectrometry imaging offers the advantage of being a label-free method by which the distribution of a multitude of compounds can be mapped in biological tissues with high specificity. Bunch et al., *Rapid Communications in Mass Spectrometry*, 2004, 18, 3051; Judd et al., *Pharmaceutical Research*, 2013, 30, 1896; Wiseman et al., *Proceedings of the National Academy of Sciences of the United States of America*, 2008, 105, 18120.

In this example, histologically compatible high mass resolution/mass accuracy desorption electrospray ionization mass spectrometric imaging (DESI-MSI) was used to investigate the permeation of natural sodium channel blockers and novel synthetic analogs when topically applied to human and animal skin ex vivo and in vivo, respectively. DESI-MSI allows two-dimensional mapping of a sample in the ambient environment, without the need for extensive sample preparation. Samples are bombarded with microdroplets of acetonitrile that dissolve hundreds of endogenous lipids and metabolites, as well as exogenous compounds present in tissue. The splash forms secondary microdroplets that enter a mass spectrometer, providing a detailed chemical map of the distribution of molecules within the sample surface. Costa and Cooks, *Chemical Physics Letters*, 2008, 464, 1. After DESI-MSI, the same tissue section was stained, optically imaged, and compared to selected 2D DESI-MS ion images. The compounds investigated included the common analgesics lidocaine and prilocaine, as well as aconitine, an herbal neurotoxin used in Chinese medicine, saxitoxin, a sodium channel inhibitor synonymous with paralytic shellfish poisoning, a novel synthetic analog of saxitoxin, and a novel synthetic analog of batrachotoxin. The effect of sunburn injury and different times of exposure on the penetration of the applied compounds were also investigated. Using DESI-MSI, it was demonstrated that the compounds of interest are detected with high specificity within the hundreds of other endogenous skin compounds concurrently being analyzed. Their spatial distribution has been mapped and directly compared to skin sections to assess transdermal penetration.

Figure 6:
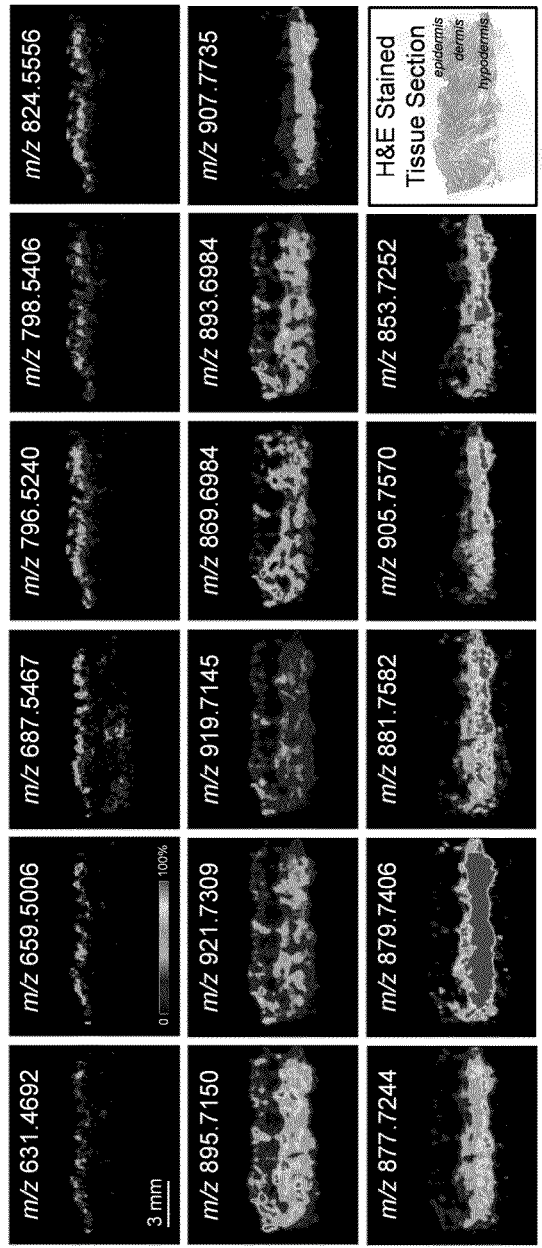
FIG. 6. Selected positive ion mode DESI-MS ion images of human skin sample and optical image of the same tissue section images by DESI after H&E stain are shown.
Figure 7:
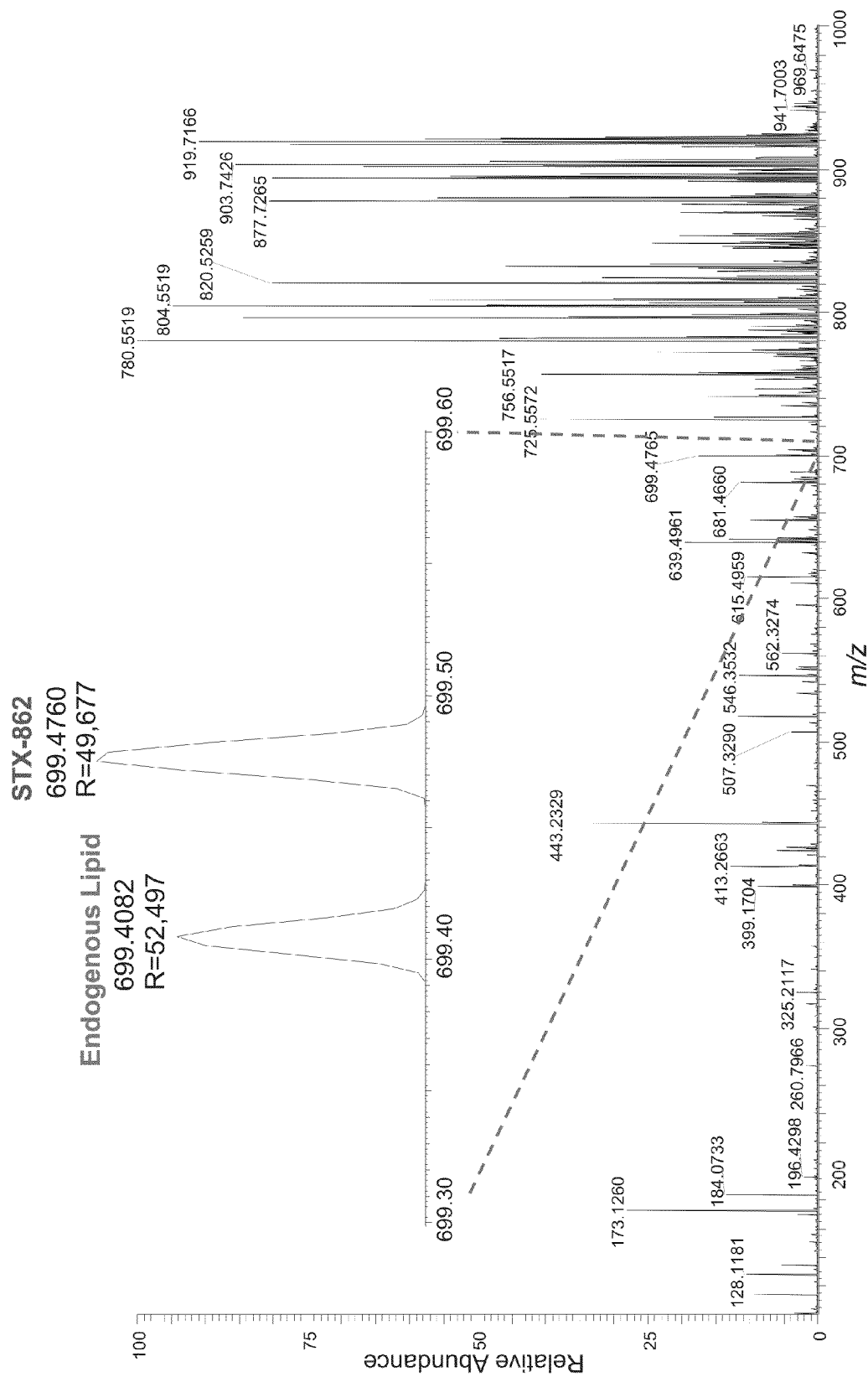
FIG. 7. Positive ion mode DESI-MS mass spectrum of human skin from m/z 100-1000. Inset shows the range m/z 699.30-699.60 in which peaks of the compound STX-862 and an endogenous lipid (detected at the same nominal m/z) are resolved using high mass resolution DESI-MSI. (R=Orbitrap resolving power at the m/z shown).

Human skin samples were obtained from four patients undergoing surgery at Stanford Medical School. All patients gave written informed consent following approved IRB protocol. The skin was placed in a shallow dish partially filled with synthetic interstitial fluid. Confined circular treatment areas were created by delineating the application site with ink and surrounding with petroleum jelly. After 1, 4, or 10 hours of application, the skin was frozen and cross sectional tissue sections carefully prepared to avoid cross-contamination. Positive ion mode DESI-MSI was performed using an Orbitrap for mass analysis at a mass resolution of 60,000 (see below for experimental details). Rich and distinctive molecular profiles were observed from the different layers of skin samples by high resolution DESI-MS imaging. Many of the molecules observed were identified using high mass accuracy and tandem MS experiments as various complex sodium or potassium adducts of complex glycerophospholipids: glycerophosphocholines (PC), lyso-PC, sphingomyelins, glycerophosphoethanolamines, and glycerophosphoglycerols; and glycerolipids: triacylglycerols (TG) and diacylglycerols, within other less abundant species (Table 1). Ion images showing the distribution of these compounds within the different layers of the skin sections are shown in FIG. 6, in comparison with the optical image of the H&E stained tissue sections. Pathological evaluation of the H&E stained human skin tissue sections revealed the presence of epidermis (30-60 µm thickness), superficial dermis (250-450 µm thickness), deep dermis (2,200 to 3,000 µm thickness) and hypodermis (600-1,200 µm thickness) layers within all the human samples analyzed.

Figure 2:
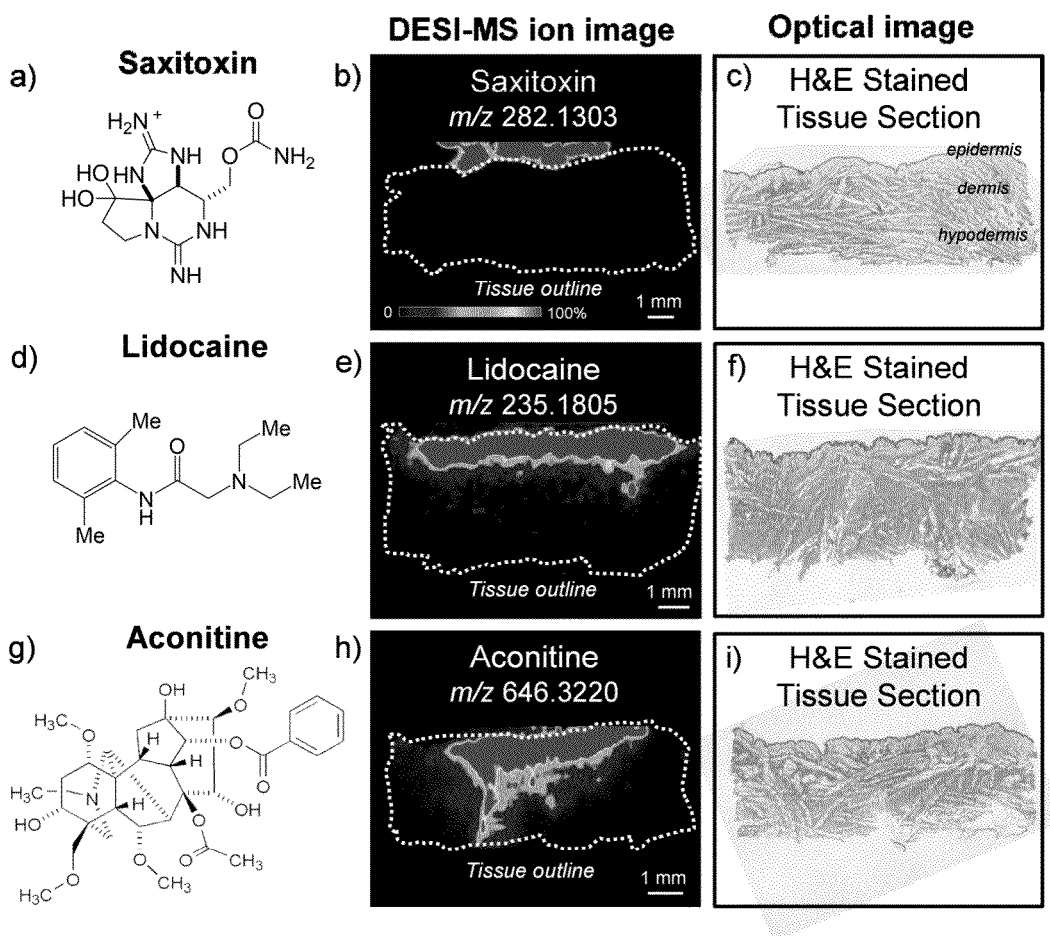
FIG. 2. Penetration of the sodium channel blocker compounds tested in human skin of the same donor using ethanol as the vehicle. Chemical structures are shown for a) saxitoxin, d) lidocaine and g) aconitine. Positive ion mode DESI-MS ion images of the compounds are shown for human skin in which b) saxitoxin, e) lidocaine and h) aconitine were topically applied. Optical images of the same tissue sections imaged by DESI after H&E stain are shown in c) for aconitine, f) for lidocaine and i) for aconitine.

First tested was ethanol, the alcohol most commonly used as a permeation enhancer (Sinha and Kaur, *Drug Development and Industrial Pharmacy*, 2000, 26, 1131), as the vehicle for topical application of saxitoxin, lidocaine, aconitine and two novel synthetic derivatives of STX and BTX to human skin. Despite the high complexity of the DESI mass spectra obtained from the different layers of the human skin, high mass resolution/high mass accuracy measurements allowed for clear mass spectral separation and confirmation of the compounds of interest. Saxitoxin was observed most abundantly at m/z 282.1303 (mass error of 2.14 ppm), corresponding to the protonated molecule with a loss of water, while aconitine was detected in its protonated form at m/z 646.3220 (mass error of 0.35 ppm) as well as lidocaine, at m/z 235.1805 (mass error of 0.09 ppm). FIG. 2 shows the DESI-MSI results obtained for human skin tissue sections of the same donor in which saxitoxin, lidocaine, and aconitine were topically applied using the same experimental conditions, as well as their chemical structures. The optical image of the tissue section H&E stained after DESI-MSI is also shown in FIG. 2 to assist visualization of the outline of the tissue section. As it can be clearly observed in the DESI-MS ion image, saxitoxin did not exhibit any penetration in the human skin tissue section (FIG. 2b). The molecule is completely localized outside of the boundaries of the skin tissue section, on the top of the tissue section where the compound was applied. Despite its low molecular weight which should facilitate skin penetration (Prausnitz and Langer, *Nature Biotechnology,* 2008, 26, 1261), this behavior can be attributed to the high hydrophilicity and polarity of saxitoxin. On the other hand, DESI-MS ion image of lidocaine in FIG. 2e show that the compound is detected throughout the tissue section, penetrating to the deep dermis layer as determined by comparison with the H&E stained tissue section. Similar to lidocaine, aconitine also exhibits a good penetration. The compound was detected deep within the tissue section, reaching the hypodermis layer of the skin, further than what observed with lidocaine. The ion image reveals that a higher relative intensity is observed in the top layers of the skin, which gradually decreases towards the hypodermis layer (FIG. 2h). Although aconitine has a higher molecular weight than lidocaine, both are lipophilic molecules with octanol-water partition coefficients that heavily favor lipids. Prausnitz and Langer, *Nature Biotechnology,* 2008, 26, 1261.

Figure 3:
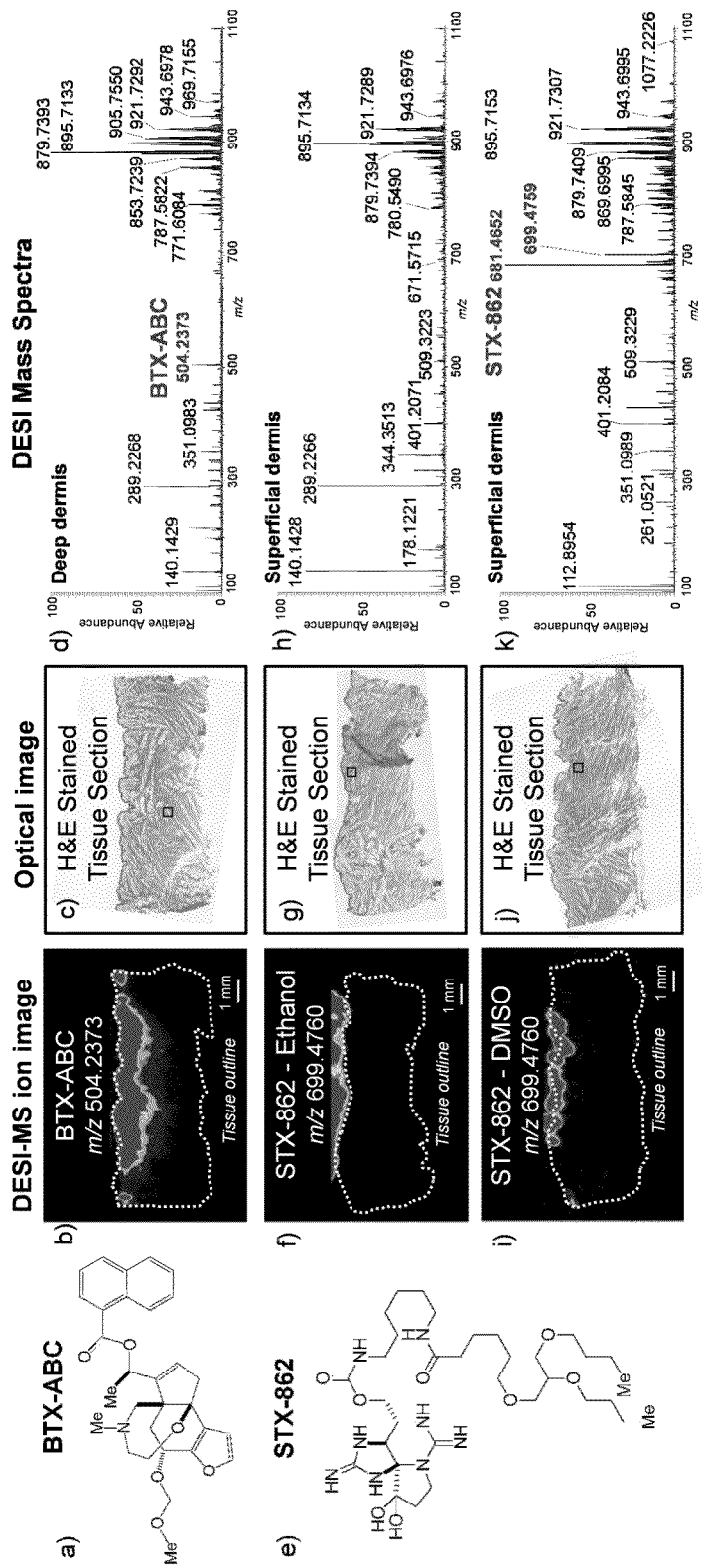
FIG. 3. Penetration of two novel synthetic analogs tested in human skin of the same donor. Chemical structures are shown for a) BTX-ABC and e) STX-862. Positive ion mode DESI-MS ion images of the compounds are shown for human skin in which b) BTX-ABC was topically applied using ethanol as vehicle, STX-862 was topically applied using f) ethanol and i) DMSO as vehicles. Optical images of the same tissue sections imaged by DESI after H&E stain are shown in c), g) and j), respectively. DESI-MS mass spectra of selected skin regions outlined with a small black box in the optical images in c, g, and j are shown for d) BTX-ABC in ethanol, h) STX-862 in ethanol and k) STX-862 in DMSO.

Two synthetic neurotoxin derivatives were synthesized and tested in human skin using ethanol as the vehicle. One of the compounds tested is a derivative of saxitoxin, named STX-862, which was prepared using a strategic modification to a previously reported route for the synthesis of (+)-STX (see below; Mulcahy and Du Bois, *Journal of the American Chemical Society,* 2008, 130, 12630). Compound STX-862 has a lipophilic fatty acid chain appended to the carbamate group of the natural structure. It could be expected that the lipophilic chain would favor the transdermal penetration of the compound in comparison to the native STX counterpart. The other compound is a synthetic derivative of the neurotoxin batrachotoxin, named BTX-ABC, which was prepared following a recent synthetic plan. Devlin and Du Bois, *Chemical Science,* 2013, 4, 1059. Batrachotoxin and its derivatives are lipid-soluble neurotoxins that might be expected to show good permeation through skin. Wang and Wang, *Cellular Signalling,* 2003, 15, 151. Both compounds were detected in the positive ion mode, BTX-ABC in its protonated form at m/z 504.2373 (mass error of 1.44 ppm), and STX-862 with loss of water at m/z 681.4652 (mass error of 0.56 ppm), and in its protonated form m/z 699.4760 (mass error of 0.55 ppm). Note that an endogenous lipid thoroughly distributed in the skin tissue was detected at the same nominal m/z 699.4 of STX-862. This lipid (measured at m/z 699.4082) could be completely resolved from STX-862 using high mass resolution DESI-MSI, thereby enabling accurate mapping of the exogenous compound in tissue (FIG. S2). DESI-MS ion images for STX-862 and BTX-ABC in ethanol are shown in FIG. 3, as well as their chemical structures. As can be observed in FIG. 3f, despite the lipophilic appendage, STX-862 did not penetrate the human skin, similar to what observed for saxitoxin using ethanol as the vehicle (6 samples). The compound was only detected outside of the boundaries of the tissue section, and only lipids were detected in the mass spectra of the epidermis and superficial dermis of the skin (FIG. 3h). Nevertheless, successful penetration was observed for the BTX-ABC, which was completely observed within the skin tissue section reaching the deep dermis layer of the tissue (FIGS. 3b and 3d). The penetration behavior for the compounds described using ethanol as vehicle was consistently observed within the skin sections obtained from the three different donors analyzed. Overall, the average penetration depth of lidocaine was 1.24 mm (5 samples), of aconitine was 3.05 mm (6 samples), BTX-ABC was 2.00 mm (4 samples) and no penetration was observed for saxitoxin (7 samples) or STX-862 (6 samples) using ethanol as the vehicle for topical application.

In an attempt to increase the ability of STX-862 to surpass the skin barrier, dimethyl sulfoxide (DMSO) was used as the vehicle for STX-862. DMSO has been shown to enhance the transdermal permeation of a variety of drugs by interacting with the epidermis lipids and producing alteration in epidermis keratin conformation. Anigbogu et al., *International Journal of Pharmaceutics,* 1995, 125, 265. Interestingly, the DESI-MSI results show that penetration is achieved for STX-862 using DMSO as the vehicle (FIG. 3i). Although not all the compound is observed within the skin section, partial penetration is evident through the epidermis reaching the superficial layer of the skin dermis. FIG. 3k shows the mass spectra of the superficial layer of the skin dermis in which STX-862 can be clearly detected together with the complex phospholipids that characterize that skin layer. An average penetration depth of 0.62 mm was achieved with STX-862 using DMSO as the vehicle (3 samples).

Figure 4:
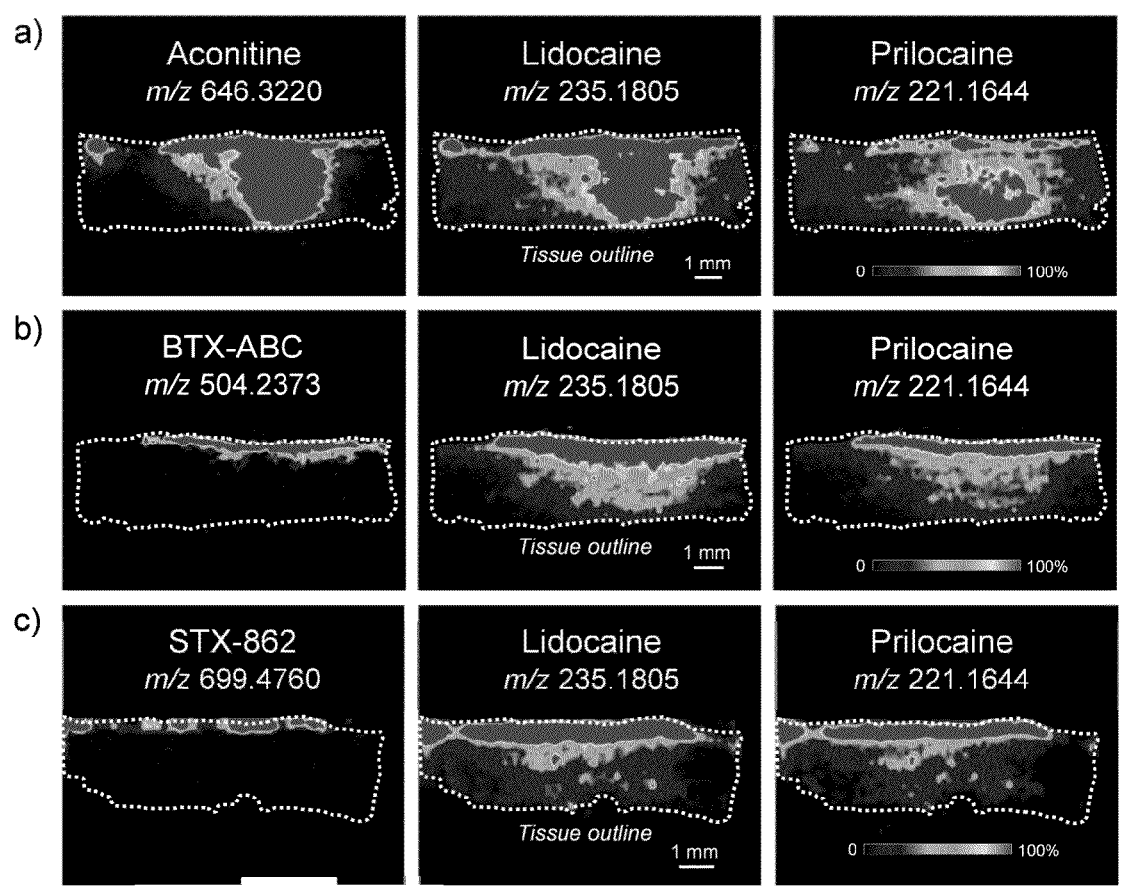
FIG. 4. DESI-MS ion images showing the penetration of a) aconitine, b) BTX-ABC and c) STX-862 tested in human skin of the same donor using EMLA cream. Ion images showing the penetration of lidocaine and prilocaine, compounds with are both present in the EMLA cream formulation, are also presented for the three sections analyzed.
Figure 8:
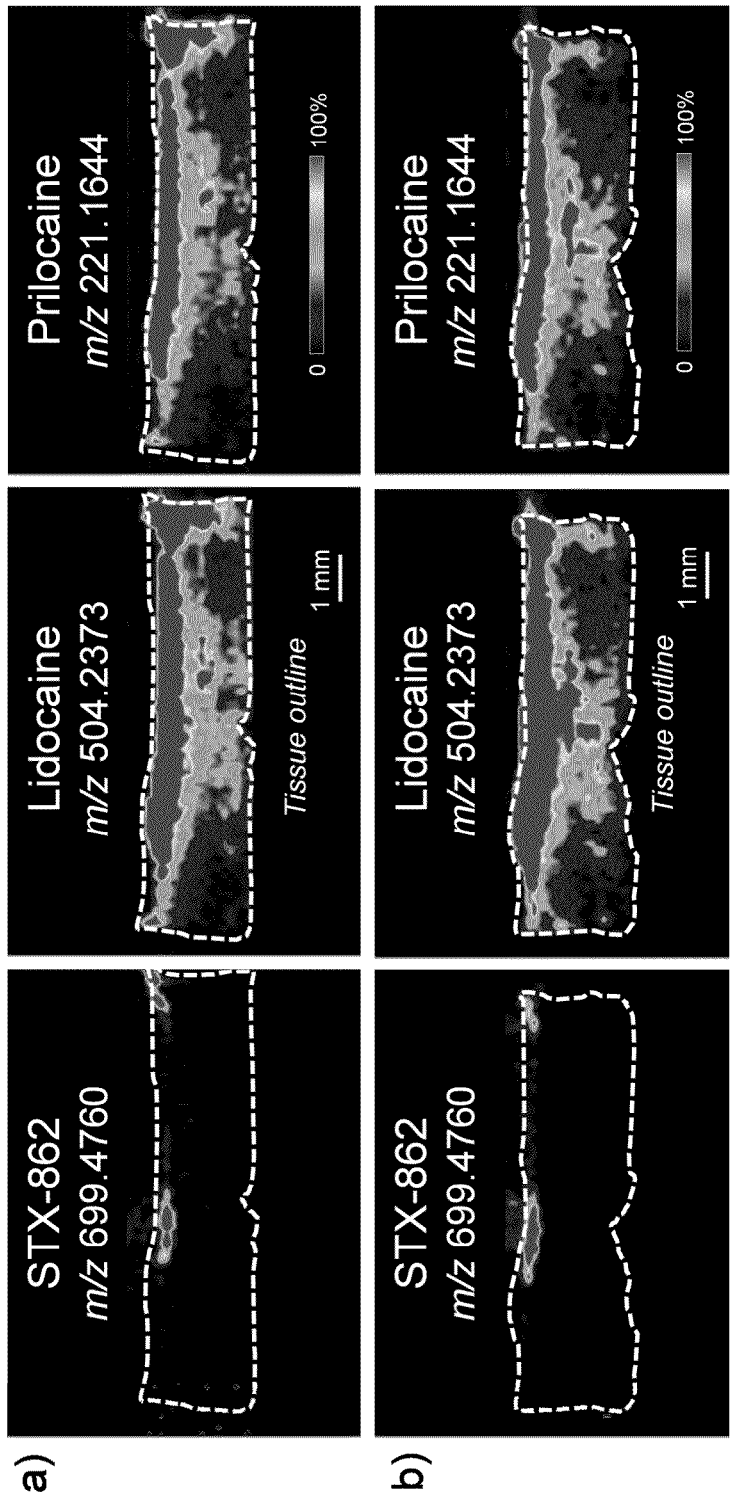
FIG. 8. DESI-MS ion images showing the penetration of STX-862 using EMLA cream as vehicle in two human skin tissue sections. Ion images showing the penetration of lidocaine and prilocaine, compounds with are both present in the EMLA cream formulation, are also presented for the two sections analyzed.

The compounds were further tested using the commercially available EMLA (eutectic mixture of local anesthetics) cream as the vehicle. The EMLA cream is an emulsion in which the oil phase contains an eutectic mixture of lidocaine and prilocaine in a ratio of 1:1 by weight. Aconitine, saxitoxin, STX-862, and BTX-ABC were separately added to the EMLA cream and topically applied these preparations to human skin to investigate their permeation. DESI-MS ion images of lidocaine and prilocaine (m/z 221.1651, 0.3 ppm mass error) show complete skin penetration to the skin hypodermis in the EMLA cream formulation for all 14 samples analyzed and also lateral distribution within the skin section (FIG. 4). In the case of aconitine, similar penetration behavior was observed (average depth 2.49 mm, 4 samples); however, lateral spread of the compound was not observed (FIG. 4a). BTX-ABC also showed complete skin penetration (average depth 1.10 mm, 4 samples), although not as deeply as what was observed for lidocaine/prilocaine (FIG. 4b), while no penetration was observed for saxitoxin (4 samples). STX-862 showed partial skin penetration, with permeation observed through the skin epidermis reaching the superficial dermis, similarly to what observed when using DMSO as the vehicle (FIG. 4c). In a few skin sections obtained from regions in which less cream was applied, complete penetration of the STX-862 compound up to the superficial dermis was seen (average penetration depth of 0.45 mm for 4 samples) (FIG. 8).

Figure 9:
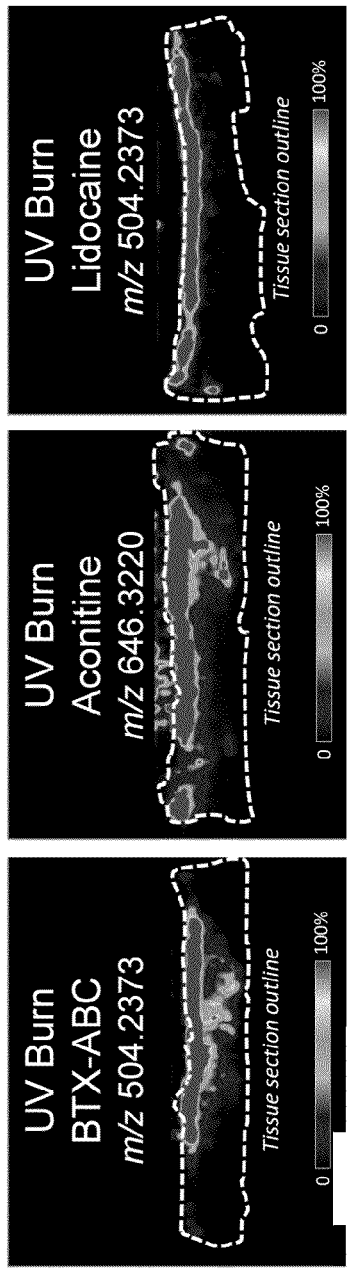
FIG. 9. DESI-MS ion images showing the penetration of BTX-ABC, aconitine and lidocaine using ethanol as vehicle applied to human skin after UV burn.

Topical application of analgesics could be useful in the treatment of pain caused by skin injuries such as sunburn. To test if changes in penetration behavior were observed from UV burn injuries similar to sunburn, a burn injury model was developed by applying UV radiation (300 to 450 nm) to ex-vivo human skin. Benrath et al., *European Journal of Pain—London,* 2001, 5, 155. After the UV burn procedure, the compounds of interest were applied using ethanol as vehicle. UV radiation of ex vivo human skin sufficient to induce DNA damage as measured by increase in growth arrest and DNA-damage-inducible Gadd45a protein did not significantly alter skin penetration of the compounds tested (FIG. 9). Full penetration of lidocaine, aconitine and BTX-ABC and no penetration of STX or STX-862 were observed. The penetration behavior of compounds at 1 hour, 4 hours, and 10 hours of application were also evaluated (see below and FIG. 10 for results).

Figure 5:
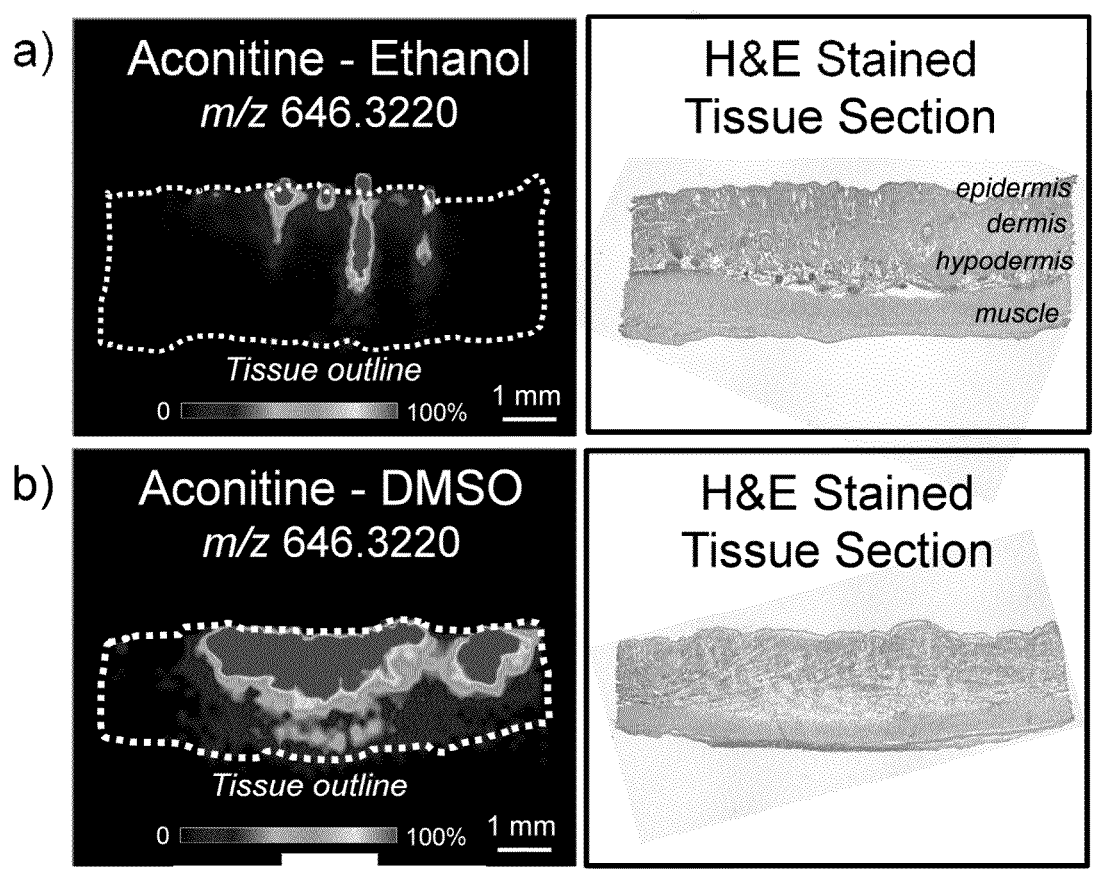
FIG. 5. DESI-MS ion images showing the penetration of aconitine tested in in vivo rat skin using a) ethanol and b) DMSO as vehicles. Optical images of the same tissue sections imaged by DESI after H&E stain are also shown.

In vivo experiments using animal models were performed to test the transdermal permeation in comparison with ex-vivo experiments. Application of the compounds was performed on the shaved back of male rats under anesthesia (see below for experimental details). The animals were sacrificed and their skin removed, sectioned and analyzed following the same experimental procedures used for ex vivo experiments. In vivo experiments were performed using two compounds, aconitine and STX-862 and two vehicles, ethanol and DMSO. Pathologic evaluation of the tissue sections revealed that in all samples analyzed, besides skin epidermis, dermis, and hypodermis layers, muscle tissue was also present. Complete skin penetration of aconitine was observed using both ethanol and DMSO as vehicles, in both cases reaching the muscle layer of the tissue section. In many samples a different spatial distribution within the tissue section was observed in the DESI-MS images depending on the vehicle used for in vivo delivery (FIG. 5). A homogeneous and gradual permeation was consistently observed for aconitine using DMSO as the vehicle. However, and without intending to be bound by theory, with ethanol the distribution pattern of aconitine seen in the DESI-MS ion images suggests that penetration was facilitated through skin hair follicles, an important pathway for the penetration of topically administered substances. Trommer and Neubert, *Skin Pharmacology and Physiology,* 2006, 19, 106. Pathologic evaluation of the H&E stained tissue sections in comparison with the DESI-MS ion images confirmed that aconitine co-localized with the regions of hair follicles within the tissue section. In the case of STX-862, complete penetration of the compound was observed using both ethanol and DMSO, reaching the deep dermis layer of the skin. Overall, deeper penetration was achieved in vivo using DMSO as vehicle for both compounds (1.90 mm in ethanol for 7 samples versus 2.60 mm for 3 samples in DMSO for aconitine; 0.90 mm in ethanol for 5 samples versus 1.12 mm for 7 samples in DMSO for STX-862) (Table 2). The similar trends in penetration of the compounds observed by DESI-MSI using in vivo model in comparison with ex-vivo human skin supports a next step of animal behavioral studies for evaluating the analgesic of the compounds of interest.

In conclusion, the results demonstrate that DESI-MSI is a simple yet sensitive and powerful tool for investigating transdermal permeation of drugs. High mass resolution, histologically compatible DESI-MSI was used to visualize the permeation of topically applied sodium channel blockers and novel synthetic analogs. The approach can be used for both ex vivo human skin and in vivo animal studies, and using injury models such as UV burn. The results further demonstrate that synthetic methodologies may be used to modulate the depth of penetration of neurotoxins by designing less polar synthetic analogs. DESI-MSI methodology can play a guiding role in topical drug development research as a means of assessing the ability of synthetic compounds to penetrate the skin barrier.

Materials/Methods

Synthesis of Saxitoxin, 862 and BTX Derivative:

A strategic modification to a previously published routes to (+)—STX was devised in order to prepare alternate 862. The BTX derivative was synthesized as described above.

Human Tissue:

Human skin samples were obtained from four patients undergoing plastic surgery at Stanford Medical School. All patients gave written informed consent following approved IRB protocols. Within minutes of surgical resection, the excess fat was carefully removed from the inner layers of the skin specimen, which was then placed in a shallow dish partially filled with synthetic interstitial fluid. The surface of the skin was carefully handled and dried prior to compound application. Confined circular treatment areas (d=1 cm) were created by delineating the application area with ink and surrounding the site with Vaseline. For each application site, 25 nmol of compound was applied in 25 µL of vehicle. After 1, 4 or 10 hours of application, the skin was frozen in a −80° C. freezer. Five different compounds were tested on human skin: lidocaine, aconitine, saxitoxin, compound 862, and BTX-ABC derivative. The two vehicles tested were ethanol (Fisher) and DMSO (Fisher).

UV Burn Injury:

Confined circular treatment areas of the human skin samples were exposed to UV (300 to 450 nm, 3100 $mJ/cm^2$) irradiation before application of the compound. UV light was directly applied to skin over 25s using the BlueWave® 200 Version 3.0 UV Curing Spot Lamp with Intensity Adjustment (Dymax Inc., Torrington, Conn.). After UV exposure, 25 nmol of compound was applied in 25 µL of vehicle to each application site. After 4 hours of application, the skin was frozen in a −80° C. freezer.

Animals:

Animal experiments were conducted using ~300 g male Sprague Dawley rats. The hair on the back of the rats was removed 24 h before drug application. Under urethane anesthesia, confined circular treatment areas (d=1 cm) were created by marking the application area with ink and surrounding the application area with Vaseline. For each application site, 25 nmol of the compound was applied in 25 µL of vehicle. After 4 hours of application the animal was sacrificed and its skin removed and frozen in −80° C. freezer. The following compounds were tested in-vivo rat skin: 1) Saxitoxin, 2) Saxitoxinol, 3) Compound 862 and 4) Aconitine in the following vehicles: water, ethanol, DMSO and a cream formulation.

Tissue Sample Preparation:

Frozen skin samples were sectioned at 25 µm thickness using a Leica CM1950 cryostat (Leica Mycrosystems Inc., Buffalo Grove, Ill.). The tissue sections were thaw mounted onto positively charged glass slides. The cryostat section holder and blade were cleaned with 70% ethanol solution in between the preparation of each tissue section to avoid tissue contamination. The slides were stored at −80° C. and prior to analysis dried in a dessicator for approximately 15 minutes.

DESI Imaging:

A lab-built DESI-MS imaging ion source coupled to a LTQ-Orbitrap mass spectrometer was used for tissue imaging. Mass spectra were acquired in the positive ion mode using Orbitrap as the mass analyzer at 60,000 resolving power in the range m/z 100-1100. Pure acetonitrile (Fisher) was used as the histologically compatible solvent system for DESI-MSI at a flow rate of 2 µL/min, and nitrogen gas pressure of 175 psi. The tissue sections were scanned using a 2D moving stage with spatial resolution of 100 µm or 150 µm. The software ImgGenerator (freeware, http://www.msimaging.net/) was used for converting raw files into 2D images. Spatially accurate ion images were assembled using BioMap software (freeware, http://www.maldi-msi.org/).

Histology:

After DESI-MS imaging, the same tissue sections were stained using standard hematoxylin and eosin (H&E). H&E stained tissue sections were evaluated by a veterinary pathologist. Optical images of the H&E stained tissue sections were obtained using a microscope Axioskop 2 Plus (Carl Zeiss International, Thornwood, N.Y.) and digitally overlaid with DESI-MS ion images for compounds depth penetration calculation.

Results & Discussion

Effect of Different Times of Exposure

Figure 10:
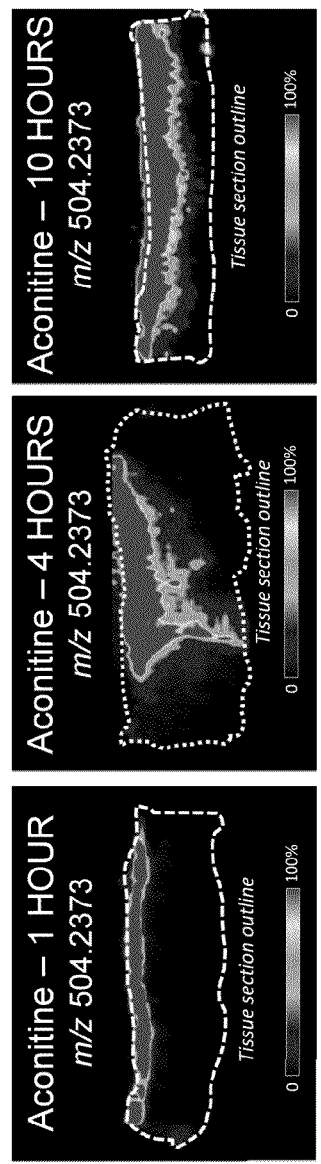
FIG. 10. DESI-MS ion images showing the penetration of aconitine using ethanol as vehicle after 1, 4 and 10 hours of topical application.

The penetration behavior of aconitine, lidocaine, and BTX-ABC at 1 hour, 4 hours, and 10 hours of application was evaluated using ethanol as the vehicle. Aconitine was the only compound that showed a significant change in penetration depth with application time, with increased penetration occurring at 4 and 10 hours of application in comparison to 1 hour (FIG. 10). Lidocaine and BTX-ABC showed similar penetration behavior at 1, 4 and 10 hours of application.

Supporting Tables

TABLE 1

Identification of ions detected from human skin using high mass resolution/high mass accuracy and tandem mass spectrometry analyses.

| Ion detected (m/z) | Tentative Attribution[a] | Molecular Formula[b] | Mass error (ppm)[c] |
|---|---|---|---|
| 140.0679 | 4 aminopentanoic acid | $C_5H_{11}NO_2Na$ | 2.40 |
| 156.0417 | 4 aminopentanoic acid | $C_5H_{11}NO_2K$ | 2.60 |
| 184.0729 | Phosphocholine | $C_5H_{15}NO_4P$ | 2.18 |
| 518.3205 | Lyso-PC(16:0) | $C_{24}H_{50}NO_7PNa$ | 1.99 |
| 534.2945 | Lyso-PC(16:0) | $C_{24}H_{50}NO_7PK$ | 1.36 |
| 615.4940 | DG(34:2) | $C_{37}H_{68}O_5$ | 2.90 |
| 639.4947 | DG(36:4) | $C_{39}H_{68}O_5Na$ | 1.88 |
| 641.5092 | DG(36:3) | $C_{39}H_{70}O_5Na$ | 3.60 |
| 672.4198 | PC(25:0) | $C_{33}H_{64}NO_9PNa$ | 1.80 |
| 688.3937 | PC(25:0) | $C_{33}H_{64}NO_9PK$ | 1.80 |
| 715.5622 | DG(40:2) | $C_{43}H_{80}O_5K$ | 2.10 |
| 717.5781 | DG(40:1) | $C_{43}H_{82}O_5K$ | 1.70 |
| 719.5941 | DG(40:0) | $C_{43}H_{84}O_5K$ | 1.30 |
| 725.5557 | SM(34:1) | $C_{39}H_{79}N_2O_6PNa$ | 0.88 |
| 741.5302 | SM(34:1) | $C_{39}H_{79}N_2O_6PK$ | 0.70 |
| 756.5502 | PC(32:0) | $C_{40}H_{80}NO_8PNa$ | 0.98 |
| 772.5240 | PE(38:5) | $C_{43}H_{76}NO_7PNa$ | 1.10 |
| 772.5241 | PC(32:0) | $C_{40}H_{80}NO_8PK$ | 0.91 |
| 780.5505 | PC(34:2) | $C_{42}H_{80}NO_8PNa$ | 0.90 |
| 782.5681 | PC(34:1) | $C_{42}H_{82}NO_8PNa$ | 0.02 |
| 785.5681 | PG(36:0) | $C_{42}H_{83}O_9P$ | 1.80 |
| 787.5839 | PG(36:0) | $C_{42}H_{85}O_9Na$ | 2.10 |
| 796.5240 | PC(34:2) | $C_{42}H_{80}NO_8PK$ | 1.22 |
| 798.5406 | PC(34:1) | $C_{42}H_{82}NO_8PK$ | 0.11 |
| 804.5502 | PC(36:4) | $C_{44}H_{80}NO_8PNa$ | 1.10 |
| 806.5673 | PC(36:3) | $C_{44}H_{82}NO_8PNa$ | 0.79 |
| 808.5819 | PC(36:2) | $C_{44}H_{84}NO_8PNa$ | 0.72 |
| 811.5840 | PG(38:2) | $C_{44}H_{85}O_9NaP$ | 2.20 |
| 813.5999 | PG(38:2) | $C_{44}H_{87}O_9NaP$ | 2.60 |
| 824.5556 | PC(36:2) | $C_{44}H_{84}NO_8PK$ | 0.72 |
| 825.6926 | TG(48:2) | $C_{51}H_{94}O_6Na$ | 2.00 |
| 828.5358 | PC(38:6) | $C_{46}H_{80}NO_7PK$ | 7.50 |
| 832.5816 | PC(38:4) | $C_{46}H_{84}NO_8PNa$ | 1.18 |
| 848.5555 | PC(38:4) | $C_{46}H_{84}NO_8PK$ | 1.37 |
| 849.6932 | TG(50:4) | $C_{53}H_{94}O_6Na$ | 1.27 |
| 851.7086 | TG(50:3) | $C_{53}H_{96}O_6Na$ | 2.02 |
| 851.7091 | TG(50:3) | $C_{53}H_{96}O_6Na$ | 0.94 |
| 853.7252 | TG(50:2) | $C_{53}H_{98}O_6Na$ | 0.50 |
| 855.7417 | TG(50:1) | $C_{53}H_{100}O_6Na$ | 0.57 |
| 867.6822 | TG(50:3) | $C_{53}H_{96}O_6K$ | 1.90 |
| 869.6984 | TG(50:2) | $C_{53}H_{98}O_6K$ | 1.30 |
| 875.7086 | TG(50:5) | $C_{55}H_{96}O_6Na$ | 1.54 |
| 877.7244 | TG(50:4) | $C_{55}H_{98}O_6Na$ | 1.36 |

TABLE 1-continued

Identification of ions detected from human skin using high mass resolution/high mass accuracy and tandem mass spectrometry analyses.

| Ion detected (m/z) | Tentative Attribution[a] | Molecular Formula[b] | Mass error (ppm)[c] |
|---|---|---|---|
| 879.7406 | TG(54:6) | $C_{55}H_{100}O_6Na$ | 0.57 |
| 881.7582 | TG(54:6) | $C_{55}H_{102}O_6Na$ | 2.25 |
| 891.6826 | TG(52:5) | $C_{55}H_{96}O_6K$ | 1.20 |
| 893.6984 | TG(52:4) | $C_{55}H_{98}O_6K$ | 1.20 |
| 895.7150 | TG(52:3) | $C_{55}H_{100}O_6K$ | 0.09 |
| 897.7321 | TG(54:5) | $C_{55}H_{102}O_6K$ | 1.70 |
| 899.7084 | TG(54:5) | $C_{55}H_{102}O_6K$ | 2.00 |
| 901.7244 | TG(54:6) | $C_{57}H_{98}O_6Na$ | 1.38 |
| 903.7415 | TG(54:5) | $C_{57}H_{100}O_6Na$ | 0.98 |
| 905.7570 | TG(56:7) | $C_{59}H_{100}O_6H$ | 2.50 |
| 907.7733 | TG(54:3) | $C_{57}H_{104}O_6Na$ | 1.56 |
| 907.7735 | TG(56:8) | $C_{59}H_{103}O_6$ | 1.70 |
| 917.6985 | TG(56:7) | $C_{57}H_{98}O_6K$ | 1.10 |
| 919.7145 | TG(54:5) | $C_{57}H_{100}O_6K$ | 0.76 |
| 921.7309 | TG(54:4) | $C_{57}H_{102}O_6K$ | 0.11 |
| 923.7472 | TG(54:3) | $C_{57}H_{104}O_6K$ | 0.99 |
| 929.7557 | TG(56:6) | $C_{59}H_{102}O_6Na$ | 0.40 |
| 943.7137 | TG(56:5) | $C_{59}H_{100}O_6K$ | 0.70 |
| 945.7298 | TG(56:6) | $C_{59}H_{102}O_6K$ | 0.22 |
| 947.7459 | TG(56:7) | $C_{59}H_{104}O_6K$ | 0.22 |

[a]Assignments were based on data obtained from tandem mass spectrometry experiments and high mass accuracy measurements. TG = triacylglycerol; PC = glycerophoscholine; DG = diacylglycerol; SM = sphingomyelins; PG = glycerophosphoglycerols; PE = glycerophosphoethanolamines; (X:Y) denotes the total number of carbons and double bonds in the fatty acid chains.
[b]Molecular formulas of the protonated or sodium/potassium adducts of the assigned molecules.
[c]Mass errors were calculated based on the exact monoisotopic m/z of the protonated or sodium/potassium adducts of the assigned molecules.

TABLE 2

Average penetration depth in human and rat skins for each compound studied using different vehicles.

| Human Skin | | | | |
|---|---|---|---|---|
| Vehicle | Aconitine | Lidocaine | STX-862 | BTX-ABC |
| Ethanol | 3.05 ± 0.91 (n = 6) | 1.24 + 0.38 (n = 5) | No penetration (n = 7) | 2.00 ± 0.61 (n = 4) |
| DMSO | N/A | N/A | 0.62 ± 0.03 (n = 3) | N/A |
| EMLA | 2.49 ± 0.84 (n = 4) | N/A | 0.45 ± 0.10 (n = 4) | 1.10 ± 0.20 (n = 4) |

| Rat Skin | | |
|---|---|---|
| Vehicle | Aconitine | STX-862 |
| Ethanol | 1.90 ± 0.40 (n = 7) | 0.90 ± 0.14 (n = 5) |
| DMSO | 2.60 ± 0.06 (n = 3) | 1.12 ± 0.42 (n = 7) |

All patents, patent publications, and other published references mentioned herein are hereby incorporated by reference in their entireties as if each had been individually and specifically incorporated by reference herein.

While specific examples have been provided, the above description is illustrative and not restrictive. Any one or more of the features of the previously described embodiments can be combined in any manner with one or more features of any other embodiments in the present invention. Furthermore, many variations of the invention will become apparent to those skilled in the art upon review of the specification. The scope of the invention should, therefore, be determined by reference to the appended claims, along with their full scope of equivalents.

What is claimed is:

1. A compound represented by structural formula (I):

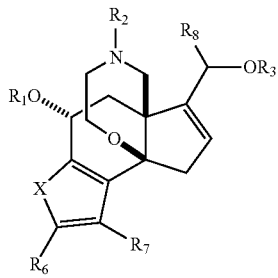

or a pharmaceutically acceptable salt or stereoisomer thereof, wherein:

$R_1$ is hydrogen, alkyl, alkenyl, alkynyl, aryl, aralkyl, heteroaryl, heteroaralkyl, cycloalkyl, cycloalkenyl, cycloalkylalkyl, heterocyclyl, heterocyclylalkyl, or —C(O)R, and is optionally substituted with 1 to 3 A groups;

$R_2$ is hydrogen, alkyl, alkenyl, alkynyl, aryl, aralkyl, heteroaryl, heteroaralkyl, cycloalkyl, cycloalkenyl, cycloalkylalkyl, heterocyclyl, heterocyclylalkyl, or —C(O)R, and is optionally substituted with 1 to 3 A groups;

$R_3$ is hydrogen, alkyl, alkenyl, alkynyl, aryl, aralkyl, heteroaryl, heteroaralkyl, cycloalkyl, cycloalkenyl, cycloalkylalkyl, heterocyclyl, heterocyclylalkyl, or —C(O)R, and is optionally substituted with 1 to 3 A groups;

X is O, S, or

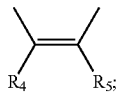

$R_4$, $R_5$, $R_6$, and $R_7$ are independently hydrogen, alkyl, alkenyl, alkynyl, alkoxy, alkylamino, aryl, aryloxy, arylamino, aralkyl, aralkoxy, aralkamino, heteroaryl, heteroaryloxy, heteroarylamino, heteroaralkyl, heteroaralkoxy, heteroaralkamino, cycloalkyl, cycloalkenyl, cycloalkylalkyl, cycloalkoxy, cycloalkamino, heterocyclyl, heterocyclyloxy, heterocyclylamino, heterocyclylalkyl, heterocyclylalkoxy, heterocyclylalkamino, silyl, sulfonyl, hydroxyl, mercapto, amino, alkanoylamino, aroylamino, aralkanoylamino, alkylcarboxy, alkoxycarbonyloxy, aminocarbonyloxy, alkylaminocarbonyloxy, guanidinyl, ureido, halo, trihalomethyl, cyano, nitro, phosphoryl, sulfonyl, sulfonamindo, or azido, and are optionally substituted with 1 to 3 A groups;

$R_8$ is hydrogen, alkyl, alkenyl, alkynyl, alkoxy, aryl, aralkyl, heteroaryl, heteroaralkyl, cycloalkyl, cycloalkenyl, cycloalkylalkyl, heterocyclyl, or heterocyclylalkyl, and is optionally substituted with 1 to 3 A groups;

each R is independently hydrogen, alkyl, alkenyl, alkynyl, alkoxy, alkylamino, aryl, aryloxy, arylamino, aralkyl, aralkoxy, aralkamino, heteroaryl, heteroaryloxy, heteroarylamino, heteroaralkyl, heteroaralkoxy, heteroaralkamino, cycloalkyl, cycloalkenyl, cycloalkylalkyl, cycloalkoxy, cycloalkamino, heterocyclyl, heterocyclyloxy, heterocyclylamino, heterocyclylalkyl, heterocyclylalkoxy, or heterocyclylalkamino, and is optionally substituted with 1 to 3 A groups; and each A is independently alkyl, alkenyl, alkynyl, alkoxy, alkanoyl, alkylamino, aryl, aryloxy, arylamino, aralkyl, aralkoxy, aralkanoyl, aralkamino, heteroaryl, heteroaryloxy, heteroarylamino, heteroaralkyl, heteroaralkoxy, heteroaralkanoyl, heteroaralkamino, cycloalkyl, cycloalkenyl, cycloalkylalkyl, cycloalkoxy, cycloalkanoyl, cycloalkamino, heterocyclyl, heterocyclyloxy, heterocyclylamino, heterocyclylalkyl, heterocyclylalkoxy, heterocyclylalkanoyl, heterocyclylalkamino, hydroxyl, mercapto, amino, alkanoylamino, aroylamino, aralkanoylamino, alkylcarboxy, alkoxycarbonyloxy, aminocarbonyloxy, alkylaminocarbonyloxy, guanidinyl, ureido, halo, trihalomethyl, cyano, nitro, phosphoryl, sulfonyl, sulfonamido, or azido;

wherein each heteroaryl group is independently a 5-6 membered aromatic ring or a 9-12 membered bicyclic ring system wherein at least one ring is an aromatic ring, each aromatic ring having 1-3 heteroatoms selected from O, N, and S; each heterocyclyl group is independently a 3-10 membered saturated or partially unsaturated monocyclic or bicyclic ring having 1-3 heteroatoms selected from O, N, and S; and each cycloalkyl and cycloalkenyl group is independently a 3-10 membered non-aromatic saturated or unsaturated ring in which each atom of the ring is carbon.

2. The compound according to claim 1, wherein $R_1$ is hydrogen, alkyl, or —C(O)R, and is optionally substituted with 1 to 3 A groups.

3. The compound according to claim 2, wherein $R_1$ is hydrogen or alkyl.

4. The compound according to claim 3, wherein $R_1$ is methoxymethyl.

5. The compound according to claim 1, wherein $R_2$ is hydrogen, alkyl, or —C(O)R, and is optionally substituted with 1 to 3 A groups.

6. The compound according to claim 5, wherein $R_2$ is alkyl, and is optionally substituted with 1 to 3 A groups.

7. The compound according to claim 6, wherein $R_2$ is methyl.

8. The compound according to claim 1, wherein $R_3$ is alkyl, aryl, heteroaryl, or —C(O)R, and is optionally substituted with 1 to 3 A groups.

9. The compound according to claim 8, wherein $R_3$ is —C(O)R, and R is alkyl, aryl, heteroaryl, arylamino, or heteroarylamino, and is optionally substituted with 1 to 3 A groups.

10. The compound according to claim 9, wherein $R_3$ is —C(O)R, and R is a substituted pyrrole.

11. The compound according to claim 10, wherein $R_3$ is —C(O)R, and R is

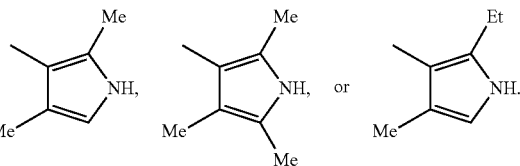

12. The compound according to claim 1, wherein $R_4$, $R_5$, $R_6$, and $R_7$ are independently hydrogen, alkyl, alkoxyl, cycloalkyl, heterocyclyl, silyl, sulfonyl, alkoxycarbonyloxy, hydroxyl, mercapto, amino, halo, cyano, or nitro, and are optionally substituted with 1 to 3 A groups.

13. The compound according to claim 12, wherein $R_4$, $R_5$, $R_6$, and $R_7$ are independently hydrogen, alkyl, alkoxy, silyl, or halo.

14. The compound according to claim 13, wherein $R_4$, $R_5$, $R_6$, and $R_7$ are hydrogen.

15. The compound according to claim 1, wherein $R_8$ is hydrogen or alkyl.

16. The compound according to claim 15, wherein $R_8$ is methyl.

17. The compound according to claim 1, wherein R is independently alkyl, aryl, heteroaryl, arylamino, or heteroarylamino.

18. The compound according to claim 1, wherein X is O or

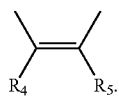

19. The compound according to claim 1, wherein $R_1$ is hydrogen or —C(O)R, and is optionally substituted with 1 to 3 A groups;

$R_2$ is hydrogen, alkyl, or —C(O)R, and is optionally substituted with 1 to 3 A groups;

$R_3$ is —C(O)R, and R is alkyl, aryl, heteroaryl, arylamino, or heteroarylamino, and is optionally substituted with 1 to 3 A groups;

$R_4$, $R_5$, $R_6$, and $R_7$ are independently hydrogen, alkyl, alkoxyl, cycloalkyl, heterocyclyl, silyl, sulfonyl, alkylaminocarbonyloxy, hydroxyl, mercapto, amino, halo, cyano, or nitro, and are optionally substituted with 1 to 3 A groups;

$R_8$ is hydrogen or alkyl;

R is independently alkyl, aryl, heteroaryl, arylamino, or heteroarylamino; and

X is O or

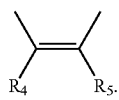

20. The compound according to claim 1, wherein the compound is any one of the following compounds:

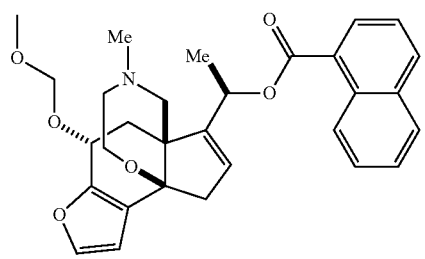

-continued

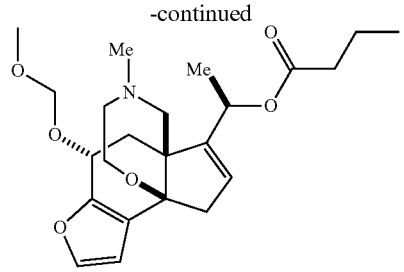

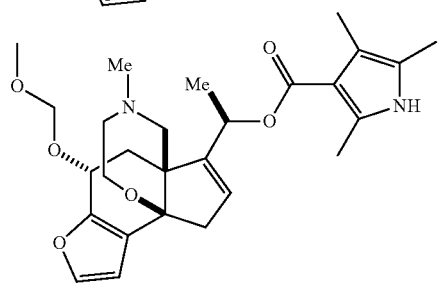

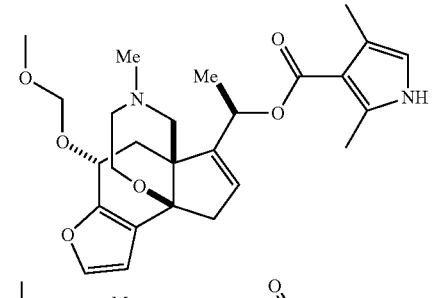

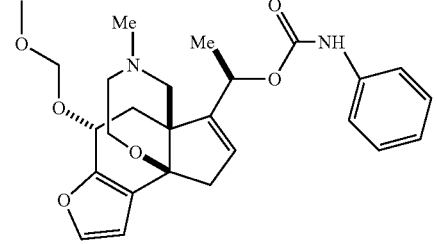

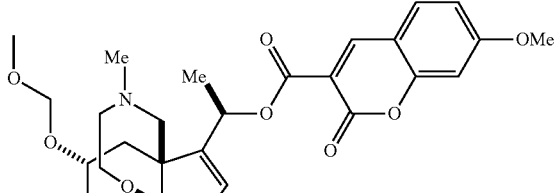

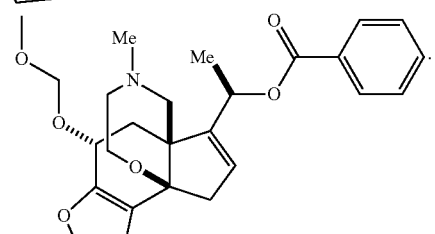

21. A pharmaceutical composition comprising the compound of claim 1 and a pharmaceutically acceptable carrier.

22. A packaged pharmaceutical comprising the pharmaceutical composition of claim 21 and instructions for using the composition to treat pain in a mammalian subject.

23. A method of treatment in a subject, comprising administering to the subject a compound of claim 1 in an amount effective to treat the subject, wherein the subject suffers from pain.

24. The method of claim 23, wherein the pain is acute pain, anal fissure pain, arthritis pain, back pain, cancer pain, chronic pain, dental pain, fibromyalgia pain, joint pain, migraine headache pain, neck pain, visceral pain, neuropathic pain, obstetric pain, post-herpetic neuralgia pain, post-operative pain, sympathetically maintained pain, shingles pain, tension headache pain, trigeminal neuralgia pain, myositis pain, musculoskeletal pain, lower back pain, pain from sprains and strains, pain associated with functional bowel disorders such as non-ulcer dyspepsia, non-cardiac chest pain and irritable bowel syndrome, pain associated with myocardial ischemia, toothache pain, or pain from dysmenorrhea.

25. The method of claim 23, wherein the pain is sunburn pain.

26. A pharmaceutical composition comprising the compound of claim 1 and a vehicle that modulates transdermal permeation of the compound.

27. The composition of claim 26, wherein the vehicle is an organic solvent or an emulsion.

28. The composition of claim 27, wherein the organic solvent is an alcohol or dimethyl sulfoxide.

29. The composition of claim 28, wherein the alcohol is ethanol.

30. The composition of claim 27, wherein the emulsion is a cream.

31. The composition of claim 30, wherein the cream is a eutectic mixture of local anesthetics.

32. A compound represented by structural formula (I'):

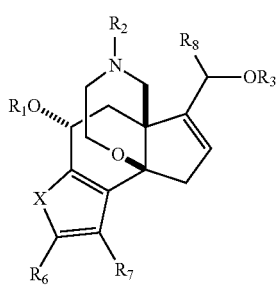

or a stereoisomer thereof, wherein:

$R_1$ is hydrogen, alkyl, alkenyl, alkynyl, aryl, aralkyl, heteroaryl, heteroaralkyl, cycloalkyl, cycloalkenyl, cycloalkylalkyl, heterocyclyl, heterocyclylalkyl, —C(O)R, or a protecting group, and is optionally substituted with 1 to 3 A groups;

$R_2$ is hydrogen, alkyl, alkenyl, alkynyl, aryl, aralkyl, heteroaryl, heteroaralkyl, cycloalkyl, cycloalkenyl, cycloalkylalkyl, heterocyclyl, heterocyclylalkyl, —C(O)R, or a protecting group, and is optionally substituted with 1 to 3 A groups;

$R_3$ is hydrogen, alkyl, alkenyl, alkynyl, aryl, aralkyl, heteroaryl, heteroaralkyl, cycloalkyl, cycloalkenyl, cycloalkylalkyl, heterocyclyl, heterocyclylalkyl, —C(O)R, or a protecting group, and is optionally substituted with 1 to 3 A groups;

X is O, S, or

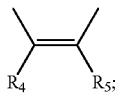

$R_4$, $R_5$, $R_6$, and $R_7$ are independently hydrogen, alkyl, alkenyl, alkynyl, alkoxy, alkylamino, aryl, aryloxy, arylamino, aralkyl, aralkoxy, aralkamino, heteroaryl, heteroaryloxy, heteroarylamino, heteroaralkyl, heteroaralkoxy, heteroaralkamino, cycloalkyl, cycloalkenyl, cycloalkylalkyl, cycloalkoxy, cycloalkamino, heterocyclyl, heterocyclyloxy, heterocyclylamino, heterocyclylalkyl, heterocyclylalkoxy, heterocyclylalkamino, silyl, sulfonyl, hydroxyl, mercapto, amino, alkanoylamino, aroylamino, aralkanoylamino, alkylcarboxy, alkoxycarbonyloxy, aminocarbonyloxy, alkylaminocarbonyloxy, guanidinyl, ureido, halo, trihalomethyl, cyano, nitro, phosphoryl, sulfonyl, sulfonamindo, or azido, and are optionally substituted with 1 to 3 A groups;

$R_8$ is hydrogen, alkyl, alkenyl, alkynyl, alkoxy, aryl, aralkyl, heteroaryl, heteroaralkyl, cycloalkyl, cycloalkenyl, cycloalkylalkyl, heterocyclyl, or heterocyclylalkyl, and is optionally substituted with 1 to 3 A groups;

each R is independently hydrogen, alkyl, alkenyl, alkynyl, alkoxy, alkylamino, aryl, aryloxy, arylamino, aralkyl, aralkoxy, aralkamino, heteroaryl, heteroaryloxy, heteroarylamino, heteroaralkyl, heteroaralkoxy, heteroaralkamino, cycloalkyl, cycloalkenyl, cycloalkylalkyl, cycloalkoxy, cycloalkamino, heterocyclyl, heterocyclyloxy, heterocyclylamino, heterocyclylalkyl, heterocyclylalkoxy, or heterocyclylalkamino, and is optionally substituted with 1 to 3 A groups; and each A is independently alkyl, alkenyl, alkynyl, alkoxy, alkanoyl, alkylamino, aryl, aryloxy, arylamino, aralkyl, aralkoxy, aralkanoyl, aralkamino, heteroaryl, heteroaryloxy, heteroarylamino, heteroaralkyl, heteroaralkoxy, heteroaralkanoyl, heteroaralkamino, cycloalkyl, cycloalkenyl, cycloalkylalkyl, cycloalkoxy, cycloalkanoyl, cycloalkamino, heterocyclyl, heterocyclyloxy, heterocyclylamino, heterocyclylalkyl, heterocyclylalkoxy, heterocyclylalkanoyl, heterocyclylalkamino, hydroxyl, mercapto, amino, alkanoylamino, aroylamino, aralkanoylamino, alkylcarboxy, alkoxycarbonyloxy, aminocarbonyloxy, alkylaminocarbonyloxy, guanidinyl, ureido, halo, trihalomethyl, cyano, nitro, phosphoryl, sulfonyl, sulfonamido, or azido;

wherein each heteroaryl group is independently a 5-6 membered aromatic ring or a 9-12 membered bicyclic ring system wherein at least one ring is an aromatic ring, each aromatic ring having 1-3 heteroatoms selected from O, N, and S; each heterocyclyl group is independently a 3-10 membered saturated or partially unsaturated monocyclic or bicyclic ring having 1-3 heteroatoms selected from O, N, and S; and each cycloalkyl and cycloalkenyl group is independently a 3-10 membered non-aromatic saturated or unsaturated ring in which each atom of the ring is carbon.

33. The compound according to claim 32, wherein $R_1$ is hydrogen, alkyl, —C(O)R, or a protecting group, and is optionally substituted with 1 to 3 A groups.

34. The compound according to claim 33, wherein $R_1$ is hydrogen, alkyl, or a protecting group.

35. The compound according to claim 32, wherein $R_2$ is hydrogen, alkyl, —C(O)R, or a protecting group, and is optionally substituted with 1 to 3 A groups.

36. The compound according to claim 32, wherein $R_3$ is alkyl, aryl, heteroaryl, or —C(O)R, and is optionally substituted with 1 to 3 A groups.

37. The compound according to claim 32, wherein $R_4$, $R_5$, $R_6$, and $R_7$ are independently hydrogen, alkyl, alkoxyl, cycloalkyl, heterocyclyl, silyl, sulfonyl, alkoxycarbonyloxy, hydroxyl, mercapto, amino, halo, cyano, or nitro, and are optionally substituted with 1 to 3 A groups.

38. The compound according to claim 32, wherein $R_8$ is hydrogen or alkyl.

39. The compound according to claim 32, wherein R is independently alkyl, aryl, heteroaryl, arylamino, or heteroarylamino.

40. The compound according to claim 32, wherein X is O or

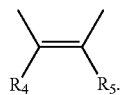

41. The compound according to claim 32, wherein
$R_1$ is hydrogen, —C(O)R, or a protecting group, and is optionally substituted with 1 to 3 A groups;
$R_2$ is hydrogen, alkyl, —C(O)R, or a protecting group, and is optionally substituted with 1 to 3 A groups;
$R_3$ is —C(O)R, and R is alkyl, aryl, heteroaryl, arylamino, or heteroarylamino, and is optionally substituted with 1 to 3 A groups;
$R_4$, $R_5$, $R_6$, and $R_7$ are independently hydrogen, alkyl, alkoxyl, cycloalkyl, heterocyclyl, silyl, sulfonyl, alkoxycarbonyloxy, hydroxyl, mercapto, amino, halo, cyano, or nitro, and are optionally substituted with 1 to 3 A groups;
$R_8$ is hydrogen or alkyl;
R is independently alkyl, aryl, heteroaryl, arylamino, or heteroarylamino; and
X is O or

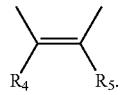

* * * * *